(12) United States Patent
Ariely et al.

(10) Patent No.: US 12,420,065 B2
(45) Date of Patent: Sep. 23, 2025

(54) DEVICES, SYSTEMS, AND METHODS FOR STABILIZING MEDICAL TUBING PROTRUDING FROM A PATIENT

(71) Applicant: HAITEC Medical, Inc., Solana Beach, CA (US)

(72) Inventors: Adam M. Ariely, Encinitas, CA (US); Juraj Letko, Chicago, IL (US)

(73) Assignee: HAITEC Medical, Inc., Solana Beach, CA (US)

( * ) Notice: Subject to any disclaimer, the term of this patent is extended or adjusted under 35 U.S.C. 154(b) by 0 days.

(21) Appl. No.: 18/677,012

(22) Filed: May 29, 2024

(65) Prior Publication Data

US 2024/0307662 A1 Sep. 19, 2024

Related U.S. Application Data

(60) Continuation-in-part of application No. 18/136,815, filed on Apr. 19, 2023, now abandoned, which is a
(Continued)

(51) Int. Cl.
*A61M 25/02* (2006.01)

(52) U.S. Cl.
CPC ..... *A61M 25/02* (2013.01); *A61M 2025/0206* (2013.01); *A61M 2025/0273* (2013.01)

(58) Field of Classification Search
CPC ... Y10S 128/26; A41D 13/1254; A41B 9/007; A61M 2025/0206; A61M 2025/0266;
(Continued)

(56) References Cited

U.S. PATENT DOCUMENTS

| 3,279,469 A | * | 10/1966 | Schustack | A41C 1/003 |
| | | | | 2/408 |
| 3,422,817 A | * | 1/1969 | Mishkin | A61M 25/02 |
| | | | | 128/207.14 |

(Continued)

FOREIGN PATENT DOCUMENTS

| CN | 112121285 A | * | 12/2020 | | A61M 1/84 |
| FR | 2517544 A1 | * | 12/1981 | | A61M 25/02 |

(Continued)

OTHER PUBLICATIONS

International Search Report and Written Opinion for Application No. PCT/US2022/038944, mailed on Dec. 8, 2022, 19 pages.

*Primary Examiner* — Bhisma Mehta
*Assistant Examiner* — Adam J. Cermak
(74) *Attorney, Agent, or Firm* — Veros Legal Solutions, LLP

(57) ABSTRACT

Devices, systems, and methods for stabilizing medical tubing protruding from a patient. In various embodiments of the present disclosure, a medical tubing stabilization device is provided that may include a tube stabilization patch and a complementary medical garment. The tube stabilization patch may be applied to a patient who has medical tubing or a catheter protruding from their body to reduce or dampen movement on the body from the medical tubing in relation to the patient. The medical garment may be worn by the patient and placed in combination with the tube stabilization patch to further reduce the relative movement of the medical tubing. The present disclosure may be directed to reducing the level of medical tubing movement, both externally and internally, that a patient may experience, which decreases the risk of infection caused by catheterization of patients.

21 Claims, 30 Drawing Sheets

Related U.S. Application Data division of application No. 17/877,301, filed on Jul. 29, 2022, now abandoned.

(60) Provisional application No. 63/227,855, filed on Jul. 30, 2021.

(58) Field of Classification Search
CPC .. A61M 2025/0253; A61M 2025/0273; A61M 25/02

See application file for complete search history.

(56) References Cited

U.S. PATENT DOCUMENTS

| | | | | |
|---|---|---|---|---|
| 3,683,911 | A * | 8/1972 | McCormick | A61M 25/02 128/DIG. 26 |
| 4,040,427 | A * | 8/1977 | Winnie | A61M 25/02 128/846 |
| 4,579,120 | A * | 4/1986 | MacGregor | A61M 25/02 600/397 |
| 4,637,078 | A * | 1/1987 | Southwell | A61F 5/44 2/408 |
| 4,666,432 | A | 5/1987 | McNeish et al. | |
| 4,675,918 | A * | 6/1987 | O'Brien | A41B 9/007 2/919 |
| 4,699,616 | A * | 10/1987 | Nowak | A61M 25/02 128/DIG. 26 |
| 4,835,795 | A * | 6/1989 | Lonon | A41B 9/08 2/408 |
| 5,207,652 | A * | 5/1993 | Kay | A61M 25/02 128/DIG. 26 |
| 5,295,945 | A * | 3/1994 | Miller | A41D 13/1254 2/408 |
| 5,447,492 | A * | 9/1995 | Cartmell | A61F 13/0203 602/41 |
| 5,688,248 | A * | 11/1997 | Lessing, Jr. | A61M 25/02 604/179 |
| 5,806,096 | A * | 9/1998 | Pennington | A41D 13/1272 604/179 |
| 5,833,666 | A * | 11/1998 | Davis | A61M 25/02 128/DIG. 26 |
| 6,014,777 | A * | 1/2000 | Gupton | A41D 13/1254 2/403 |
| 6,032,289 | A * | 3/2000 | Villapiano | A41D 13/1245 2/102 |
| 6,477,710 | B1 * | 11/2002 | Ojoyeyi | A41D 13/1236 2/254 |
| 8,690,835 | B1 * | 4/2014 | Parris | A41D 13/1236 604/179 |
| 9,119,749 | B2 * | 9/2015 | Close | A61F 13/49007 |
| D761,419 | S * | 7/2016 | Fitzgerald | A61M 25/02 D24/128 |
| 9,888,728 | B1 * | 2/2018 | Young | A61F 5/451 |
| 2003/0229930 | A1 * | 12/2003 | Carlson | A41D 13/1254 2/114 |
| 2007/0032761 | A1 * | 2/2007 | Jonsson | A61M 25/02 604/180 |
| 2007/0271670 | A1 * | 11/2007 | Hwang | A41B 9/001 2/69 |
| 2008/0066213 | A1 * | 3/2008 | Ha | A41B 9/02 2/400 |
| 2009/0089913 | A1 * | 4/2009 | Ehrlickman | A41D 13/1254 2/338 |
| 2010/0057010 | A1 * | 3/2010 | Goransson | A61B 17/3417 604/164.04 |
| 2010/0137805 | A1 | 6/2010 | Farchione et al. | |
| 2011/0023208 | A1 * | 2/2011 | Liao | A61M 25/02 2/102 |
| 2011/0119814 | A1 * | 5/2011 | Caliste | A41D 13/1254 2/400 |
| 2012/0078190 | A1 * | 3/2012 | Austin | A61M 25/02 2/300 |
| 2014/0350474 | A1 * | 11/2014 | Andreae | A61M 25/02 604/179 |
| 2015/0320987 | A1 * | 11/2015 | Burns | A41B 13/06 5/494 |
| 2016/0022509 | A1 * | 1/2016 | Reddy | A61F 13/47 604/385.01 |
| 2016/0303350 | A1 * | 10/2016 | Konstantarakis | A61M 39/0247 |
| 2017/0087336 | A1 * | 3/2017 | Chang | A61M 25/02 |
| 2018/0177242 | A1 * | 6/2018 | Johnson | A61M 1/285 |
| 2018/0289922 | A1 * | 10/2018 | Burkholz | A61M 25/02 |
| 2020/0046046 | A1 | 2/2020 | Bentley | |
| 2020/0046047 | A1 * | 2/2020 | Bentley | A41D 13/1245 |
| 2020/0046945 | A1 * | 2/2020 | Vera | G09F 3/0295 |
| 2020/0376233 | A1 * | 12/2020 | Morales, Jr. | A41D 13/1245 |
| 2021/0052025 | A1 * | 2/2021 | Colon-Alfonso | A41D 27/10 |
| 2021/0100681 | A1 * | 4/2021 | Miles | A61F 5/4404 |
| 2021/0138199 | A1 * | 5/2021 | Palya | A61M 25/02 |
| 2021/0162180 | A1 * | 6/2021 | Gershbaum | A41D 13/1254 |
| 2021/0186128 | A1 * | 6/2021 | Gettman | A61B 90/05 |
| 2022/0000187 | A1 * | 1/2022 | Li | A41D 13/129 |
| 2022/0168016 | A1 * | 6/2022 | Honda | A61B 17/42 |
| 2023/0035969 | A1 * | 2/2023 | Ariely | A61M 25/02 |
| 2023/0218864 | A1 * | 7/2023 | Walter-Engelsma | A61M 27/00 604/178 |
| 2023/0310027 | A1 * | 10/2023 | Neely | A61B 17/3462 604/93.01 |
| 2023/0321401 | A1 * | 10/2023 | Berglund | A61F 13/0269 604/180 |
| 2024/0307662 | A1 * | 9/2024 | Ariely | A61M 25/02 |

FOREIGN PATENT DOCUMENTS

| | | | | |
|---|---|---|---|---|
| FR | 2517544 A | | 6/1983 | |
| KR | 101064844 B1 | * | 9/2011 | ............ A61M 25/02 |
| KR | 20220117552 A | * | 8/2022 | ............ A61M 27/00 |
| KR | 20220117552 A1 | | 8/2022 | |
| WO | WO-2020146252 A1 | * | 7/2020 | ......... A61B 17/3403 |

* cited by examiner

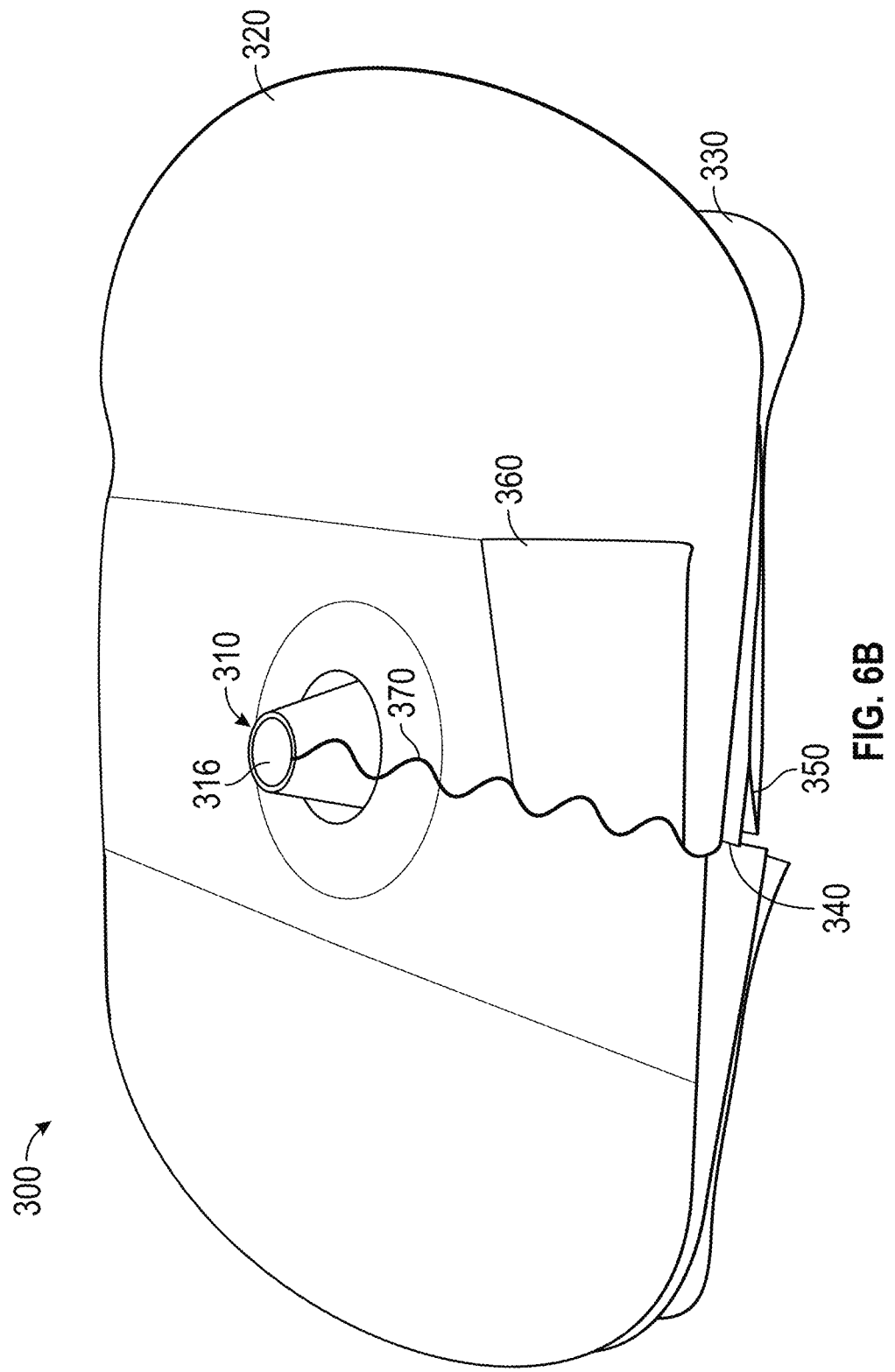

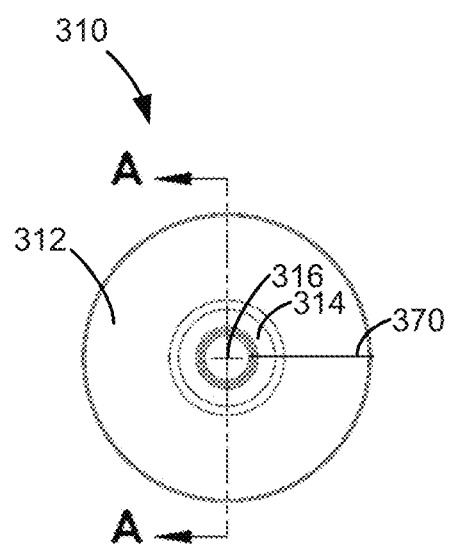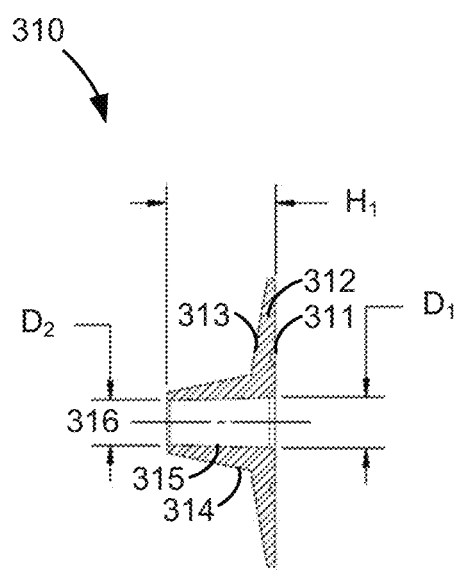
FIG. 6C
FIG. 6D

////// Adhesive Side    ☐ Non-Adhesive Side

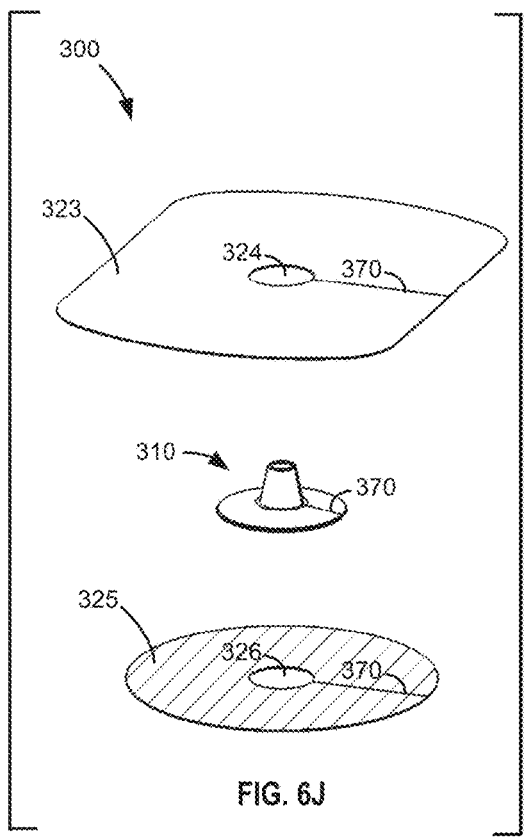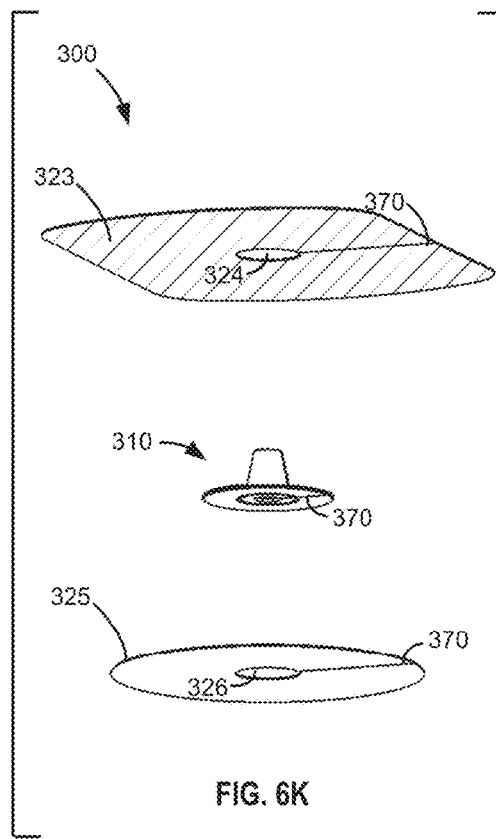

Adhesive Side   Non-Adhesive Side

DEVICES, SYSTEMS, AND METHODS FOR STABILIZING MEDICAL TUBING PROTRUDING FROM A PATIENT

CROSS-REFERENCE TO RELATED APPLICATIONS

This application is a continuation-in-part of U.S. patent application Ser. No. 18/136,815, filed Apr. 19, 2023, which is a divisional of U.S. patent application Ser. No. 17/877,301, filed Jul. 29, 2022, which claims priority to U.S. Provisional Patent Application No. 63/227,855, filed Jul. 30, 2021, the contents of all of which are each hereby incorporated by reference in their entirety.

TECHNICAL FIELD

The present disclosure relates generally to devices, systems, and methods for stabilizing medical tubing protruding from or into a patient's body. In particular, some implementations may relate to such devices, systems, and methods that prevent or reduce relative movement between the medical tubing and the patient by dampening forces acting on the body caused by the movement and/or pull of the tubing.

BACKGROUND OF THE INVENTION

Many areas of medicine involve fluid drainage from a patient's tissues, organs, or cavities. Usually this involves the use of flexible medical tubing extending from those tissues, organs, and/or cavities, which are connected to a fluid collection device outside of or fastened to the patient. Conventional devices, systems, and methods are problematic as they allow for lateral, longitudinal, and/or internal movement of the tubing or fluid collection device in relation to the patient insertion or attachment site. Such lateral, longitudinal, and/or internal movement can cause trauma, contamination, and infection, both at the tubing's insertion sites (e.g., skin, cavity, organ, genitalia, urethra, etc.) as well as in associated tissues. For example, it was previously suspected that catheter-associated urinary tract infections (CAUTIs) were primarily caused by a microfilm of infection that organically travels up the urethra. However, such organic microfilm progression typically takes several days to cause CAUTIs and patients commonly develop CAUTIs as quickly as the first day on-catheter. Accordingly, an additional and/or alternative cause of such CAUTIs may be the introduction of contaminating microorganisms from the exterior surface of the tubing into the patient's tissues and vasculature due to a portion of the tubing adjacent to the patient moving in to and out of the patient (I.e., a motion sometimes referred to as "pistoning"). Contrary to the customary understanding in the industry, it is applicant's belief that contamination from such pistoning motion is significantly greater than from mere organic microfilm travel up into the urethra.

The problems associated with the movement of catheters, particularly urinary catheters such as in-dwelling (or Foley) catheters, suprapubic urinary catheters, ileostomy catheters, chest tubes, and the like, are particularly pronounced, because the medical tubing used to drain the affected organ or tissue protrude directly outward from the patient. These tubes tend to be of larger diameter, have heavier wall thickness and, therefore, tend to be more rigid than venous catheter tubes. Although more rigid than venous catheter tubes, typical urinary catheter tubes are still flexible medical tubing, usually made from Latex, a Latex blend, and/or silicone, and configured to pass through the urethra into the bladder.

In-dwelling urinary catheters 500, for example, as shown in FIG. 20, are typically retained inside the bladder by a balloon 506 located at the inserted end 504 of catheter 500, sometimes referred to as the distal end. Balloon 506 is often inflated with sterile water or saline solution. The diameter of inflated balloon 506 is much greater than the internal diameter of the urethra, which can assist in holding the catheter inside the patient's body. Catheter diameters are typically sized by the French (Fr) catheter scale, which is a measure of a catheter's outer diameter, with the French size being three times the outer diameter, measured in millimeters (mm) (e.g., 3 Fr is equivalent to 1 mm of outer diameter). For example, typical urinary catheters range from 10 Fr (3.3 mm) to 28 Fr (9.3 mm). The external end 502 of catheter 500, sometimes referred to as the proximal end, is typically attached to a drainage tube that leads to a drainage (or collection) bag (not shown). Catheter 500 and/or the drainage tube may be conventionally secured to one of the patient's legs to help control catheter and drainage tubing movement and in an attempt to mitigate the resultant effects of the movement of catheter 500 on the patient.

To minimize tension on the catheter, care must be taken when securing the drainage tube to ensure that a sufficient length of slack tubing is available to form a curve or loop in the tubing. If insufficient tubing slack is available, the risk of bladder damage increases. Slack drainage tubing, however, also creates a problem where, while the inflated catheter balloon reduces the risk of the catheter from accidentally being pulled out of the bladder, nothing restricts the catheter from moving further into the bladder. Because of the extra length that slack tubing provides, the catheter (and balloon) can move within the bladder every time a patient's leg moves. Additionally, catheters have a natural rigidity (i.e., it wants to be straight), thus the extra slack in the catheter does not stay curved and results in the tip of the catheter pushing into the lining of the bladder because the opposing end of the catheter (the portion external to the body) is fixed by the leg securement device. Should the catheter move far enough into the bladder, the top and/or internal end (e.g., the tip that extends beyond the balloon in the bladder) of the catheter contacts the bladder lining opposite the urethra, which may cause bladder spasms, a persistent compulsion to urinate, as well as other trauma including but not limited to bladder bruising. Repeated movement of the catheter at the opening of the urethra can also cause urethral discomfort, irritation, and/or trauma, in addition to increasing a patient's risk of contracting a CAUTI.

According to the Centers for Disease Control and Prevention (CDC), each year in the U.S., 30 million urinary catheters are inserted into over 5 million patients in acute care hospitals and extended care facilities. Up to 25% of these patients, over one million patients per year, develop CAUTI when subject to catheterization for at least 7 days, with the daily risk amounting to approximately 5%. CAUTI is the most common nosocomial infection, and the second most common cause of nosocomial blood stream infection. Studies suggest that patients who develop CAUTI have an increased institutional death rate, unrelated, but in addition to, an increased risk of developing urosepsis. As the population grows in size and increases in age, and as average life expectancy increases, each year more people will require catheterization. Moreover, patients who require catheterization are often scared, in pain and mentally or psychologically exhausted from prior medical treatments and/or the prognosis of their medical conditions. These factors, in addition to the increasing unwillingness of the U.S. Centers for Medicare and Medicaid (alongside a growing number of health insurance companies) to pay hospitals for nosocomial infection treatment, creates an urgent need for additional solutions for the management and stabilization of medical tubing, including in-dwelling urinary catheters, suprapubic urinary catheters, ileostomy catheters, chest tubes, and the like.

SUMMARY OF THE INVENTION

Devices, systems, and methods are described herein for a medical tubing stabilization device. The medical tubing stabilization device may include a tube stabilization patch, which further may include a tube engaging element that can be configured to receive medical tubing; a patient attachment element that may be coupled to the tube engaging element; and an access separation, which may allow for medical tubing to pass from outside the tube stabilization patch, through the patient attachment element, and into the tube engaging element.

The medical tubing stabilization device may further include a medical garment. Such a medical garment may have a body portion configured to wrap around the patient. The body portion may be coupled directly to, or indirectly with, through a perineal portion, an adjustable flap portion that is securable to an anterior portion of the body portion and various attachment mechanisms that allow for the adjustable strap portion to be releasably and adjustably coupled to the anterior portion of the body portion. The adjustable flap portion may also include, or be configured to form in the aggregate, a securing mechanism that may both hold the tube stabilization patch and the tube engaging element in place. Such a securing mechanism may comprise, or form in the aggregate, an opening or exit port that may allow for the tube engaging element to be secured between portions of the securing mechanism.

Other features and aspects of the disclosure will become apparent from the following detailed description, taken in conjunction with the accompanying figures, which illustrate, by way of example, the features in accordance with various embodiments. The summary is not intended to limit the scope of the invention, which is defined solely by the claims attached hereto.

BRIEF DESCRIPTION OF DRAWINGS

The technology disclosed herein, in accordance with one or more various embodiments, is described in detail with reference to the following figures. The figures are provided for purposes of illustration only and merely depict typical or example embodiments of the disclosed technology. These figures are provided to facilitate the reader's understanding of the disclosed technology and shall not be considered limiting of the breadth, scope, or applicability thereof. It should be noted that for clarity and ease of illustration, these figures are not necessarily made to scale.

FIG. 6B illustrates a perspective view of another example tube stabilization patch of a device or system for stabilizing medical tubing protruding from a patient, according to various embodiments of the present disclosure;

FIG. 6C illustrates a top view of a tube engaging element of a tube stabilization patch, according to various embodiments of the present disclosure;

FIG. 6D illustrates a side cutaway view of the tube engaging element of FIG. 6C as viewed along a cutline A-A, according to various embodiments of the present disclosure;

FIG. 6J illustrates an exploded perspective view of a second configuration of a tube stabilization patch as viewed from the top, according to various embodiments of the present disclosure;

FIG. 6K illustrates an exploded perspective view of the second configuration of the tube stabilization patch of FIG. 6J as viewed from the bottom;

FIGS. 19A-19D illustrate respective side views of several tube engaging elements, while

The figures are not intended to be exhaustive or to limit the invention to the precise form disclosed. It should be understood that the invention can be practiced with modification and alteration, and that the disclosed technology be limited only by the claims and the equivalents thereof.

DETAILED DESCRIPTION OF THE INVENTION

The present disclosure relates to devices, systems, and methods for management and stabilization of medical tubing. In particular, various embodiments may relate to management, stabilization and/or immobilization of in-dwelling urinary catheters, suprapubic urinary catheters, ileostomy catheters, chest tubes, and the like.

Figure 17A:
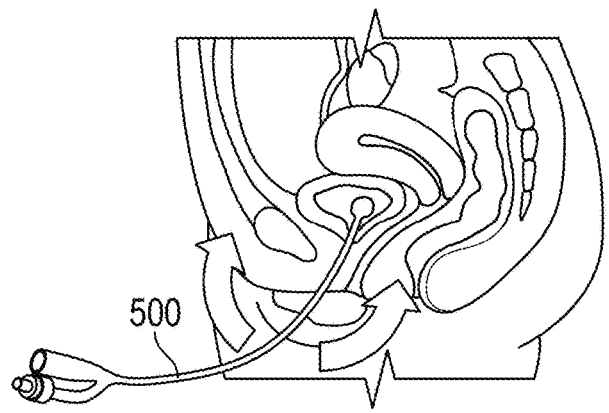
FIG. 17A-17B illustrate first and second side views of a portion of a patient's body having a catheter disposed therein, the catheter experiencing lateral movement relative to the body of the patient, according to embodiments of the present disclosure.
Figure 17B:
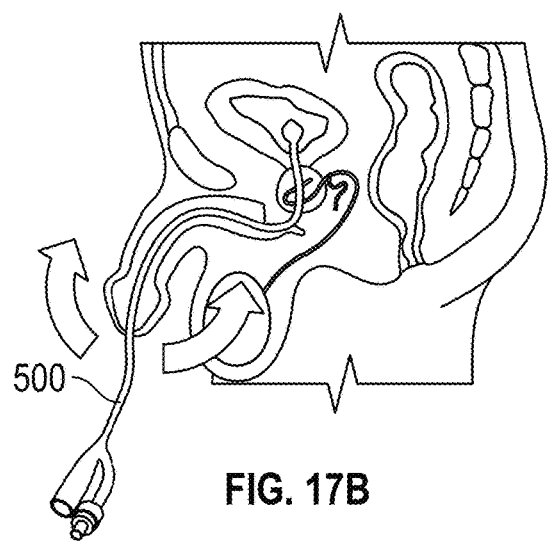
Figure 18A:
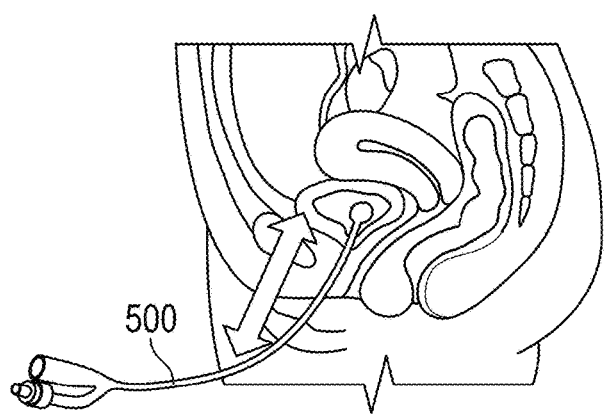
FIG. 18A-18B illustrate first and second side views of a portion of a patient's body having a catheter disposed therein, the catheter experiencing pistoning movement relative to the body of the patient, according to embodiments of the present disclosure.
Figure 18B:
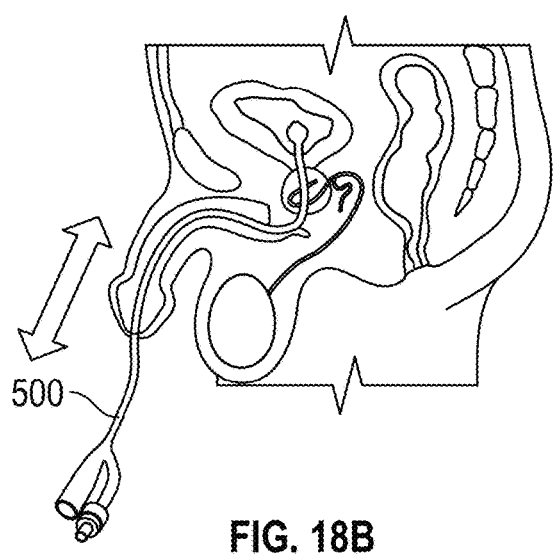
Figure 19A:
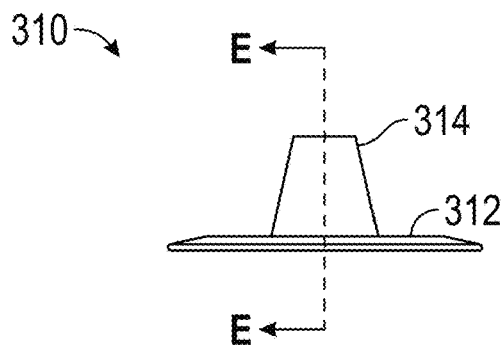
Figure 19E:
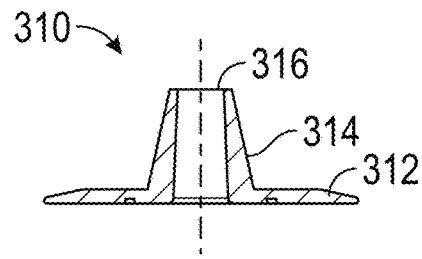
FIGS. 19E-19H illustrate respective cutaway views of the tube engaging elements of FIGS. 19A-19D, according to various embodiments of the present disclosure.
Figure 19B:
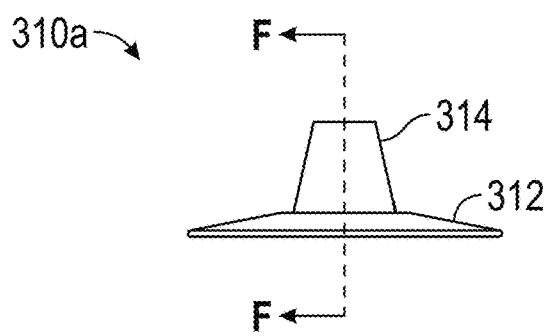
Figure 19F:
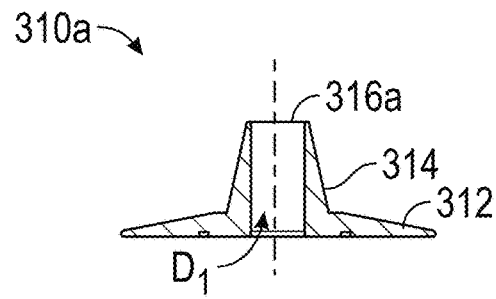
Figure 19C:
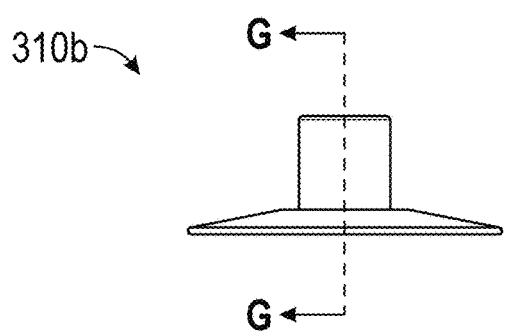
Figure 19G:
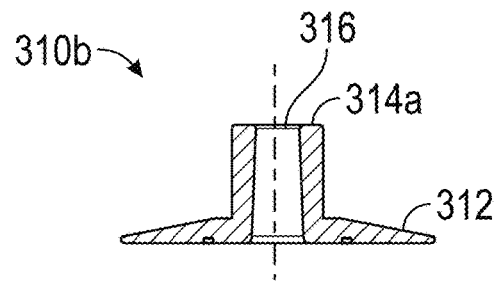
Figure 19D:
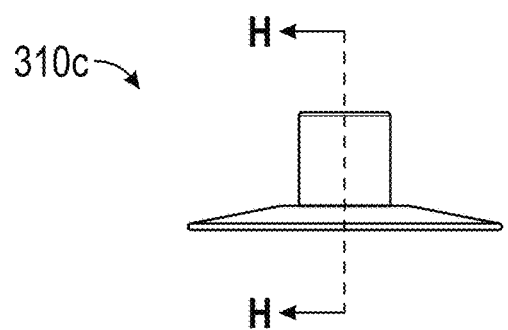
Figure 19H:
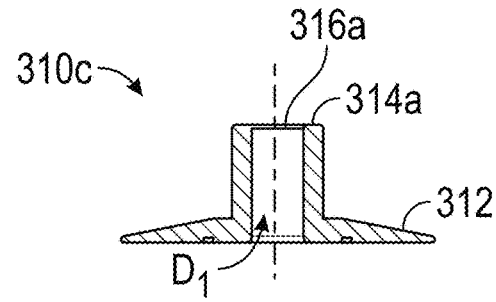
Figure 20:
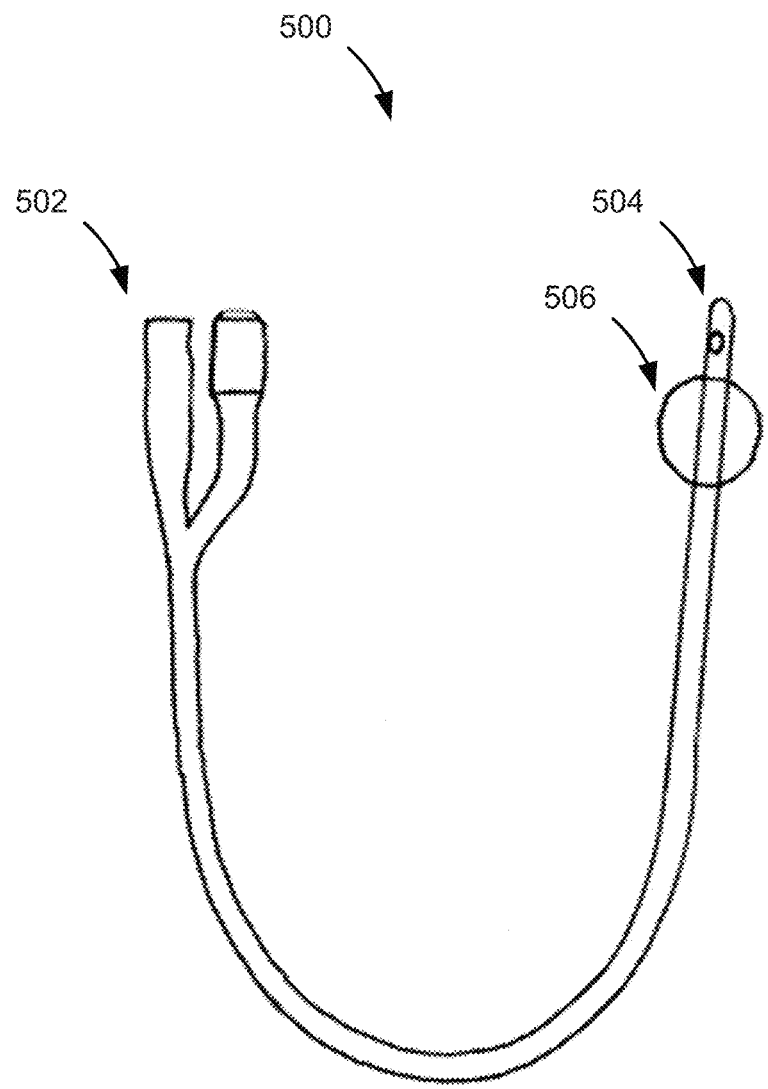
FIG. 20 illustrates a urinary catheter or medical tube, according to various embodiments of the present disclosure.

As discussed, a problem with protruding medical tubing and catheters is that they are free to move laterally around the patient insertion site or entry point on the patient, for example as shown in FIGS. 17A and 17B, or to move in and out (piston) of the patient, for example as shown in FIGS. 18A and 18B. Both motions introduce microbials and bacteria; and further move around the entry point, which may cause callusing, strain, or other tissue damage.

One way in which this problem may be solved is to provide a device and/or system that artificially stabilizes, immobilizes and supports the medical tubing and/or catheter in such a way that at least the portion of the medical tubing disposed to a patient side of the stabilization device is stabilized and immobilized from the above-described movement relative to the urethra and/or bladder of the patient. The inventor(s) of the instant invention(s) have discovered that providing continuous support, stability and immobilization for the medical tubing and/or catheter as close to the exit point of the medical tubing and/or catheter from the patient's body as possible greatly increases the effectiveness of artificial stabilization, immobilization and support that can be provided by such stabilizing devices and/or systems.

However, variation in waistline is significant between people (e.g., patients). For example, waistline may vary by 10 inches or more between potential patients. Moreover, variation in catheter exit point from the body is also significant between people, especially the variations between male and female anatomy measured with respect to, for example, a waistband of an underwear garment. For example, the male anatomy is subject to significantly greater risk and magnitude of movement of the patient's urethral opening with respect to the rest of the body and/or undergarments. Moreover, the average male urethra is 8 inches long from the urethra meatus to the bladder. In the vast majority of the population, this distance may vary by plus or minus 2 inches. Even just between males, this plus or minus 2-inch variance would be significantly easier to accurately account for if everyone's waist was the same size. As above, this is not the case, and there is significant variance in people's underwear size due to their weight (e.g., both frame size and body fat levels). Accordingly, accounting for this plus or minus 2-inch variation is significantly complicated by the unavoidable reality that waistline can vary by 10 inches or more between patients. Since one goal is to provide continuous support, stability and immobilization for the medical tubing and/or catheter as close to the exit point of the medical tubing and/or catheter from the patient's body as possible, the inventor(s) recognized a need for an alternative way of potentially defining, designing and configuring the location of a catheter exit point on such an adjustable garment.

The inventor(s) of the instant invention(s) have discovered that, while defining the urethral exit point for the medical tubing and/or catheter from the waistline down requires accounting for the body fat levels of the patient, the distance across the perinium (e.g., the patch between the anus and the scrotum in men or between the anus and the opening to the vagina) to the urethra meatus will not change significantly as the weight of the patient changes. For example, the inventor(s) have discovered that the distance across the perineum to the catheter exit point (i.e., the distance along the perineum between, or separating, the anus and the urethra meatus) for a 150 lb person will be similar to that of a 300 lb person, while the distance from the top of the waistline to the same urethra meatus point will be significantly different between the two.

Accordingly, to accommodate all different patient sizes and shapes, and actually adjustably provide this physical support, stability and immobilization for the medical tubing and/or catheter as close as practical to the actual exit point of the medical tubing or catheter from each patient's body, embodiments disclosed herein may include a combination of a tube stabilization patch and an adjustable, form fitting undergarment that is specifically configured for particular alignments with specific aspects of the patient's anatomy (e.g., the patient's anus, perineum and/or urethral opening).

The adjustable, form-fitting garment, through a combination of features, is uniquely capable of providing a base of continuous, snug, and form-fitting support as an undergarment or "underwear" by providing continuous, direct physical contact and substantially evenly applied support between all, or substantially all, immediate patient-facing surfaces of the garment and immediately facing portions of the patient's waist, hips, buttocks, perineum, genital, and/or lower abdominal areas. Such a form fitting adjustable undergarment reduces or substantially eliminates relative motion between the patient's body and the adjustable undergarment. From this stationary base, and employing a unique combination of features described in more detail below, specific portions of the garment are also specifically designed and configured to adjustably and affirmatively align with particular aspects of the patient's anatomy (e.g., the patient's anus, perineum and/or urethra meatus), or to have predetermined dimensions based thereon, in a novel and non-obvious way that enables an adjustable securing mechanism, or aggregated catheter exit port, of the adjustable garment to actually be disposed as close as possible to (e.g., immediately opposite) the actual exit point of the medical tubing and/or catheter from each patient's body, regardless of waistline or body size.

Such systems may also include a tube stabilization patch configured to be removably coupled to and/or having at least a portion configured to pass through the adjustable, form-fitting garment. As will be described in more detail below, the tube stabilization patch comprises special features configured to physically stabilize and prevent relative motion of medical tubing and/or a catheter disposed therein with direct physical contact having a substantially equal pressure about an entire perimeter of the medical tubing, substantially equal pressure that is actually incapable of closing off, or even physically deforming the catheter lumen, by accident or intention.

An aim of embodiments described anywhere in the present disclosure is to provide a novel and non-obvious solution to one or more of the above-described problems while simultaneously providing one or more, and in many cases all, of the following advantages.

A first advantage of medical tubing stabilization devices or systems described herein is the ability to substantially prevent or eliminate relative motion between the catheter and the patient's body, especially relative motion between the urethra and/or bladder and all portions of the catheter on the proximal, human body side of the stabilization device and/or system, even and especially while the patient is fully ambulatory and such ambulation directly magnifies and drives the potential for such relative motion. Substantial prevention or elimination of such relative motion, utilizing any embodiment or portion thereof as described anywhere in this disclosure, prevents at least (1) pistoning motion of the catheter with respect to the urethra and/or bladder of the patient and/or bladder contusions caused by an unsecured end poking into the bladder wall, see for example FIGS. 18A and 18B, and (2) lateral motion of the catheter about the catheter's longitudinal axis to, thereby, prevent erosion caused by uneven pressure against the side of the urethra and/or bladder contusions caused by unsecured proximal end or portion of the catheter rubbing or scraping against the bladder wall, see for example FIGS. 17A and 17B.

A second advantage of medical tubing stabilization devices or systems described herein is that the novel and inventive way in which the medical tubing is physically stabilized with direct physical contact having a substantially equal pressure about an entire perimeter of the medical tubing. The nature of this pressure actually being incapable of closing off, or even physically deforming whatsoever, the catheter lumen, by accident or intention. The medical tubing or catheter has a natural rigidity due to its material properties. It is manufactured, either dip molded or injection molded, in a straight (unbent) orientation and, therefore, its natural unstressed condition is this straight (e.g., unbent) orientation. As previously described, when securing the external, proximal end of the catheter to the patient's leg, extra slack must be provided in the form of a bend in the catheter tubing. This necessary bend, exerts a pressure on the urethral tissue, due to the natural rigidity of the catheter. With only a leg securement device 510 in use, as the leg moves, the catheter will necessarily move with the leg, and this motion will translate to the internal tissues of the body, exerting forces on the urethra and bladder tissue. These forces are exerted, or propagated, through the catheter material because that material has the above-mentioned natural rigidity. If the catheter were perfectly flexible (i.e., having zero rigidity), it would not be able to transfer, or propagate, the forces to the urethra or bladder. Accordingly, it essentially this small amount of rigidity, plus a factor of safety, that must be overcome in order to stabilize the catheter in a way that dampens or eliminates the forces translating to the body. Because the force required to damage, deform or pinch off the catheter is substantially higher than the force required to overcome the rigidity of the catheter, tube engaging element 310 is, therefore, able to grip the medical tubing or catheter with enough force, and friction, to stabilize the catheter appropriately, while simultaneously posing no risk of damaging, deforming or pinching off the medical tubing or catheter lumen(s).

This advantage is in direct contrast to any prior solutions that utilize clamps, clamping elements, discrete multi-point gripping elements, ratcheting features, or any element(s) that, alone or collectively when combined with any other features, would act to pinch or otherwise secure the catheter by applying force to the catheter walls in any uneven manner. e.g., any way other than with direct physical contact having substantially equal pressure about an entire, or substantially entire, perimeter of the medical lubing. This advantage is also in direct contrast to any prior solutions that utilize "slits" or, similarly, "slots" to direct catheter tubes through a garment at least because such "slits," or similarly "slots," do not and cannot physically stabilize the medical tubing with direct physical contact having a substantially equal pressure about an entire perimeter of the medical tubing. Rather, such "slits," or similarly "slots," achieve adjustability in a completely different, and diametrically opposite, way from the present invention(s), by disallowing direct physical contact having a substantially equal pressure about an entire perimeter of the medical tubing so that catheter tubing may be unsupported or incompletely supported at any of a plurality of locations within the "slit" or, similarly, "slots." In such prior art designs, such prior "slits" or "slots" may have been considered suitable where the application was immobilized patients. However, such "slits" or "slots" cannot be considered suitable where the application is fully mobile patients. In fact, as such "slits" or "slots" increase in size to accommodate the increasing variations in body size, they unavoidably become large enough to no longer be capable of reliably maintaining the male genital anatomy within the supportive garment, especially during ambulation. However, the present disclosure is not so limited and is, in fact, directed for use by both immobilized patients as well as fully mobile patients. Accordingly, in contrast to such prior slitted or slotted designs that merely guide medical tubing passing therethrough, the novel and inventive way in which the medical tubing is physically stabilized at an underside and around the sides of the medical tubing by adjustable flaps 121, 122 and their joining vertex 123, and simultaneously physically stabilized at a top and upper side portions of the medical tubing by a hinged flap 124, is uniquely suited to provide the described advantages tor fully mobile patients, where such mobility is sure to present increased tendency for undesirable catheter motion relative to the body (e.g., urethra and/or bladder) of the patient, as well as increased risk of unintended and embarrassing male anatomy exposure.

A third advantage of medical tubing stabilization devices or systems described herein is that the novel and inventive way in which the medical tubing is physically stabilized is specifically configured to accommodate a full range of catheter sizes. Specifically, the novel and inventive way in which the medical tubing is physically stabilized is designed to automatically adjust itself to fit tightly and snuggly around, in direct physical contact with, an uninterrupted perimeter of the medical tubing. In some embodiments, the uninterrupted perimeter of the medical tubing comprises substantially the entire perimeter of the medical tubing (e.g., 90% or more of the entire perimeter, or 95% or more of the entire perimeter). In some embodiments, the uninterrupted perimeter of the medical tubing comprises the entire perimeter of the medical tubing.

A fourth advantage of the medical tubing stabilization devices or systems described herein is that they are fully adjustable to accommodate both male and female anatomies as well as the varying sizes of both male and female bodies, while simultaneously achieving each of the previously described first, second and third advantages, as well as the fifth advantage described below. Moreover, the medical tubing stabilization devices or systems described herein achieve this fourth advantage despite male and female anatomies varying greatly, especially with respect to urethra length and relative opening location, and also despite waist size varying by more than 10 inches between individuals.

A fifth advantage of the medical tubing stabilization devices or systems described herein is that the medical tubing stabilization devices or systems may be easily donned and/or removed from the patient without any adjustment or removal of a properly installed catheter from the urethra of the patient and without any adjustment or disconnection of the catheter, drainage tube, drainage tube connections, drainage bag, or any auxiliary securement device for securing a portion of the catheter to, for example, the leg of the patient.

Medical tubing stabilization devices or systems described herein may simultaneously achieve all five of the above-described advantages through its combination of fully adjustable garment and disposable catheter securing patch design(s), as will be described in more detail anywhere in this disclosure.

In contrast to prior solutions that merely treat the symptoms of such CAUTIs, the present disclosure provides a simple and reliable solution that increases patient trust-a medical tubing stabilization device that adjusts to all body sizes and orientations and that is specifically designed to eliminate the cause of the above-mentioned CAUTIs, bladder spasms, and/or pressure sores.

As stated above, the provided medical tubing stabilization device may include an adjustable medical garment 100 and a tube stabilization patch 300. While garment 100 and tube stabilization patch 300 are both described in more detail below in connection with one or more figures, a brief description immediately follows, below.

The adjustable medical garment 100 may be washable and reusable, while the lube stabilization patch 300 may be disposable after a single use (e.g., after a desired and/or appropriate uninterrupted period of time attached to medical tubing, a catheter, garment 100, and/or the patient's body). Tube stabilization patch 300 may include a tube engaging element 310 that holds the tube in place and a patient attachment element 320 connected to the periphery or perimeter of tube engaging element 310, which attaches tube stabilization patch 300 to the patient.

Tube stabilization patch 300 reduces the amount of relative movement of the medical tubing or catheter by providing an additional structural component (e.g., tube engagement element 310) that is disposed in direct physical contact with an uninterrupted perimeter of the medical tubing or catheter, in some cases and/or embodiments, in direct physical contact with substantially the entire uninterrupted perimeter of the medical tubing or catheter. This direct physical contact is specifically designed to provide substantially equal pressure about the entire perimeter of the medical tubing. This direct physical contact is also specifically designed such that this substantially equal pressure developed thereby is simultaneously incapable of closing off, or even physically deforming, the catheter lumen, by accident or intention. Such a structure (i.e., tube engaging element 310) may be designed and/or manufactured to have a higher rigidity than do conventional medical tubing or catheters in order to reduce or restrict the amount of free lateral movement the catheter can engage in. Additionally, the tube engaging element may stabilize and/or secure the medical tubing or catheter, such that the medical tubing or catheter movement in and out of the patient (i.e., "pistoning") is significantly reduced and, in some embodiments, substantially eliminated. By reducing and/or eliminating the pistoning effect, less bacteria and microbials are introduced into the interior of the patient's body, resulting in fewer instances of CAUTI. Additionally, due to the decreased lateral movement, the patient may experience reduced levels of strain on the entry point of the medical tubing or catheter. As a result, reduced piston effect and reduced lateral movement reduce the amount of medical tubing or catheter movement internal to the patient, which prevents tissue damage and other irritation. The tube stabilization patch may be made from single-use or disposable materials and may be provided to patients in a sterile and/or sealed container to further reduce the risk of possible exposure to bacteria and microbials.

Patient attachment element 320 may be configured for removable attachment to a region of skin on a patient, to an external surface of adjustable medical garment 100, or to an internal, patient-facing surface of adjustable medical garment 100 (as discussed anywhere herein). Since patient attachment element 320 is connected to the periphery of tube engaging element 310, a patient can easily remove tube stabilization patch 300 by pulling on patient attachment element 320. In some embodiments, a pull lab 360 may be included on patient attachment element 320 to further ease the patient's removal of tube stabilization patch 300.

In embodiments, once the medical tubing, or for example, an in-dwelling urinary catheter, is positioned in the patient, the tube engaging element may be attached around the tubing or catheter by, for example, slipping tube engaging element 310 around the medical tubing at a location immediately adjacent, opposite and/or proximate where the tubing exits the patient's body (e.g., immediately adjacent, opposite and/or proximate the urethra meatus of the patient where a foley catheter is utilized, or proximate the suprapubic exit point of the tubing from the patient's body). When tube engaging element 310 of tube stabilization patch 300 is releasably attached to the medical tubing or catheter, tube stabilization patch 300 can control, i.e., prevent or reduce, the relative movement of the medical tubing in relation to the stabilization device, especially relatively movement of the portion of the medical tubing disposed between the stabilization device and the patient.

Tube stabilization patch 300 may be further secured with adjustable medical garment or undergarment 100. Adjustable medical garment 100 may include a body portion 105 that wraps around the patient and an adjustable front flap portion 120 that secures to an anterior section of body portion 105. The adjustable front flap portion 120 may include, or form at least a portion of, the above-mentioned securing mechanism that may allow for the medical tubing or catheter to pass therethrough without the medical tubing or catheter having to be removed or disconnected from the patient. As will be described in more detail below, in embodiments where patch 300 is adhered to an inside, patient-facing surface of garment 100, at least a portion of the securing mechanism may be secured around the tube engaging element, further increasing the stabilization of the catheter. By combining the stabilization effect provided by particular features of tube stabilization patch 300 and the separate, but complementary, stabilization effect provided by particular features of adjustable medical garment 100, the lateral movement and piston effect often experienced by patients, may be decreased.

Additionally, or alternatively, adjustable medical garment 100 may be secured onto the patient and tube stabilization patch 300 may then be secured around the medical tubing and secured to an external surface of the medical garment. This may provide a similar dampening effect as attaching tube stabilization patch 300 directly to the patient or beneath the medical garment but may allow for the patch to be more easily changed. In other words, tube stabilization patch 300 may be disposed between the body of the patient and adjustable medical garment 100 (i.e., body-patch-garment) or adjustable medical garment 100 may be disposed between the body of the patient and tube stabilization patch 300 (i.e., body-garment-patch).

Figure 1A:
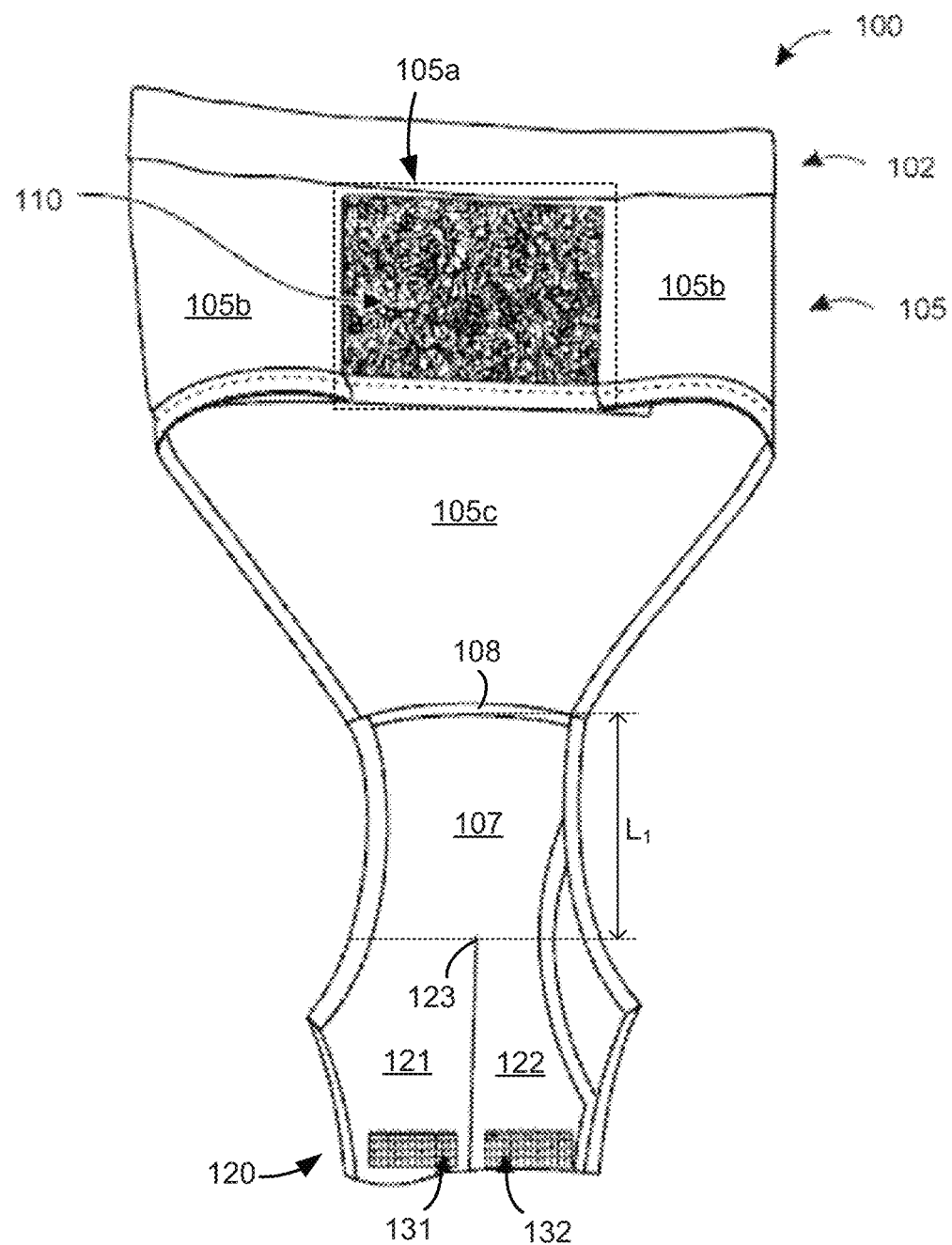
FIG. 1A is a front view of an example medical garment of a device or system for stabilizing medical tubing protruding from a patient with adjustable flaps in unattached positions, according to embodiments of the present disclosure.

The description now turns to the figures. FIG. 1A is a front view of an example adjustable medical garment 100 of a device or system for stabilizing medical tubing protruding from a patient with an adjustable front flap portion 120 in an unattached position, according to embodiments of the present disclosure.

According to various embodiments of the present disclosure, the medical garment 100 may include an encircling waistband 102 and an encircling body portion 105. Waistband 102 may comprise an elastic material such that it is configured to fit snuggly directly against an entire, uninterrupted perimeter of the patient's waist. Accordingly, in some embodiments, adjustable undergarment 100 is manufactured in one of a plurality of discrete sizes (e.g., extra-small, small, medium, large, extra-large, or any subset or larger set including any subset thereof). In some embodiments, waistband 102 comprises a textured inner, patient-facing surface configured to increase comfort. In some embodiments, waistband 102 comprises a textured inner, patient-facing surface configured to increase to increase grip between waistband and the patient's skin. In at least this way, waistband 102 is configured to reduce or substantially eliminate vertical shifting of the entire undergarment 100. Accordingly, at least in this way, waistband 102 is similarly configured to reduce or substantially eliminate rotational shifting of the entire undergarment 100 with respect to the body of an ambulating patient disposed therein.

The encircling body portion 105 is configured to encircle and be in continuous, direct physical contact with the hips, waist, lower abdominal region, and buttocks of the patient below waistband 102. In some such embodiments, encircling body portion 105 may be configured to encircle and be in direct physical contact with an entire uninterrupted perimeter of the patient along each of the hips, waist, lower abdominal region, and buttocks of the patient below waistband 102. Accordingly, encircling body portion 105 may be sewn to waistband 102 along the entire perimeter of waistband 102. In some embodiments, encircling body portion 105 may comprise a breathable fabric material, in some such embodiments comprising a stretchy material such as nylon, Rayon™ or Spandex™.

As will be described below, such a conformal lightweight, non-bulky configuration ensures garment 100 does not drag on medical tubing, catheters or the anatomy of the patient. The conformal fit about varying body surfaces (e.g., the genitals) is important to maintaining an anatomically neutral catheter exit location (e.g., a location and orientation that minimizes or substantially eliminates uneven pressure from the medical tubing or catheter against one side or direction of the urethral opening) while the patient moves and is a prerequisite for the ability to immobilize and support medical tubing or a catheter extending from the patient's body. And the light-weight nature is required, or relative movement will occur under the influence of gravity while walking and/or standing. Extra weight and bulkiness applies undesirable external pressure to clothes and potentially transfers that pressure onto body parts and causes compression injury (e.g., ulceration). Accordingly, a bulky garment would preclude the ability to comfortably wear form fitting pants without causing such increased compression from the garment having to fit between the patient's body and pants. Encircling body portion 105 may include a rear, or buttocks, portion 105c configured to cover a dorsal area below the waistband 102 along with a patient's buttocks region. Each side 105b of the rear, or buttocks, portion is configured to extend and conformally wrap around the side, waist and hip of the patient to form a front, or lower abdominal portion 105a of body portion 105 that is configured to be disposed in direct physical contact with the lower abdomen region of the patient above the genital area of the patient.

In some embodiments, a most distal edge of the rear, or buttocks, portion of body portion 105 is sewn or otherwise bonded to a perineal portion 107 to form a seam 108. In some embodiments, garment 100 is specifically designed such that seam 108 extends in a medial-lateral direction, substantially parallel to the frontal plane of the body, and is configured to be aligned with the perineum, and in some embodiments the anus, of the patient when garment 100 is properly donned by the patient. Specifically, in some embodiments, seam 108 is configured to be disposed directly vertically under, and in some cases precisely aligned along a diameter of, the anus 700 of the patient when garment 100 is properly donned by the patient and the patient is standing (see, e.g., FIG. 1C, in which a portion of a patient's body is illustrated, in cross section with an embodiment of garment 100 aligned thereon such that seam 108 is disposed substantially vertically aligned with the perineum, and in some cases anus 700, of the patient). As will be described in more detail below, this alignment of seam 108 directly under the perineum, and in some embodiments the anus, of the patient may be important, in some embodiments, since, as described above, inventors have discovered that the distance across the perinium to the urethra meatus does not change significantly with weight of the patient. Accordingly, such a deliberate configuration for such a deliberate vertical alignment between seam 108 and the perineum, and in some embodiments the anus 700, of the patient allows particular features of perineal portion 107 to have a pre-configured size, or separation, and to be adjusted to align with the expected exit point of the medical tubing or catheter from the patient's body (e.g., align with the meatus of the urethra of the patient).

Perineal portion 107 is configured to extend from seam 108 under and across the entire perinium of the patient (e.g., the patch between anus 700 and the scrotum or between anus 700 and the opening to the vagina, depending upon patient gender). Accordingly, form-fitting perineal portion 107 is configured to be in direct physical contact with at least a portion of the perinium of the patient when garment 100 is properly donned by the patient. Moreover, in some embodiments, form-fitting perineal portion 107 is configured to be the only portion of adjustable garment 100 in direct physical contact with or covering the perinium of the patient when garment 100 is properly donned by the patient.

Perineal portion 107 extends from seam 108 to become, or is connected via seams directly to, an adjustable front flap portion 120. The body portion 105, perineal portion 107, and adjustable front flap portion 120 may be connected by non-partable or partable seams (e.g., including seam 108 as previously described), or may further be connected by structure. For example, the body portion 105, perineal portion 107, and adjustable front flap portion 120 may be cut from a singular piece of fabric and thus connected by the structure of the fabric, some such embodiments still comprising an embroidered seam 108 as described above for use as a visual or tactile indicator for proper alignment of adjustable garment 100 with the body of the patient.

Figure 1B:
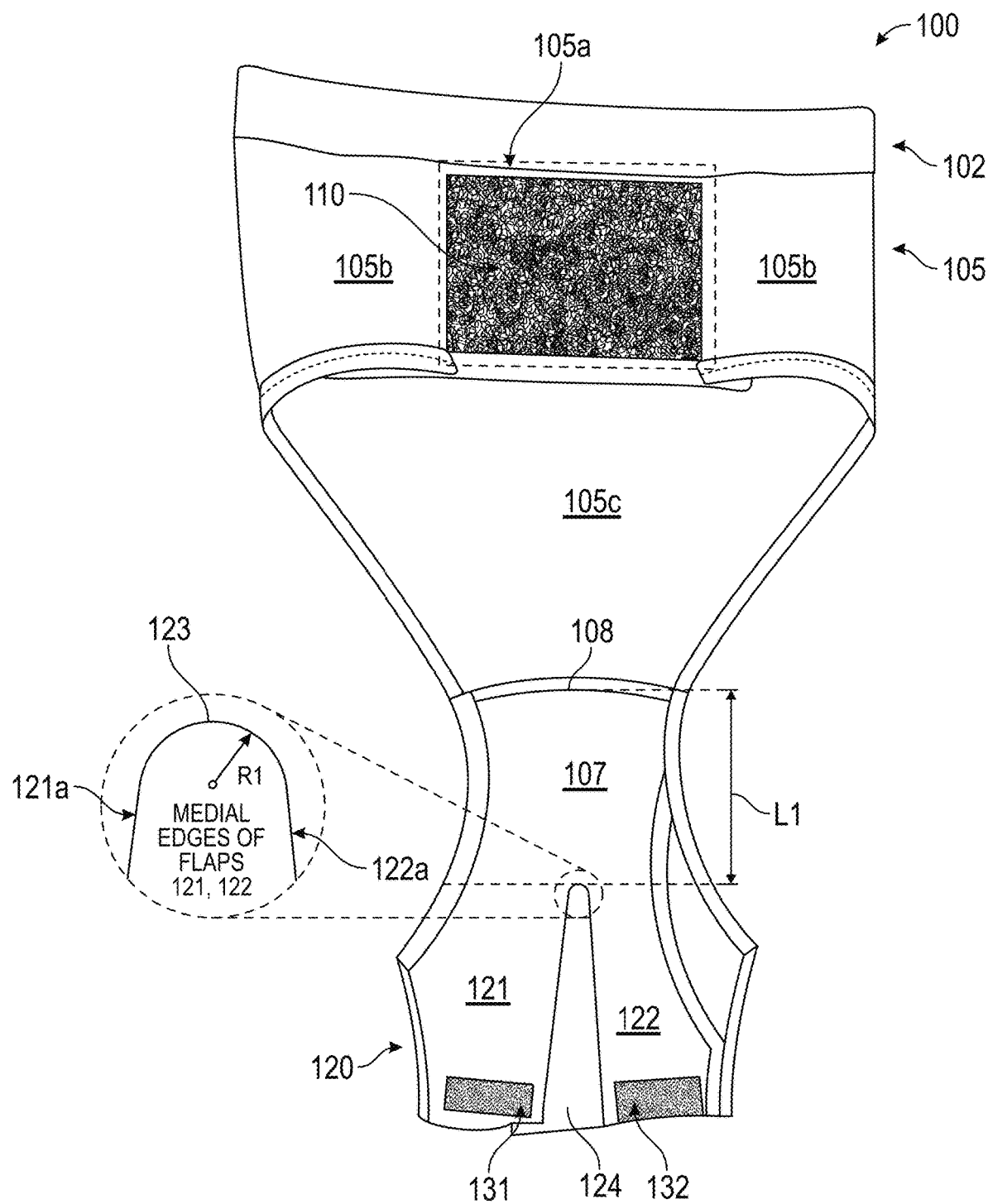
FIG. 1B is a front view of another example medical garment of a device or system for stabilizing medical tubing protruding from a patient with adjustable flaps in unattached positions, according to embodiments of the present disclosure.
Figure 1C:
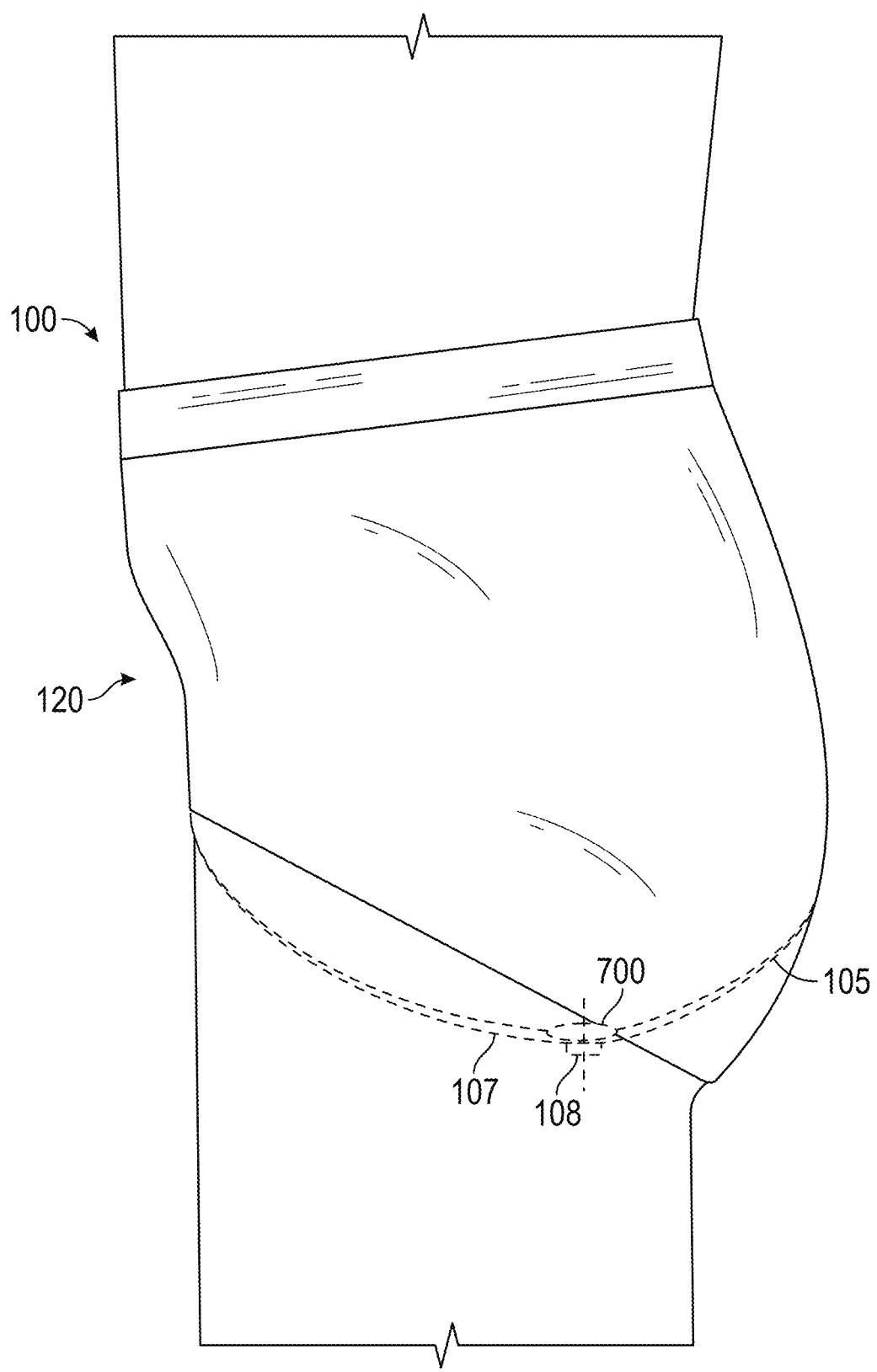
FIG. 1C is a side cutaway view of a patient wearing a medical garment of a device or system for stabilizing medical tubing protruding from a patient, according to embodiments of the present disclosure.

As shown in FIGS. 1A and 1B, a most proximal end of body portion 105 is sewn or otherwise coupled to waist band 102 and extends down the buttocks to become, or to be coupled to, perineal portion 107 at seam 108. Perineal portion 107 extends from seam 108 across or under a perineum of the patient to a location, point, or vertex, 123 where a first adjustable flap 121 meets a second adjustable flap 122. Accordingly, in some such embodiments, one end of perineal portion 107 is defined by seam 108, and the other most distant end, or extent, of perineal portion 107 is defined by vertex 123. Vertex 123 is also the exact location at which the medical tubing or catheter is configured to pass from the inside of adjustable garment 100 to the outside of adjustable garment 100.

Accordingly, a length $L_1$ of perineal portion 107 (e.g., a straight line distance along the fabric from seam 108 to vertex 123 from which first and second adjustable flaps 121, 122 of a front adjustable flap portion 120 of garment 100 extend) may be deliberately set at a value the inventors have discovered corresponds to the minimally variable distance between the anus and urethral meatus for particular ranges of body size (e.g., the length $L_1$ may be between 2 inches and 6 inches long to account for men, women, children and/or the obese, for example, in some embodiments, a "small" sized garment 100 may be manufactured so that the length $L_1$ of perineal portion 107 is approximately, or exactly, 4 inches, while a "large" sized garment 100 may be manufactured so that the length $L_1$ of perineal portion 107 is approximately, or exactly, 4.5 inches). Accordingly, as will be described in more detail below, garment 100 may be specifically designed and manufactured to provide a neutral orientational fit, wherein at least the location of vertex 123 relative to, for example, the waistband 102 and/or body portion 105 of garment 100 is adjustable, by up to several inches in the vertical and/or horizontal direction.

From vertex 123, and continuing in the same direction as from body portion 105 to seam 108 to perineal portion 107, is defined as adjustable front flap portion 120, which is configured to extend beneath the crotch area of the patient and wrap around to adjustably couple with an upper abdominal portion 105*a* of body portion 105 of adjustable garment 100. Adjustable flap portion 120 may be configured to cover an anterior area of the patient's abdomen below the waistband 102 when it's adjustable flaps are properly secured to an anterior area of body portion 105 just inferior of the waistband 102. Adjustable flap portion 120 may be unattached from the body portion 105, as depicted, for example, in FIG. 1A or 18, attached, as depicted, for example, in FIG. 2, or partially attached as depicted, for example, in FIG. 4.

Adjustable front flap portion 120 comprises a first adjustable flap 121 extending from the most distal edge of perineal portion 107 such that a medial edge 121*a* of first adjustable flap 121 is to a first lateral side of vertex 123. Adjustable front flap portion 120 also comprises a second adjustable flap 122 extending from the most distal edge of perineal portion 107 such that a medial edge 122*a* of second adjustable flap 122 is to a second lateral side of vertex 123 opposite the first lateral side.

In some embodiments, see, e.g., FIG. 1A, vertex 123 may comprise a substantially angled point at which opposing straight medial edges of first and second adjustable flaps 121, 122 meet. Accordingly, in some such embodiments, first and second adjustable flaps 121, 122 may be created by forming a split from a center point of the most distal edge of adjustable flap portion 120 toward seam 108 until reaching vertex 123, see, e.g., FIG. 1A. However, the present disclosure is not so limited and, in some embodiments, see. e.g., FIG. 1B, first and second adjustable flaps 121, 122 may alternatively be created such that vertex 123, instead of comprising the angled point above, and in the relaxed state without medical tubing touching, comprises a curved edge having a minimum radius of curvature $R_1$ that then extends to form the opposing straight medial edges of first and second adjustable flaps 121, 122. In some embodiments, $R_1$ is approximately equal to the radius of the medical tubing or catheter(s) adjustable garment 100 is configured to secure, e.g., in some embodiments, at least a 2 mm radius, or at least a 3 mm radius.

Embodiments where vertex 123 comprises such a specifically sized curved edge that then extends to form the opposing medial edges of first and second adjustable flaps 121, 122 provide an advantage over angled point vertexes at least in that, as the medial edges of first and second adjustable flaps 121, 122 are secured around the medical tubing or catheter (as will be described in more detail below), the curved edge having the minimum radius of curvature $R_1$ approximately equal to the radius of the accommodated medical tubing or catheter ensures that the medial edges 121*a*, 122*a* of first and second adjustable flaps 121, 122 immediately extending from the curved edge of vertex 123 always extend in a direction that is substantially tangential to the outer perimeter of the medical tubing or catheter (or of the outer perimeter of the portion of tube stabilization patch 300) around which those medial edges are secured. This enables substantially equal pressure about the entire perimeter of the medical tubing (or around the outer perimeter of the tube holding portion 310 of tube stabilization patch 300) around which those medial edges are secured that is also incapable of closing off, or even physically deforming, the catheter lumen, by accident or intention.

By contrast, were medial edges 121*a*, 122*a* of first and second adjustable flaps 121, 122 configured to extend in a straight line away from an angled point vertex 123, the medial edges of first and second adjustable flaps 121, 122 immediately extending from an angled point vertex initially extend in a direction that is not substantially tangential to the outer perimeter of the medical tubing or catheter (or of the outer perimeter of the portion of tube stabilization patch 300) around which those medial edges are secured. Accordingly, substantially no pressure is exerted at the immediately closest point of the perimeter of the medical tubing or catheter to the angled point vertex 123 and, accordingly, an increased amount of pressure is exerted normal to the surface of the medical tubing (or around the outer perimeter of the portion of tube stabilization patch 300) at the lateral points at which the medial edges 121*a*, 122*a* of first and second adjustable flaps 121, 122 first contact the medical tubing (or the outer perimeter of the portion of tube stabilization patch 300). This uneven application of pressure can undesirably close off, or at least undesirably physically deform and, thereby, partially occlude the catheter lumen.

To attach the first and second flaps 121, 122 to body portion 105, an attachment mechanism is provided between each of first and second flaps 121, 122 and the anterior area of body portion 105 just inferior of the waistband 102. Such an attachment mechanism may include a first attachment portion 110 centrally disposed on the anterior area of an outwardly facing surface of body portion 105 just below, or inferior, of waistband 102, a second attachment portion 131 disposed at a distal end of an inward, or patient-facing, surface of first flap 121, and a third attachment portion 132 disposed at a distal end of an inward, or patient-facing, surface of second flap 122.

In various embodiments, medical tubing or a catheter is configured to exit the body of the patient and then exit garment 100 through a catheter exit point 210 (see FIG. 3) that is ultimately formed at, and including, vertex 123. Accordingly, a location of vertex 123, and so of this catheter exit point 210, with respect to the patient's body and other portions of garment 100, may be adjusted by attaching the second attachment portion 131 to an appropriate first position on first attachment portion 110 and attaching third attachment portion 132 to an appropriate second position on first attachment portion 110. Generally, the first and second positions may be substantially immediately beside one another to ensure the medial edges 121*a*, 122*a* of first and second adjustable flaps 121,122 are substantially immediately facing or touching one another, or the second position slightly overlapping the first position to ensure the medial edges 121*a*, 122*a* of first and second adjustable flaps 121, 122 overlap one another immediately superior to (or above) the medical tubing or catheter extending therethrough. However, the present disclosure is not so limited and these first and second positions may be any suitable respective positions on first attachment portion 110.

First, second and third attachment portions 110, 131, 132 may, for example, attach to each other via a conventional hook and loop method (e.g., Velcro brand), reusable adhesive, and/or any other suitable method for repeatably attaching fabrics to one another. For example, first attachment portion 110 may comprise one of hook or loop fasteners while each of second and third attachment portions 131, 132 may comprise the other of the hook or loop fasteners. Accordingly, second attachment portion 131 is configured to adjustably couple with first attachment portion 110 but not with third attachment portion 132. Similarly, third attachment portion 132 is configured to adjustably couple with first attachment portion 110 but not with second attachment portion 131. This prevents first, second and third attachment portions 110, 131, 132 from accidentally and/or undesirably coupling with the wrong portions of garment 100 and the attendant readjustment discomfort. However, the present disclosure is not so limited and first, second and third attachment portions 110, 131, 132 may each comprise the appropriate one of a first type of fastener or first portion of an adjustable fastener assembly, or a second type of fastener or second portion of the adjustable fastener assembly wherein the first type of fastener or first portion of the adjustable fastener assembly is configured to mate with the second type of fastener or second portion of the adjustable fastener assembly but not another first type of fastener or first portion of the adjustable fastener assembly, and wherein the second type of fastener or second portion of the adjustable fastener assembly is configured to mate with the first type of fastener or first portion of the adjustable fastener assembly but not another second type of fastener or second portion of the adjustable fastener assembly, such that second attachment portion 131 is configured to adjustably couple with first attachment portion 110 but not with third attachment portion 132 and, similarly, third attachment portion 132 is configured to adjustably couple with first attachment portion 110 but not with second attachment portion 131.

Since both second and third attachment portions 131, 132 are configured to be adjustably attached to sufficiently variable locations on first attachment portion 110 to locate vertex 123, and so the catheter exit point, immediately opposite and adjacent the location where the catheter exits the body of the patient, first attachment portion 110 may have a height and a width sufficient to allow for each of first and second flaps 121, 122 to be attached at any of a near-infinite number of analog (or infinitely granular) positions on first attachment portion 110, which allows garment 100 to be adjusted to account for varying patient anatomy and the greatest level of comfort. For example, in some embodiments the width of first attachment portion 110 may be the same as its height (e.g., a square 4-5 inches tall by 4-5 inches wide). In other embodiments, the width is less than the height. For example, first attachment portion 110 may be substantially rectangular, 5 inches tall and 4 inches wide. In yet other embodiments, the width is greater than the height. For example, first attachment portion 110 may be 4 inches tall and 5 inches wide.

Second attachment portion 131 may also have an appropriate width and height. In some embodiments, this height may exceed this width, e.g., substantially rectangular, approximately 2 inches tall and 1 inch wide. In other embodiments, this width may exceed this height, e.g., substantially rectangular, approximately 1 inch tall and 2 inches wide. In further embodiments, the width and height may be the same, e.g., substantially square approximately 1-2 inches tall and wide. Likewise, third attachment portion 132 may be similarly or identically sized.

When adjustable flaps 121,122 are in unattached positions, for example as shown by FIG. 1A or 1B, the bottom of garment 100 is open and may allow easier access for a patient to don the medical garment, as it can be slid over a catheter without disrupting the catheter position by having to maneuver legs of the patient into fixed leg holes, as would be required by conventional garments. Once body portion 105 of garment 100 is around the patient's abdomen, adjustable flaps 121, 122 can be attached, via first, second and third attachment portions 110, 131, 132, to body portion 105 of adjustable garment 100, see, e.g., FIG. 9.

Figure 2:
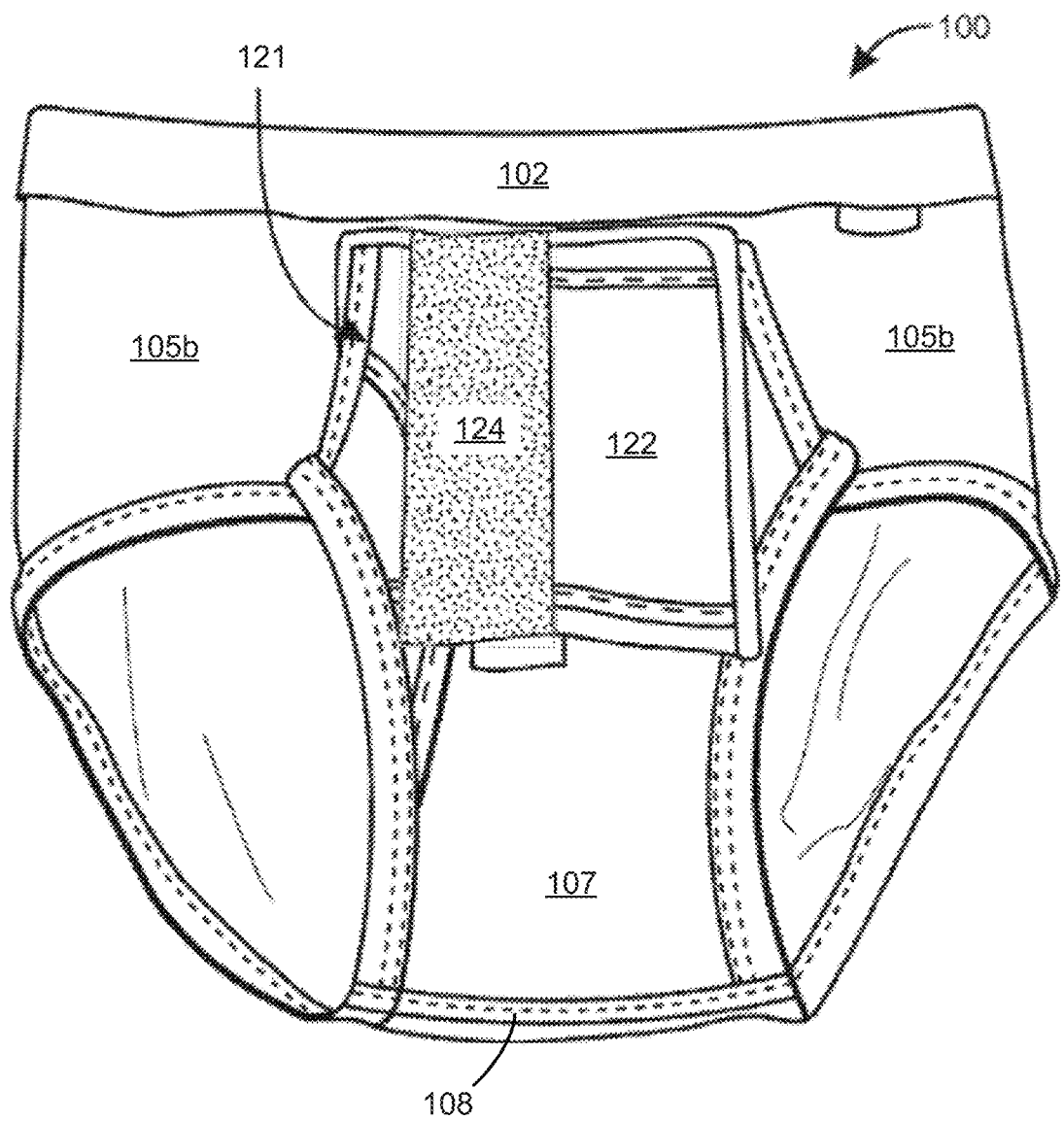
FIG. 2 is a front view of an example medical garment of a device or system for stabilizing medical tubing protruding from a patient with adjustable flaps in attached positions, according to embodiments of the present disclosure.

Referring to FIG. 2, this figure depicts a front view of an example medical garment of a device or system for stabilizing medical tubing protruding from a patient with adjustable flaps 121, 122 in example attached positions, according to embodiments of the present disclosure. For example, FIG. 2 may illustrate garment 100 of either of FIG. 1A or 1B with adjustable flaps 121, 122 in example respective first and second attached positions on first attachment portion 110 of body portion 105.

When first and second flaps 121, 122 are properly coupled to first attachment portion 110, left and right leg holes are defined. Specifically, one leg hole is defined by the lateralmost edges of one side of body portion 105, perineal portion 107 and first flap 121, which together form a first closed loop, while the other leg hole is defined by the lateral most edges of the other side of body portion 105, perineal portion 107 and second flap 122, which together form a second closed loop. As adjustment is made to attachment positions of first and second flaps 121, 122 to first attachment portion 110 on body portion 105 of garment 100, the size of the leg holes may change slightly as the desired and appropriate location of vertex 123 is achieved with respect to the exit location of the medical tubing or catheter from the patient's body. However, the overall size of garment 100 remains substantially the same. For example, in some embodiments, the overall fit and conformity of garment 100 follow from the waist being snug, elastic and fairly stationary relative to the body of the patient.

Figure 3:
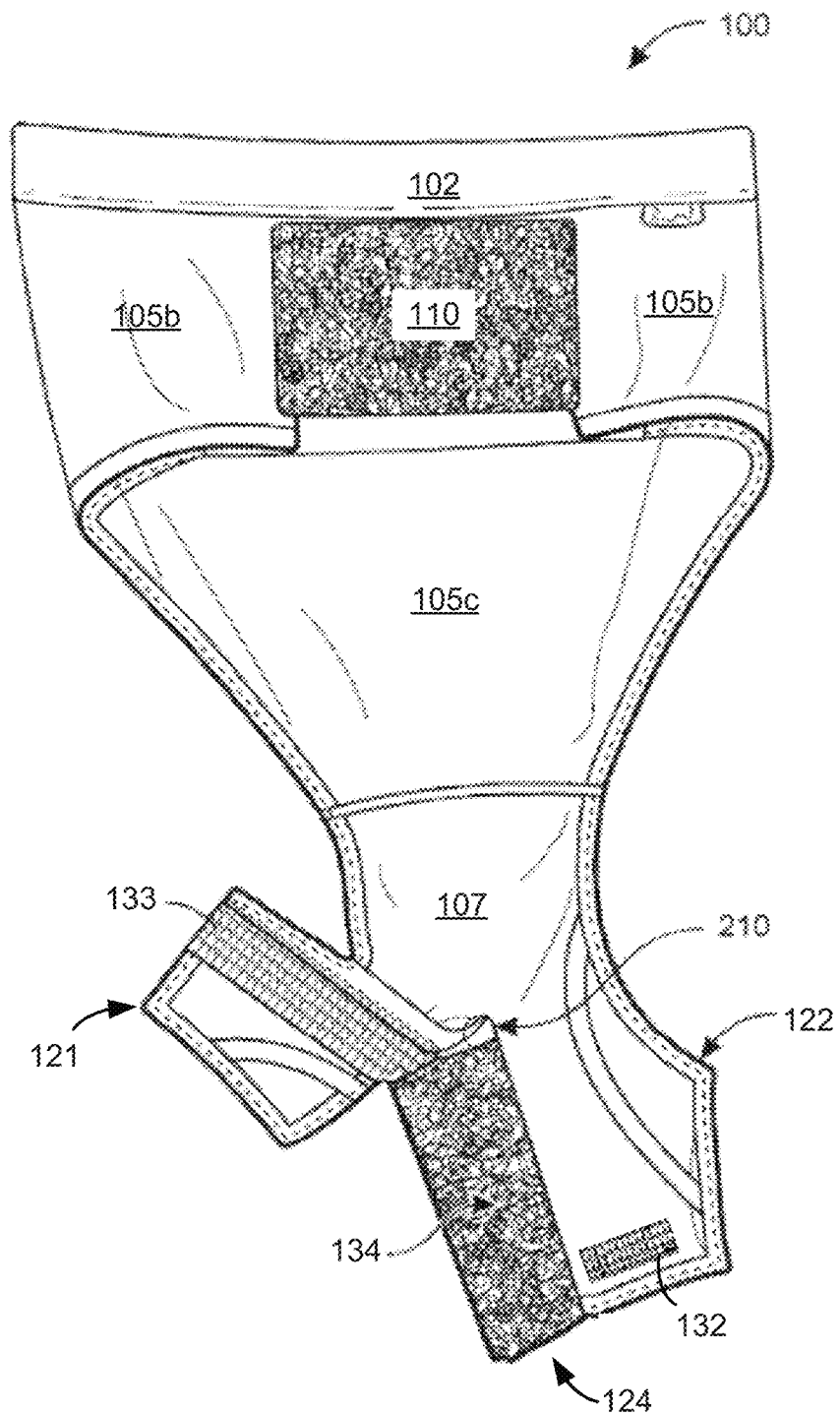
FIG. 3 is a front view of an example medical garment of a device or system for stabilizing medical tubing protruding from a patient with adjustable flaps in unattached positions and separated from one another, according to embodiments of the present disclosure.
Figure 4:
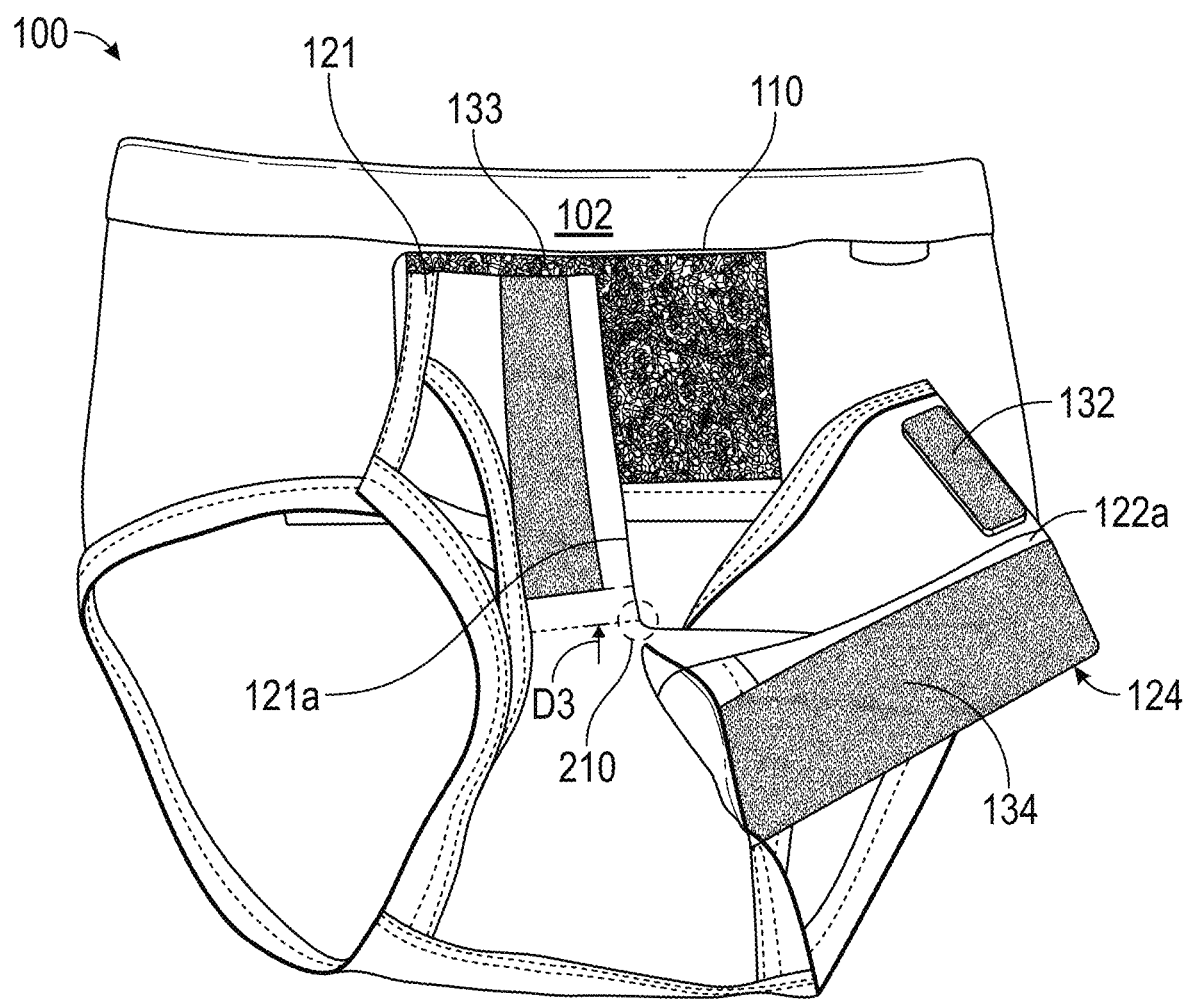
FIG. 4 is a front view of an example medical garment of a device or system for stabilizing medical tubing protruding from a patient with a first adjustable flap in an attached position, a second adjustable flap in an unattached position, and a third flap in an unattached position, according to embodiments of the present disclosure.

As is best shown in FIGS. 2-4, an adjustable garment 100, according to embodiments of the present disclosure, may further comprise a third flap 124 coupled to and configured to hinge or flip with respect to the medial (e.g., vertical) edge of second flap 122 about a vertical seam 125 (see FIG. 5), e.g., between second flap 122 and third flap 124. Third flap 124 is also configured to be disposed directly over, and adjustably and releasably attach to, at least a portion of first flap 121 when second flap 122 is adjustably coupled to first attachment portion 110. Accordingly, in some embodiments, third flap 124 has a substantially rectangular form factor or shape, having a height and a width. In some embodiments, third flap 124 is sized sufficiently to cover an entire width of first flap 121. In some embodiments, for example as shown in at least FIGS. 2 and 5, the height is greater than the width. However, the present disclosure is not so limited and the width may be greater than the height, or the width and height may have substantially the same value.

As best shown in FIGS. 3 and 4, a fourth attachment portion 133 is disposed along an outward-facing surface of first flap 121, opposite of the inward, patient-facing surface on which second attachment portion 131 is attached. In some embodiments, fourth attachment portion 133 may extend, uninterrupted, from a top-most edge of first flap 121 to a position, or horizontal line, that is a predetermined distance $D_3$ from vertex 123, see, e.g., FIG. 4. This predetermined distance $D_3$ may be approximately equal to a diameter of the largest medical tube or catheter which garment 100 is configured to secure. However, the present disclosure is not so limited and the predetermined distance $D_3$ may be any distance suitable for securing the medical tubes or catheters as described in this disclosure. In some embodiments, fourth attachment 133 is substantially rectangular in shape and vertically oriented on first adjustable flap 121.

Similarly, a fifth attachment portion 134 is disposed along an inward, patient-facing surface of third flap 124 that is disposed directly over at least a portion of first flap 121 when second flap 122 is adjustably coupled to first attachment portion 110. In some embodiments, fifth attachment portion 134 may extend, uninterrupted, along substantially an entire width of the exposed inward, patient-facing surface of third flap 124 from a top-most end of third flap 124 to a bottom-most end of third flap 124. Accordingly, when third flap 124 is disposed directly on the outward-facing surface of first flap 121, fifth attachment portion 134 is configured to releasably couple with substantially the entire attaching surface of fourth attachment portion 133, thereby defining a catheter exit port 210 as a circular tunnel, or aperture, having sidewalls entirely formed from the facing unattached surfaces of first adjustable flap 121, second adjustable flap 122, and/or third flap 124 that are within the predetermined distance $D_3$ from vertex 123 when the medical tube, catheter or tube engagement element 310 of patch 300 is disposed to extend therethrough. This provides a snug, tight, circular hole through which the medical tubing, catheter, and/or the tube engagement element 310 of patch 300 extends. Accordingly, an entire uninterrupted perimeter of the medical tubing, catheter and/or of the tube engagement element 310 of patch 300 is in direct physical contact with this aggregately created tight circular hole at the same time, thereby securing and preventing the medical tubing, catheter and/or tube engagement element 310 of patch 300 from moving whatsoever in either the lateral-medial direction, or in the vertical direction with respect to garment 100 and, since garment 100 is entirely form fitting and substantially stationary with respect to the body of the patient, also with respect to the exit location for the medical tubing or catheter from the patient's body.

Notably, this is an entirely different concept from a mere slot or slit having a larger dimension in one direction (e.g., the direction of extension of any mere slot or slit) compared to another direction (e.g., the direction of extension of any mere slot or slit) utilized by prior solutions, where a mere slot or slit cannot contact the medical tubing, catheter, or tube engagement element 310 of patch 300 around the entire perimeter, or substantially entire perimeter, thereof to, thereby, secure and prevent it from moving in both the lateral-medal direction and the vertical direction with respect to garment 100. Moreover, mere slits or slots, if large enough, cannot hold the male anatomy inside garment 100 and will, contrarily, encourage the male genital anatomy to slip or fall out of the garment.

Accordingly, fourth and fifth attachment portions 133, 134 may, for example, attach to each other via a conventional hook and loop method (e.g., Velcro brand), reusable adhesive, and/or any other suitable method for repeatably attaching fabrics to one another. For example, fourth attachment portion 133 may comprise one of hook or loop fasteners while fifth attachment portion 134 may comprise the other of the hook or loop fasteners. In some embodiments, fifth attachment portion 134 may comprise the same hook or loop fasteners as first attachment portion 110 disposed on the anterior lower abdominal portion of body portion 105. Accordingly, fourth attachment portion 133 is configured to adjustably couple with fifth attachment portion 134 but not with third attachment portion 132, which may be disposed on an inward, patient-facing surface of second adjustable flap 122 that is adjacent to the inward, patient-facing surface of third adjustable flap 124. Similarly, fifth attachment portion 134 is configured to adjustably couple with fourth attachment portion 133 but not first attachment portion 110, e.g., portions of first attachment portion 110 that would be disposed on an outward-facing anterior surface of body portion 105 adjacent to fourth attachment portion 133 when first adjustable flap 121 is properly releasably coupled to first attachment portion 110 on body portion 105 of garment 100. This prevents fourth and fifth attachment portions 133, 134 from accidentally and/or undesirably coupling with the wrong portions of garment 100 and the attendant readjustment discomfort. However, the present disclosure is not so limited and fourth and fifth attachment portions 133, 134 may each comprise the appropriate one of a first type of fastener or first portion of an adjustable fastener assembly, or a second type of fastener or second portion of the adjustable fastener assembly wherein the first type of fastener or first portion of the adjustable fastener assembly is configured to mate with the second type of fastener or second portion of the adjustable fastener assembly but not another first type of fastener or first portion of the adjustable fastener assembly, and wherein the second type of fastener or second portion of the adjustable fastener assembly is configured to mate with the first type of fastener or first portion of the adjustable fastener assembly but not another second type of fastener or second portion of the adjustable fastener assembly, such that such that fourth attachment portion 133 is configured to adjustably couple with fifth attachment portion 134 but not with third attachment portion 132 and, similarly, fifth attachment portion 134 is configured to adjustably couple with fourth attachment portion 133 but not first attachment portion 110, e.g., portions of first attachment portion 110 that would be disposed on an outward-facing anterior surface of body portion 105 adjacent to fourth attachment portion 133 when first adjustable flap 121 is properly releasably coupled to first attachment portion 110 on body portion 105 of garment 100.

This predetermined distance Da ultimately defines, at least in part, the circumference of this circular tunnel or aperture. Forming the tunnel as described above is specifically to provide substantially equal pressure distributed about substantially an entire uninterrupted perimeter of the medical tubing or catheter, sufficient to immobilize the medical tubing or catheter, or tube engagement element 310, while simultaneously actually being incapable of (e.g., insufficiently large for) closing off, or even physically deforming (e.g., bending, kinking) the catheter lumen, by accident or intention.

Figure 13:
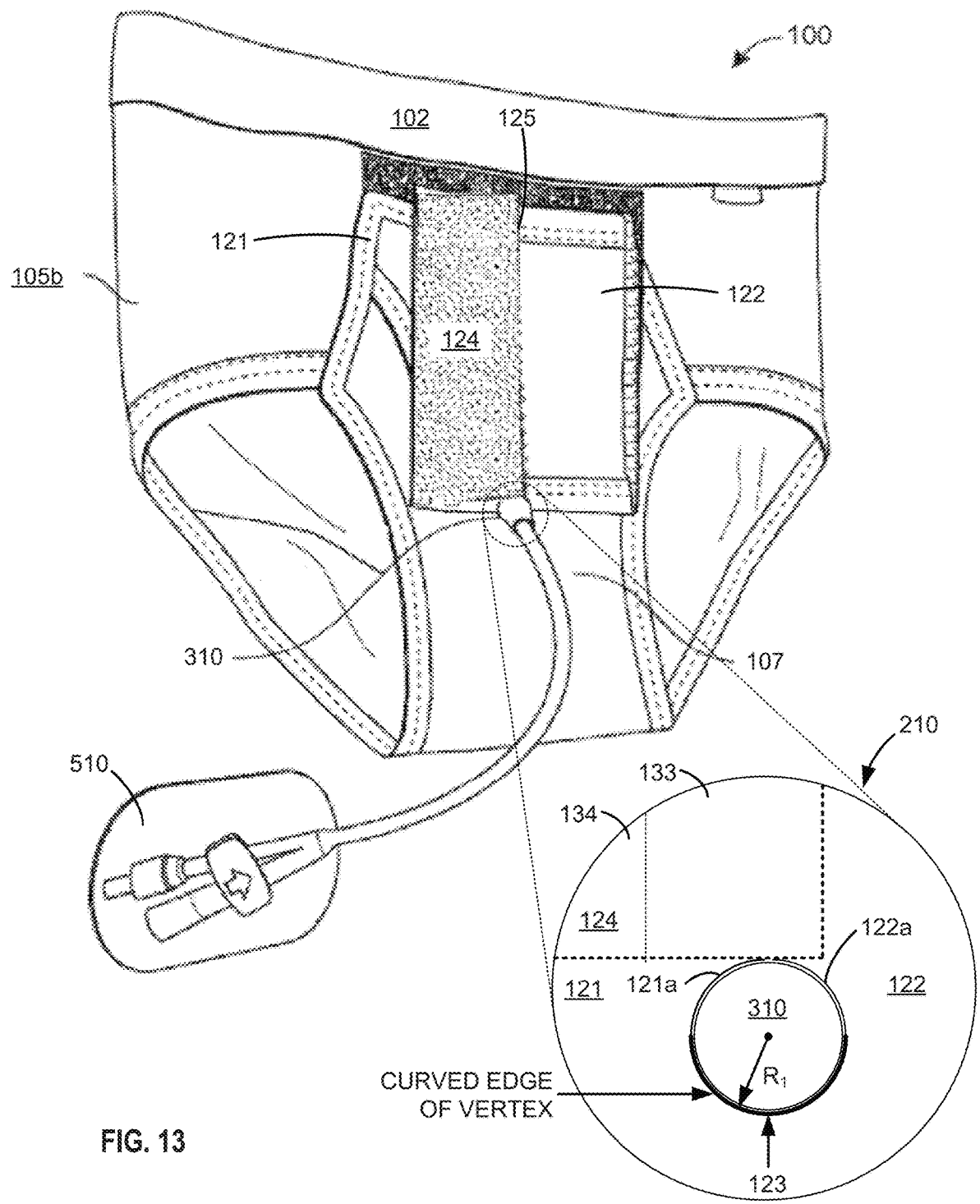
FIG. 13 is a perspective view of an example medical garment of a device or system for stabilizing medical tubing protruding from a patient with all flaps in attached positions, the example medical tubing protruding from a patient being passed through the tube stabilization patch disposed between the body of the patient and the medical garment, between first and second adjustable flaps, and situated in a catheter exit port, according to embodiments of the present disclosure.

Moreover, as previously described, and as can also be viewed in more detail in the magnified portion of FIG. 13, where vertex 123 comprises the curved edge having the minimum radium of curvature $R_1$, as medial edges 121*a*, 122*a* of first and second adjustable flaps 121, 122 are secured around the medical tubing or catheter (or tube engagement element 310, as shown in FIG. 13), the curved edge having the minimum radius of curvature $R_1$ approximately equal to the radius of the medical tubing, catheter or tube engagement element 310 ensures that medial edges 121*a*, 122*a* of first and second adjustable flaps 121,122 immediately extending from the curved edge always extend in a direction that is substantially tangential to the outer perimeter of the medical tubing or catheter (or of the outer perimeter of tube engagement element 310 of patch 300) around which those medial edges 121*a*, 122*a* are directly and uninterruptedly secured. You can further see, in the magnified portion of FIG. 13, how the immediate portions of medial edges 121*a*, 122*a* extending from the curved portion of vertex 123 are in direct contact with, and contour, the outer perimeter of the medical tubing, catheter or tube engagement element 310 to where fourth attachment portion 133, which is attached to the outward-facing surface of first adjustable flap 121 and shown as the substantially rectangular portion within the dotted lines, is adjustably coupled with fifth attachment portion 134, which is attached to and may in some embodiments cover the entire inward, or patient-facing surface of third flap 124 (the horizontal edge of which is illustrated as the heavy dotted line to show the underlying aspects). And as also illustrated in FIG. 13, the horizontal dotted line, illustrating the lower edge of third flap 124, is shown properly secured to and over first adjustable flap 121, so as to be in contact with the topmost portion or surface of the outer perimeter of the medical tubing, catheter or tube engagement element 310. In this way, each of medial edges 121a, 122a of first and second adjustable flaps 121,122 and third flap 124 (especially its bottom horizontal edge) each provide its part of the aggregate formation of exit port 210. Together, this enables substantially equal pressure about the entire perimeter of the medical tubing (or around the outer perimeter of tube engagement element 310 of patch 300) around which those medial edges are secured that is also incapable of closing off, or even physically deforming, the catheter lumen, by accident or intention.

Referring to FIG. 3, this figure depicts a front view of an example medical garment of a device or system for stabilizing medical tubing protruding from a patient with an adjustable flap in an unattached position and first and second flaps 121, 122 separated from or unattached to one another, according to embodiments of the present disclosure.

According to various embodiments of the present disclosure, and as described or alluded to above, various portions of garment 100, including the aspects of adjustable flap portion 120 cooperate functionally to form a securing mechanism (i.e., a medical tubing and/or catheter securing mechanism). Such a securing mechanism may include previously-described catheter exit port 210, which in embodiments may be, in aggregate, a substantially circular tunnel or aperture that allows for a medical tube or catheter to pass therethrough.

The example depicted in FIG. 3 shows medical garment 100 with both first and second adjustable flaps 121, 122 of adjustable flap portion 120 unattached from the anterior portion of body portion 105 and third flap 124 unattached from first adjustable flap 121.

FIG. 4 depicts a front view of medical garment 100 with first adjustable flap 121 adjustably attached to body portion 105, while second adjustable flap 122 is not adjustably attached to body portion 105 and third flap 124, which is hingedly fixed to an outward-facing surface of second adjustable flap 122, is not removably attached to first adjustable flap 121. Specifically, second attachment portion 131 is coupled directly to first attachment portion 110 at a first location, but third attachment portion 132 is not coupled to first attachment portion 110 and fourth attachment portion 133 is not coupled to fifth attachment portion 134.

Figure 5:
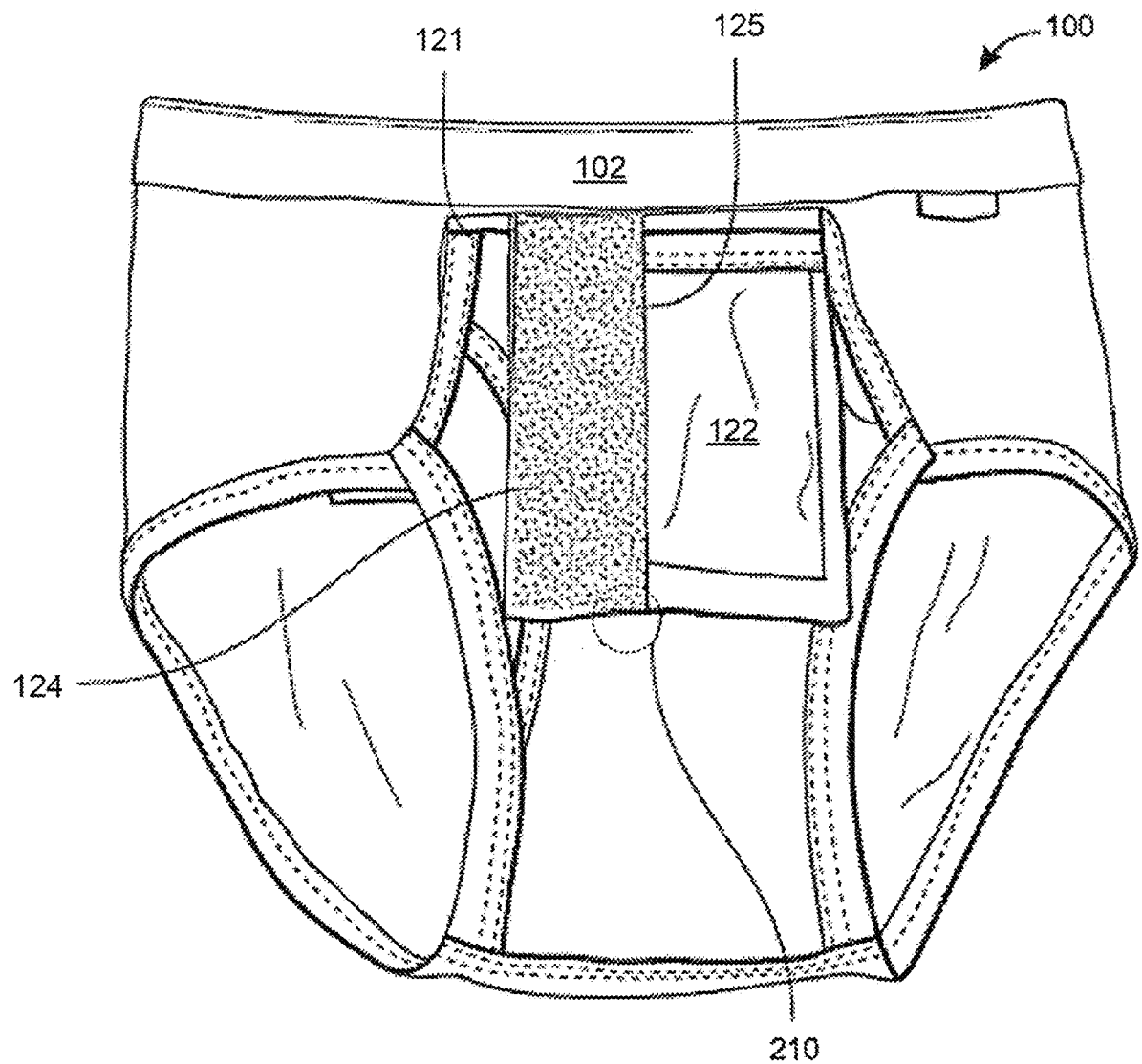
FIG. 5 is a front view of an example medical garment of a device or system for stabilizing medical tubing protruding from a patient with adjustable flaps in attached positions, according to embodiments of the present disclosure.

The example depicted in FIG. 4 may occur when a patient has already donned the medical garment and is in the process of securing the medical tubing (as discussed below), but before the medical garment 100 is fully secured on the patient (as depicted in FIG. 5).

FIG. 5 depicts a front view of medical garment 100 with both first adjustable flap 121 and second adjustable flap 122 adjustably attached to body portion 105, and third flap 124, which is hingedly fixed to an outward-facing surface of second adjustable flap 122, removably attached to first adjustable flap 121. Specifically, second attachment portion 131 is coupled directly to first attachment portion 110 at a first location, third attachment portion 132 is coupled to first attachment portion 110 at a second location, and fourth attachment portion 133 disposed on the outward-facing surface of first adjustable flap 121 is coupled to fifth attachment portion 134 disposed on the inward, patient-facing surface of third flap 124.

Accordingly, as shown in FIG. 5, medical garment 100 may be fully secured on a patient such that catheter exit port 210 is situated at or about the desired location for protruding medical tubing or a catheter to exit the medical garment (e.g., immediately opposite the actual exit point of the medical tubing and/or catheter from the patient's body).

Figure 6A:
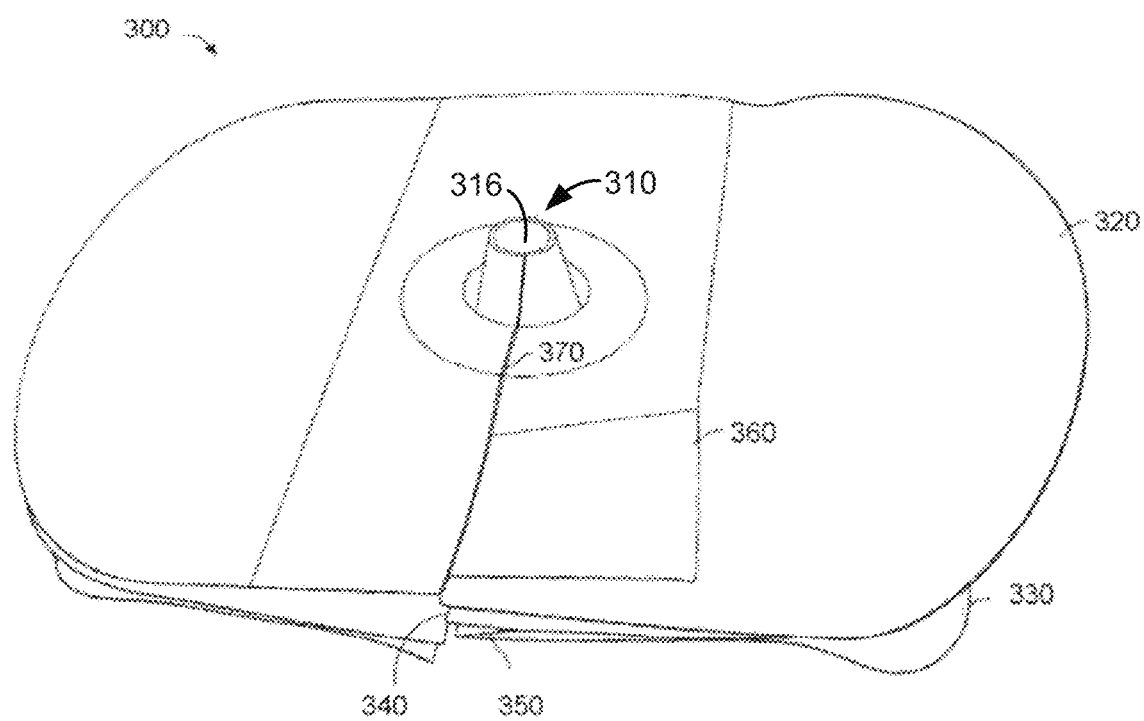
FIG. 6A illustrates a perspective view of an example tube stabilization patch of a device or system for stabilizing medical tubing protruding from a patient, according to various embodiments of the present disclosure.

Discussion now turns to various embodiments of a tube stabilization patch 300, according to example embodiments. FIG. 6A is a perspective view of an example tube stabilization patch 300 of a device or system for stabilizing medical tubing protruding from a patient, according to embodiments of the present disclosure.

According to various embodiments of the present disclosure, a lube stabilization patch 300 may be provided. The tube stabilization patch 300 may include a tube engaging element 310, a patient attachment element 320, and an access separation 370.

Tube engaging element 310 may include a flexible, openable bore 316 that may be configured to engage an external surface of medical tubing or a urinary catheter. Openable bore 316 may extend through tube engaging element 310 and prevent or reduce relative movement of the medical tubing or urinary catheter in relation to the patient, tube engaging element 310, tube stabilization patch 300, or similar. Tube stabilization patch may reduce the amount of relative movement (lateral, longitudinal, "pistoning") of the medical tubing or catheter when the medical tubing or catheter is situated in openable bore 316 of tube engaging element 310.

Openable bore 316 may be configured to engage an external surface of a medical tube (e.g., a catheter). In some embodiments, openable bore 316 may be configured to directly physically engage an uninterrupted external perimeter surface, in some cases an entire uninterrupted external perimeter, of a tubular medical port or a retaining element releasably and securely attached to the medical drainage tube in order to prevent or reduce relative movement of the medical tubing in relation to the tube or tube stabilization patch 300. This stabilization may occur when the medical tubing is disposed or positioned in the tube engaging element's 310 openable bore 316. In embodiments, the medical tubing may be placed or positioned through openable bore 316 from back to front or front to back, parallel to a direction of extension of bore 316 and perpendicular to the lateral directions in which tube stabilization patch 300 extends.

As will be described in more detail below, tube engaging element 310 may comprise two or more opposing and openable bore edges formed at, and by, a portion of access separation 370. For example, in some embodiments, tube engaging element 310 may be a resilient material formed into an openable sidewall. The resilient material may be, or comprise, rubber (natural, synthetic, or a combination thereof), silicone, any suitable plastic, another suitable medical grade elastomeric material, or a combination thereof. The resilience of tube engaging element 310, along with specific aspects of its construction, allow for tube stabilization patch 300 to dampen, or substantially eliminate, movement on the body caused by movement of the medical tubing or catheter when one or more of longitudinal, lateral, or piston forces are applied to the tubing or the catheter. Additionally, tube engaging element 310 may be coated with an antibacterial or antimicrobial agent, which can further reduce the risk of infection in patients.

Figure 6E:
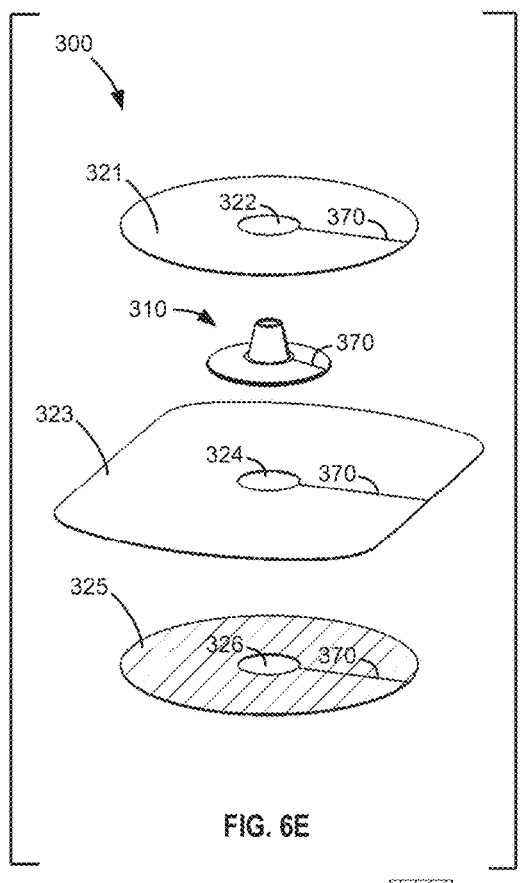
FIG. 6E illustrates an exploded perspective view of a first configuration of a tube stabilization patch as viewed from the top, according to various embodiments of the present disclosure.
Figure 6F:
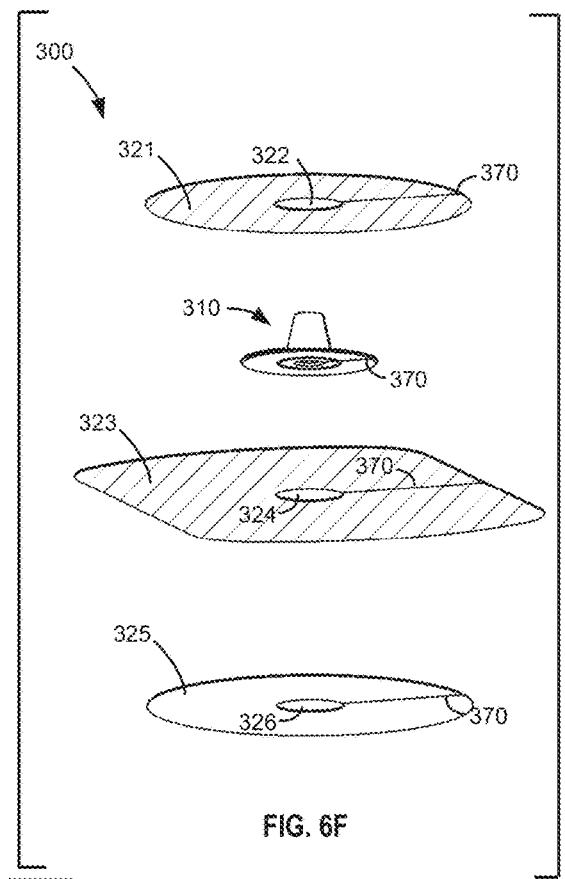
FIG. 6F illustrates an exploded perspective view of the first configuration of the tube stabilization patch of FIG. 6E as viewed from the bottom.
Figure 6G:
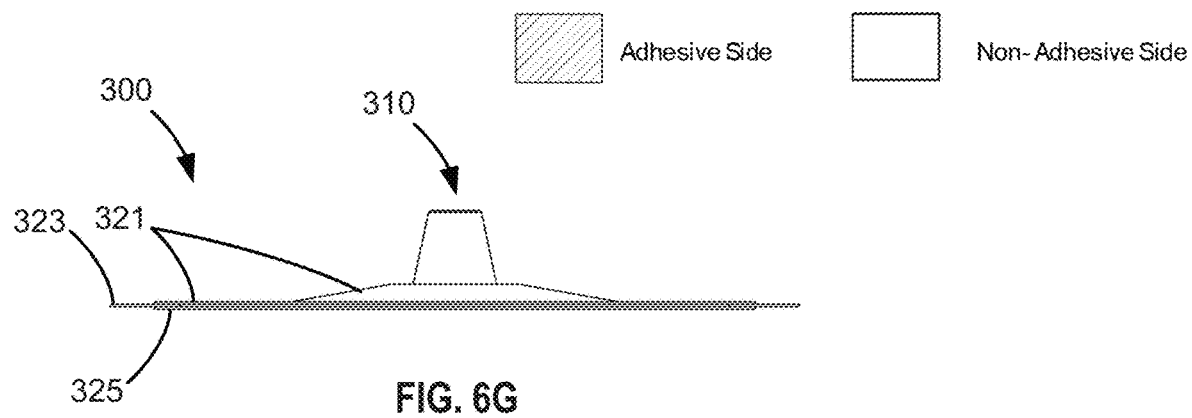
FIG. 6G illustrates a side view of the assembled first configuration of the tube stabilization patch of FIGS. 6E-6F.
Figure 6H:
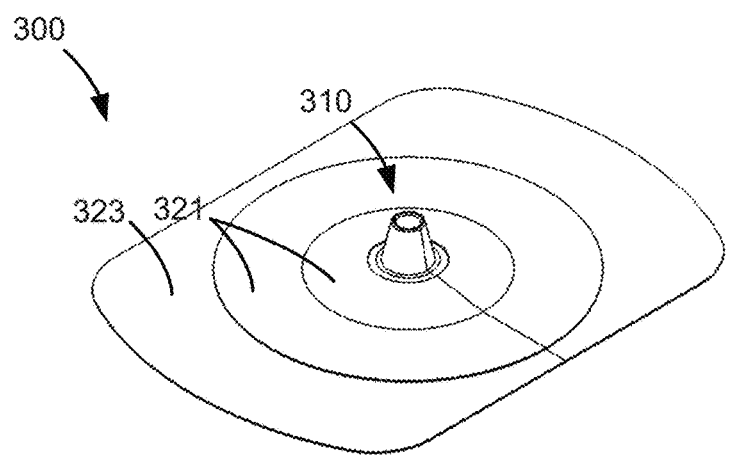
FIG. 6H illustrates a perspective view of the assembled first configuration of the tube stabilization patch of FIG. 6G as viewed from the top.
Figure 6I:
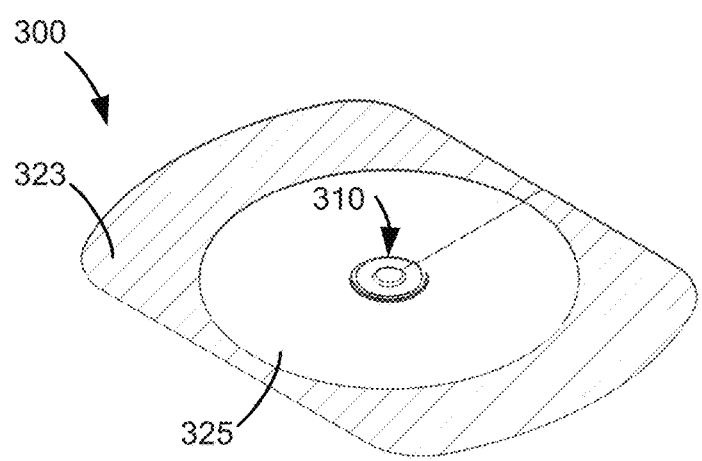
FIG. 6I illustrates a perspective view of the assembled first configuration of the tube stabilization patch of FIG. 6G as viewed from the bottom.
Figure 6L:
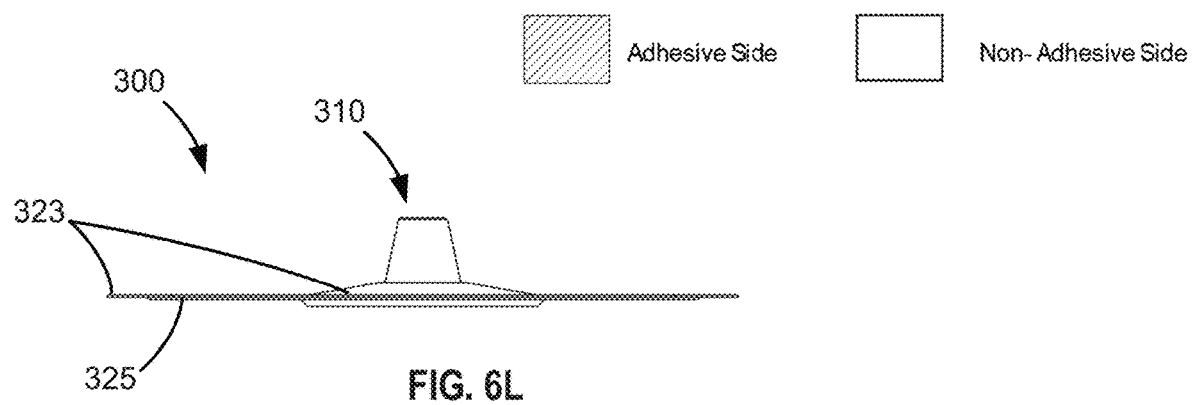
FIG. 6L illustrates a side view of the assembled second configuration of the tube stabilization patch of FIGS. 6J-6K.
Figure 6M:
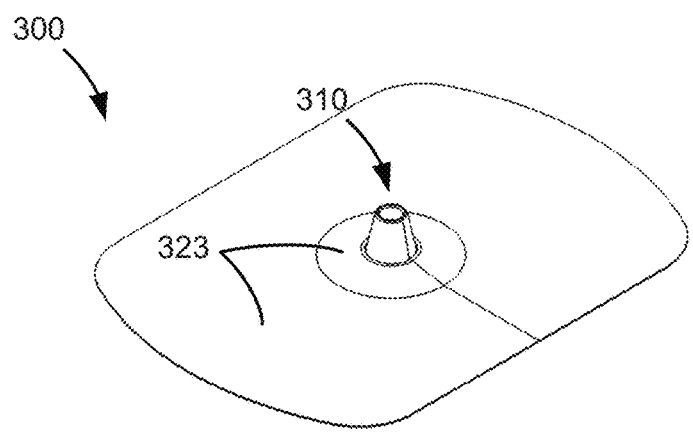
FIG. 6M illustrates a perspective view of the assembled second configuration of the tube stabilization patch of FIG. 6L as viewed from the top.
Figure 6N:
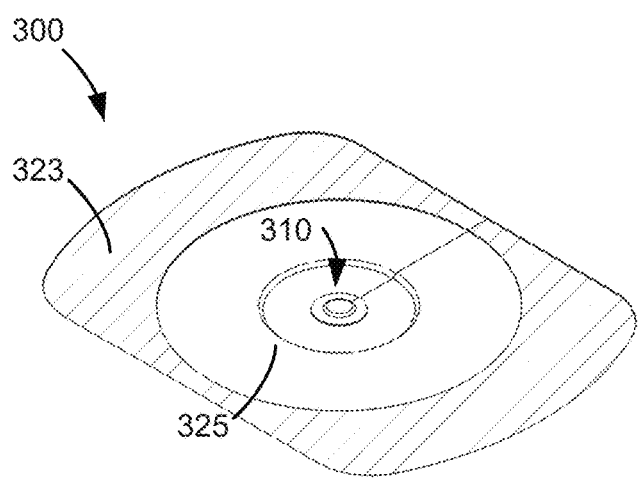
FIG. 6N illustrates a perspective view of the assembled second configuration of the tube stabilization patch of FIG. 6I as viewed from the bottom.
Figure 6P:
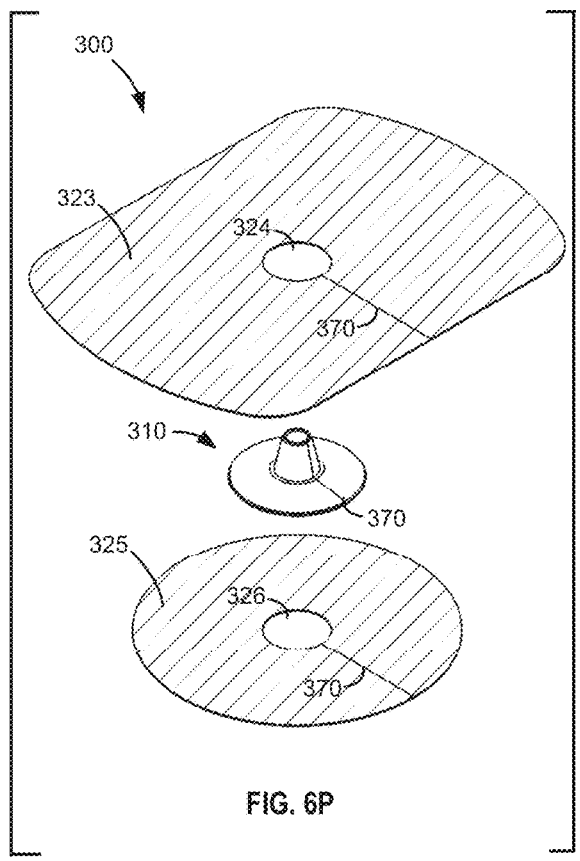
FIG. 6P illustrates an exploded perspective view of a third configuration of a tube stabilization patch as viewed from the top, according to various embodiments of the present disclosure.
Figure 6Q:
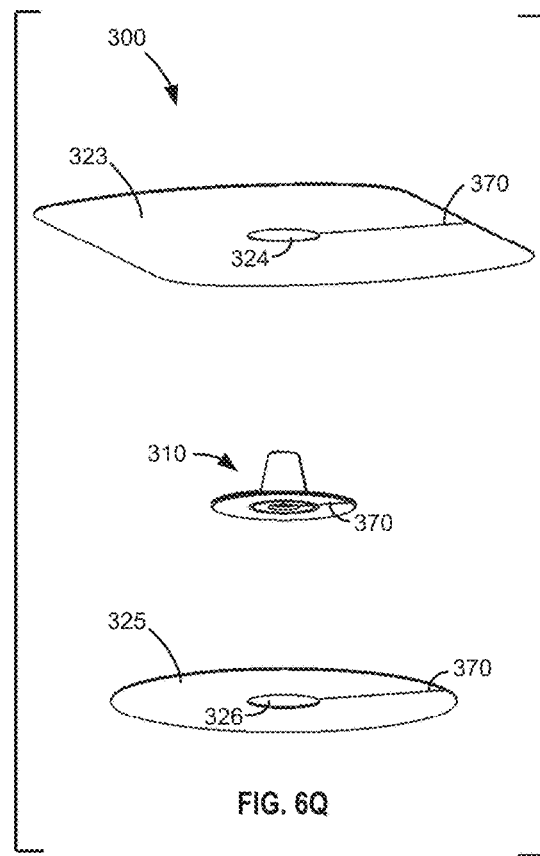
FIG. 6Q illustrates an exploded perspective view of the third configuration of the tube stabilization patch of FIG. 6P as viewed from the bottom.
Figure 6R:
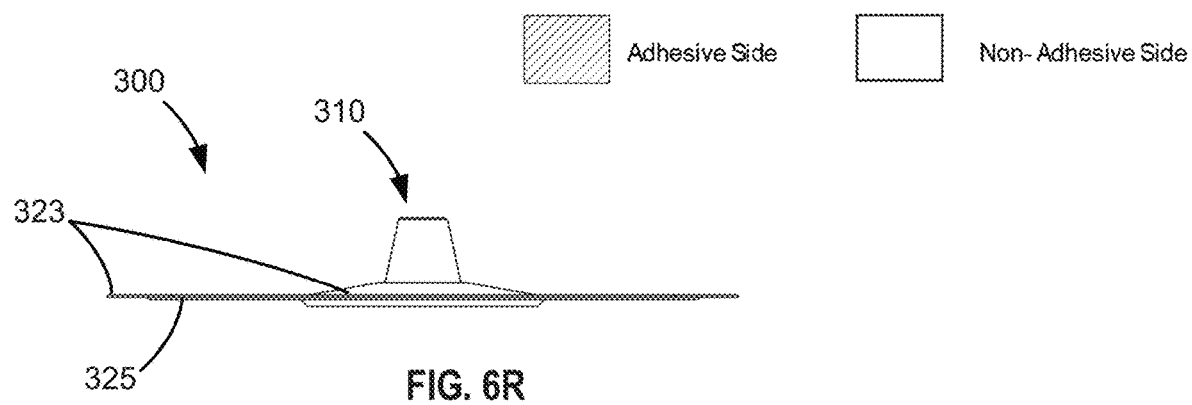
FIG. 6R illustrates a side view of the assembled third configuration of the tube stabilization patch of FIGS. 6P-6Q.
Figure 6S:
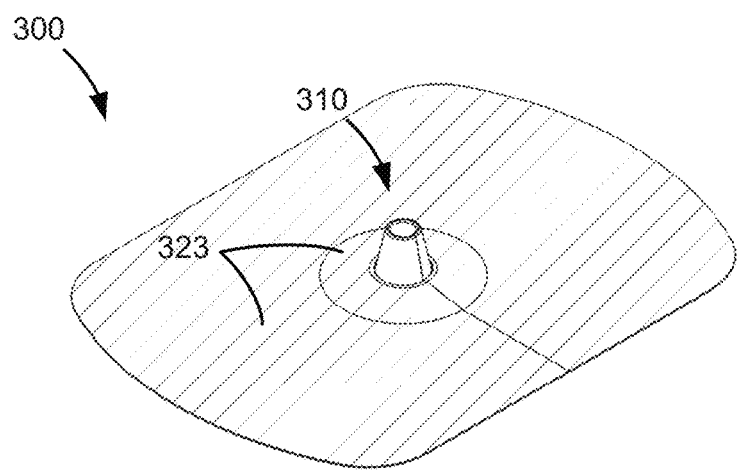
FIG. 6S illustrates a perspective view of the assembled third configuration of the tube stabilization patch of FIG. 6R as viewed from the top.
Figure 6T:
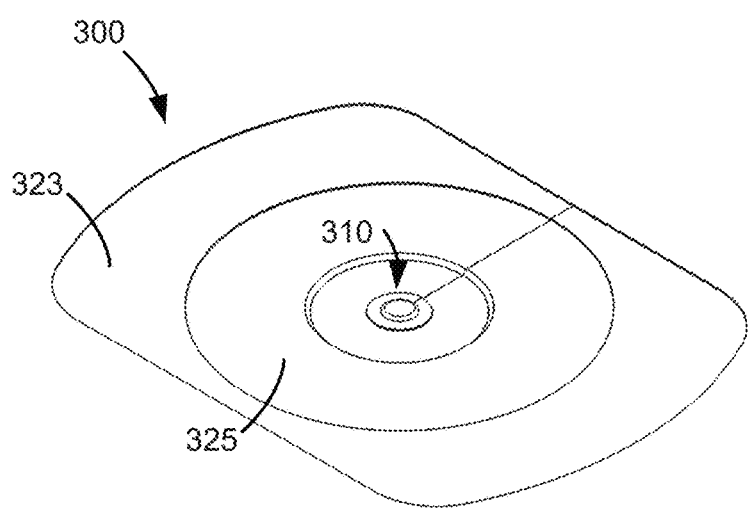
FIG. 6T illustrates a perspective view of the assembled third configuration of the tube stabilization patch of FIG. 6R as viewed from the bottom.

Several aspects of tube stabilization patches 300 are disclosed in connection with any one or more of FIGS. 6A-6T. For example, an embodiment of tube engaging element 310, formed of a flexible material, such as silicone or any other suitable medical grade elastomeric material, and forming a part of a tube stabilization patch 300, is shown in FIGS. 6C and 6D. FIG. 6C illustrates a top view of this embodiment of tube engaging element 310, while FIG. 6D illustrates a side cutaway view of tube engaging element 310 as viewed from the direction of the cutline arrows A-A in FIG. 6C. As shown in FIGS. 6C and 6D, in some embodiments, tube engaging element 310 comprises a base 312 and a conical extending portion 314 that extends away from a top surface of base 312 (see, e.g., FIGS. 6C, 6D and views E-E and F-F and their accompanying sections in FIGS. 19A, 19B, 19E and 19F). However, the present disclosure is not so limited and, in some embodiments, tube engagement element may alternatively comprise base 312 and an extending portion that is cylindrical 314a (see, e.g., views G-G and H-H, and their accompanying sections, in FIGS. 19C, 19D, 19G and 19H). In yet other embodiments, the extending portion previously shown as conical extending portion 314 or cylindrical extending portion 314a may have any other suitable external form, such as a convexly curving and tapering outer surface (similar to that of a bullet), or such as a concavely curving and tapering outer surface (having a substantially opposite curvature from that of the convexly curving surface described above). Accordingly, any mention of conical extending portion 314 or of cylindrical extending portion 314a, or of any alternative form for the extending portion herein, may be contemplated as considered interchangeable between any embodiments described herein. In some embodiments, base 312 has a substantially circular form factor. However, the present disclosure is not so limited and base 312 may have any suitable form factor, e.g., ovoid or substantially rectangular with rounded corners. Access separation 370 intersects both base 312 and the wall of conical extending portion 312 so that conical extending portion 314 may be configured to form a fully closed "O" shape or a nearly-closed "C" shape, when viewed from the top or bottom of conical extending portion 314 along its direction of extension, that is in direct physical contact with an entire, or substantially entire, uninterrupted perimeter of medical tubing or catheter that extends through bore 316 of conical extending portion 314.

In order to increase flexibility, pliability and the ability of tube engaging element 310, and so tube stabilization patch 300, to conform to the patient's body and/or garment 100, in an unstressed orientation, base 312 may have a substantially planar, flat back surface 311 and a slightly angled top surface 313 such that a thickness of base 312 increase toward its center and decreases toward its perimeter. In some embodiments, conical extending portion 314 is centered on base 312 and both elements are parts of a single, monolithic structure. Conical extending portion 314 has a height $H_1$. Conical extending portion 314 also has a diameter that is largest at base 312 and that decreases as conical extending portion 314 extends away from base 312. In some embodiments, height $H_1$ of conical extending portion 314 is greater than its smallest inside diameter (e.g., De), which may enforce at least a minimum radius of curvature of, and sufficient strain relief for, medical tubing or a catheter extending therethrough. In some other embodiments, height $H_1$ of conical extending portion 314 is at least 1.25× its largest inside diameter (e.g., $D_1$) to enforce a slightly different minimum radius of curvature of, and correspondingly sufficient strain relief for, medical tubing or a catheter extending therethrough. In yet other embodiments, height $H_1$ of conical extending portion 314 is at least 1.5× its largest inside diameter (e.g., $D_1$) to enforce yet a different minimum radius of curvature of, and correspondingly sufficient strain relief for, medical tubing or a catheter extending therethrough.

By contrast, designs having an insufficient height to inner diameter ratio (e.g., smaller than 1:1) cannot, as a matter of engineering design, provide sufficient strain relief to prevent rotation and/or lateral movement (e.g., flopping and/or twisting) of the catheter from silicone, or any other suitable medical grade elastomeric material, while also preventing folding over, bending, deforming or other occlusion of the medical tubing and/or catheter.

Circular bore 316 extends entirely through conical extending portion 312 and underlying base 312. In some embodiments, bore 316 has an inner wall 315 that tapers as it extends away from base 312. For example, bore 316 may have a largest diameter $D_1$ at a bottom of base 312 that tapers to a smallest diameter $D_2$, less than $D_1$, at a tip of conical extending portion 314. Accordingly, a thickness of the material of conical extending portion 314 between the outer surface and inner wall 315 decreases along a length of extension of conical extending portion 314 away from base 312. This allows for the greatest stiffness of conical extending portion 314 to be at base 314 and, also, for that stiffness to decrease, and pliability and flexibility to increase, along the length of extension of conical extending portion 314 away from base 312. Pliability and flexibility of the walls of conical extending portion 314 increasing as the diameter of bore 316 decreases along its length of extension helps ensure the direct physical contact with medical tubing or a catheter disposed therein is substantially uniform and equal about an entire perimeter of the medical tubing disposed within bore 316. Stated another way, the reduction in diameter from $D_1$ to $D_2$ helps keep uniform pressure as the material thickness of conical section 314 decreases. Bore 316 gets tighter to compensate as the material gets thinner and more flexible.

This simultaneously decreasing thickness of conical sidewalls as the bore diameter decreases, along with the access separation 370 allowing the conical sidewalls to more easily flex outward from the fully closed "O" shape (as viewed from the angle of FIG. 6C) to the nearly closed substantially "C" shape (also as viewed from the angle of FIG. 6C) and in a graded and controlled manner also allows a particularly-sized tube engaging element 310 to appropriately secure a variety of adjacent catheter sizes in the specific manner described by this disclosure. Moreover, it allows extending portion 314 to accommodate medical tubing and/or catheters having significantly greater diameters than the at-rest diameters $D_1$ and/or $D_2$ of bore 316 while still providing the direct physical contact with an uninterrupted perimeter of the medical tubing or catheter (e.g., substantially the entire uninterrupted perimeter of the medical tubing or catheter) that is specifically designed to provide substantially equal pressure about the entire perimeter of the medical tubing within bore 316 while being incapable of closing off, or even physically deforming, the catheter lumen, by accident or intention.

For example, in one embodiment of tube engaging element 310, $H_1$ might be 0.35 inches, $D_1$ might be 0.18 inches and $D_2$ might be 0.16 inches. Such a tube engaging element 310 may be utilized for 14Fr, 16Fr and 18Fr catheters. In another embodiment of tube engaging element 310, $H_1$ might be 0.50 inches, $D_1$ might be 0.25 inches and $D_2$ might be 0.23 inches. Such a tube engaging element 310 may be utilized for 20Fr, 22Fr and 24Fr catheters.

Tube engagement element 310 also provides a solution to a real-world problem related to inconsistency in labelled versus actual size of catheters formed by different techniques. For example, actual diameters of injection molded silicone catheters are relatively consistent and tend to match the labelled French size (e.g., the labelled 18Fr actually has a diameter of 18/3=6 mm). However, a dip-molded 14Fr latex catheter may have an actual diameter that is the size of a 16Fr injection molded silicone catheter. By combining the above-described features of tube engaging element 310, such inconsistencies in catheter diameter between differently formed catheters, for example of a same labelled size, do not present a problem with the present invention's ability to physically stabilize the catheter with direct physical contact having a substantially equal pressure about an entire perimeter of the medical tubing. Namely, this design is also auto-adjusting, because access separation 370 through the flexible silicone construction tube engaging element 310 allows for an even expanding of an effective diameter of inner wall 315 of conical portion 314 that always ensures the above-described direct physical contact with the entire, or substantially entire, uninterrupted perimeter of the catheter. A substantially equal pressure that is actually incapable of closing off, or even physically deforming whatsoever, the catheter lumen, by accident or intention.

However, the present disclosure is not so limited and, in addition to the extending portion of tube engagement element 310 being conical (e.g., 314) or cylindrical (e.g., 314*a*), as also shown in FIGS. 19A-19H, either of conical extending portion 314 or cylindrical extending portion 314*a* may comprise either tapering, conical bore 316, as described above, or, alternatively, may comprise a cylindrical bore 316*a* having, for example, the base diameter $D_1$ along substantially its entire length of extension The patient attachment element 320 may be connected to a perimeter of the tube engaging element 310. Any suitable set of complementary structural or mechanical features can be used to allow for attachment between the tube engaging element and the patient attachment element, including mechanically interlocking features, magnetic elements, adhesives, and the like. Patient attachment element 320 may be various shapes, thicknesses, and densities. For example, the patient attachment element 320 may be oblong with a non-constant radii, as depicted in at least FIG. 6A. In other examples, the patient attachment element 320 may be circular with a constant radius, square, rectangular, or any other shape that allows for attachment to a patient.

Patient attachment element 320 may also include a plurality of layers. Such layers may include a fabric or paper liner, such as but not limited to a cotton fabric, a woven fabric, or a non-woven fabric such as polyester. In some embodiments, the layers of patient attachment element 320 may have a thickness of between 1-5 mm and, more preferably, a thickness of approximately 0.5-1.0 mm.

However, patient attachment element 320 combined with the base of tube engagement element 310 is, and must be, sufficiently pliable to be disposed against, adhered to, and maintained in the precise mating contour of the patient's body. This contrasts prior solutions that utilize a foam construction in place of, or in addition to, fabric layer(s) 320, at least because such foam construction is, by nature, too bulky and inflexible to provide and maintain the required precise mating contour of the patient's body for hours at a time under ambulatory conditions. Moreover, the added weight and/or increased form factor of such prior foam block construction would cause undesirable movement of tube stabilization patch 300 by virtue of the comparatively increased thickness and associated side surface area of such a foam layer and its interaction with surrounding clothing. Moreover, where tube stabilization patch 300 is adhered to garment 100, this same comparatively increased interaction and surface area of inferior foam construction would similarly act to detach tube stabilization patch 300 from garment 100 or from the patient's body when the patient began ambulation.

Patient attachment element 320 may comprise an adhesive backing or lining 330. Such an adhesive backing or lining 330 may be a removable peel-away liner that when removed exposes an adhesive backing. The adhesive layer may be disposed on either side of the patient attachment element 320, which may allow for the tube stabilization patch to be adhered to the interior or exterior of the medical garment (as discussed below) or directly adhered to the patient. For example, in some embodiments, adhesive backing or lining 330 may be disposed on a same side of patient attachment element 320 from which the conical tube engaging element 310 extends. In some such embodiments, no adhesive backing or lining is disposed on the opposite side of patient attachment element 320 from which the conical tube engaging element 310 extends to prevent or avoid tube stabilization patch 300 from being simultaneously adhered to both the garment 100 and also directly to the patient's body. In other embodiments, adhesive backing or lining 330 may be disposed on an opposite side of patient attachment element 320 from which the conical tube engaging element 310 extends. FIGS. 6E-6T illustrate example manufacturing constructional layers of each of the above adhesive arrangements.

Such layers may also include an absorption layer 340, which may collect, absorb, or otherwise contain residues, bodily fluids, excess adhesive, or other containments that it may come into contact with. By absorbing unwanted contaminants, the absorption layer 340 further reduces the risk of infection at the entry point of the catheter by reducing the amount of non-sterile contact the entry point may come into contact with. Such layers may also include an antibacterial or antimicrobial layer 350, which may include conventional antibacterial or antimicrobial substances to further reduce the risk of infection and/or presence of bacterial or microbial contaminants. In some but not necessarily all embodiments, where such absorption layer 340 and/or antimicrobial layer 350 are not shown, e.g., FIGS. 6E-6T, tube stabilization patch 300 may still include one or both such layers 340, 350.

Patient attachment element 320 may include an adhesive, magnetic, or structural elements to provide a detachable connection with medical garment 100. In such embodiments, medical garment 100 may include complementary surfaces that may allow for an adhesive, magnetic, or structural element to adhere to the medical garment. This may assist keeping the tube stabilization patch in a comfortable place on the patient.

Patient attachment element 320 may also include a pull tab 360 for easy removal of the tube stabilization patch 300, such that the patient may apply retracting pressure to the pull tab 360 to separate the adhesive from the patient, allowing for easy removal.

Tube stabilization patch 300 may include an access separation 370. The access separation 370 may allow for attachment or detachment of tube stabilization patch 300 from around the medical tubing or catheter. Access separation 370 may extend from openable bore 316 of tube engaging element 310 to an edge of patient attachment element 320. Such an extension may cut through a radial line of the patient attachment element from, through, and including the innermost wall surface 315 of tube engaging element 310, to, through and including an external perimeter of patient attachment element 320. Access separation 370 may also cut through all or a portion of the plurality of layers 320, allowing for a medical tube or catheter to be passed through the separation and secured by the tube engaging element, without removing the catheter.

Moreover, the access separation 370 slit may be a straight line cut through patient attachment element 320 that extends up in a straight line through one side of extending portion 314,314a for example as shown in FIG. 6A. However, the present disclosure is not so limited. For example, access separation 370 may also, or alternatively, comprise, or cut, a wavy (e.g., sinusoidal) line, or slit, along patient attachment element 320. Access separation 370 may also extend up in a similarly wavy (e.g., sinusoidal) line through one side of extending portion 314,314a for example as shown in FIG. 6B. However, combinations of straight line and wavy line cuts for access separation 370 are also contemplated (e.g., straight line cut through patient attachment element 320 and wavy line cut through one side of extending portion 314,314a, or vice versa).

At least a portion of access separation 370, especially the portion extending through one side of extending portion 314,314a, being wavy may further provide a graded release or holding force for the medical tubing or catheter within extending portion 314,314a. Such a wavy character forms smooth, continuous, undulating and interlocking "finger" like extensions at the mating edges of the sidewall of extending portion 314,314a along facing sides of access separation 370. As the mating edges of the sidewall of extending portion 314,314a along each side of access separation 370 separate from one another, these interlocking "finger" like extensions flex outward and, gradually, less and less of the inner surface area of these "finger" like extensions are in direct physical contact with the perimeter of the medical tubing or catheter as the medical tubing or catheter is pulled out of extending portion 314,314a along separated access separation 370.

Accordingly, a medical tube or catheter may be pulled, from an outer edge of tube stabilization patch 300 at a terminal end of access separation 370, toward a center of the bore of tube engagement element 310. Accordingly, the medical tube or catheter, extending roughly perpendicular to the surface of patient attachment element 320, will travel within and along access separation 370 toward tube engaging element 310 until the diameter of the medical lube or catheter between facing edges of access separation 370 causes the portion of access separation 370 intersecting the cone-shaped side of the bore of tube engagement element 310 to separate sufficiently to allow the medical tube or catheter to slip into the center of the bore of tube engagement element 310. The medical lube or catheter slipping into the center of the bore of lube engagement element 310 causes the portion of access separation 370 intersecting the cone-shaped side of the bore of tube engagement element 310 to entirely close (forming the previously-described "O" shape), or almost entirely close where the diameter of the medical tubing significantly exceeds the resting inside diameter(s) of bore 316 (forming the previously-described "C" shape), thereby, providing an automatically adjusting interference fit with an array of different catheter sizes by ensuring substantially the entirety of the inner wall of bore 316 of tube engagement element 310 is in direct physical contact and exerting a substantially equal pressure about an entire, or substantially entire, uninterrupted perimeter of the medical tubing or catheter. Because this direct physical contact exerts a substantially equal pressure about an entire, or substantially entire, perimeter of the medical tubing or catheter, because tube engagement element 310 has a tapering, cone type shape with sidewalls that thin toward the tip of the cone, and because a portion of access separation 370 intersects the cone-shaped side of the bore of tube engagement element 310, these features work together so that this substantially equal pressure distributed about an entire perimeter of the medical tubing or catheter is sufficient to immobilize the medical tubing or catheter within tube engagement element 310, while simultaneously actually being incapable of (e.g., insufficiently large for) closing off, or even physically deforming (e.g., bending, kinking) the catheter lumen, by accident or intention.

In fact, these features working together to distribute this substantially equal pressure about an entire perimeter of a variation of sizes of medical tubing or catheters actually directly prevents such physical deformation of the catheter lumen. Moreover, the passive securing provided by the direct physical contact exerting a substantially equal pressure about an entire perimeter of the medical tubing or catheter, coupled with the portion of access separation 370 intersecting the cone-shaped side of the bore of tube engagement element 310, is automatically releasable simply by pulling on one side of access separation 370 (or a pull tab 360 ultimately coupled thereto, or even by pulling on a lower edge of third flap 124 of garment 100 when tube stabilization patch 300 is adhesively disposed over third flap 124 such that access separation 370 extends coextensively with and directly over and along the lower edge of third flap 124, see, e.g., FIG. 14) until the medical tubing or catheter is released from the conical bore of tube engagement element 310.

This is all in direct contrast to any prior solutions that utilize clamps, clamping elements, discrete multi-point gripping elements, manually locking and unlocking ratcheting features, or any element(s) that, alone or collectively when combined with any other features, act to pinch or otherwise secure the catheter by applying force to the catheter walls in any manner other than with substantially equal pressure about an entire, or substantially entire, uninterrupted perimeter of the medical tubing. This required manual disengagement of such clamps, clamping elements, discrete multi-point gripping elements is also a legitimate challenge for elderly patients, who lack sufficient dexterity and motor coordination in their fingertips to properly disengage such ratchets without causing significant, undesirable and potentially dangerous relative motion between the catheter and the patient's body, FIGS. 6E-6I illustrate various layers of a first configuration of tube stabilization patch 300, according to some example embodiments. FIG. 6E illustrates an exploded isometric view of the first configuration of tube stabilization patch 300 as viewed from the top. FIG. 6F illustrates an exploded isometric view of the first configuration of tube stabilization patch 300 as viewed from bottom. FIG. 6G illustrates a side view of the assembled first configuration of tube stabilization patch 300. FIG. 6H illustrates an isometric view of the assembled first configuration of tube stabilization patch 300 as viewed from the top. And FIG. 6I illustrates an isometric view of the assembled first configuration of tube stabilization patch 300 as viewed from the bottom.

In the first configuration of tube stabilization patch 300, the backside of patient attachment element 320 comprises an adhesive, and tube stabilization patch 300 is configured for adhesive coupling directly to garment 100 or directly to the skin of the patient. As shown, patient attachment element 320 comprises a cover layer 321, a base layer 323 and a bottom layer 325, which together sandwich tube engagement element 310 therebetween.

Cover layer 321 is disposed over and in direct physical contact with the top surface of tube engagement element 310. Cover layer 321 has a substantially circular form factor. Cover layer 321 comprises an aperture 322 configured such that extending portion 314,314a of tube engagement element 310 extends therethrough. Cover layer 321 also comprises access separation 370 cutting therethrough from aperture 322 all the way to a perimeter of cover layer 321. A bottom surface of cover layer 321 comprises an adhesive, while a top surface of cover layer 321 does not comprise an adhesive. Accordingly, the bottom side of cover layer 321 is configured to adhere directly to the top surface of tube engagement element 310 and, peripherally of tube engagement element 310, to a top surface of base layer 323 as well.

Base layer 323 is disposed under and in direct physical contact with the bottom surface of tube engagement element 310. Base layer 323 also comprises an aperture 324 configured to provide unobstructed access to bore 316 of tube engagement element 310 from the backside. Base layer 323 also comprises access separation 370 cutting therethrough from aperture 324 all the way to a perimeter of base layer 323. A bottom surface of base layer 323 comprises an adhesive, while a top surface of base layer 323 does not comprise an adhesive. Accordingly, the bottom side of base layer 323 is configured to adhere directly to the top surface of a bottom layer 325 and, peripherally of the top surface of bottom layer 325, to either an outer surface of garment 100 or directly to the skin of the patient.

Bottom layer 325 is disposed under and in direct physical contact with the bottom surface of base layer 323. Bottom layer 325 also comprises an aperture 326 configured to provide unobstructed access to bore 316 of tube engagement element 310 from the backside. Bottom layer 325 also comprises access separation 370 cutting therethrough from aperture 326 all the way to a perimeter of bottom layer 325. A top surface of bottom layer 325 comprises an adhesive, while a bottom surface of bottom layer 325 does not comprise an adhesive. Accordingly, the top side of bottom layer 325 is configured to adhere directly to the bottom surface of base layer 323. And the bottom surface of bottom layer 325 is configured to be disposed directly against either the outer surface of garment 100 or directly to the skin of the patient while the bottom surface of base layer 323, peripherally of the top surface of bottom layer 325, is adhered either to the outer surface of garment 100 or directly to the skin of the patient.

When tube stabilization patch 300 is manufactured and tube engagement element 310 and layers 321, 323, 325 are properly assembled, apertures 322, 324, 326 and bore 316 of tube engagement element 310 are all aligned with one another such that an unobstructed path through tube stabilization patch 300 exists therethrough.

FIGS. 6J-6N illustrate various layers of a second configuration of tube stabilization patch 300, according to some example embodiments. FIG. 6J illustrates an exploded isometric view of the second configuration of tube stabilization patch 300 as viewed from the top. FIG. 6K illustrates an exploded isometric view of the second configuration of tube stabilization patch 300 as viewed from bottom. FIG. 6L illustrates a side view of the assembled second configuration of tube stabilization patch 300. FIG. 6M illustrates an isometric view of the assembled second configuration of tube stabilization patch 300 as viewed from the top. And FIG. 6N illustrates an isometric view of the assembled second configuration of tube stabilization patch 300 as viewed from the bottom.

As with the first configuration, in the second configuration of tube stabilization patch 300, the backside of patient attachment element 320 comprises an adhesive, and tube stabilization patch 300 is configured for adhesive coupling directly to garment 100 or directly to the skin of the patient. As shown, patient attachment element 320 omits cover layer 321 from the first configuration but comprises base layer 323 and bottom layer 325, which together sandwich tube engagement element 310 therebetween without the need for cover layer 321 as previously described.

Accordingly, rather than being disposed under and in direct physical contact with the bottom surface of tube engagement element 310, base layer 323 is disposed over and in direct physical contact with the top surface of tube engagement element 310. Base layer 323 also comprises aperture 324, here, configured such that extending portion 314,314a of tube engagement element 310 extends therethrough. Base layer 323 also comprises access separation 370 cutting therethrough from aperture 324 all the way to a perimeter of base layer 323. The bottom surface of base layer 323 comprises an adhesive, while the top surface of base layer 323 does not comprise an adhesive. Accordingly, the bottom side of base layer 323 is configured to adhere directly to the top surface of tube engagement element 310 and, peripherally of tube engagement element 310, to either an outer surface of garment 100 or directly to the skin of the patient.

Bottom layer 325 is disposed under and in direct physical contact with the bottom surface of tube engagement element and, peripherally of tube engagement element 310, to base layer 323. Bottom layer 325 also comprises aperture 326 configured to provide unobstructed access to bore 316 of tube engagement element 310 from the backside. Bottom layer 325 also comprises access separation 370 cutting therethrough from aperture 326 all the way to a perimeter of bottom layer 325. A top surface of bottom layer 325 comprises an adhesive, while a bottom surface of bottom layer 352 does not comprise an adhesive to prevent accidental adhesion to sensitive skin areas. Accordingly, the top side of bottom layer 325 is configured to adhere directly to the bottom surface of base layer 323. And the bottom surface of bottom layer 325 is configured to be disposed directly against either the outer surface of garment 100 or directly to the skin of the patient while the bottom surface of base layer 323, peripherally of the top surface of bottom layer 325, is adhered either to the outer surface of garment 100 or directly to the skin of the patient.

As with the first configuration, when the second configuration of tube stabilization patch 300 is manufactured and lube engagement element 310 and layers 323 and 325 are properly assembled, apertures 324 and 326 and bore 316 of tube engagement element 310 are all aligned with one another such that an unobstructed path through tube stabilization patch 300 exists therethrough.

FIGS. 6P-6T illustrate various layers of yet a third configuration of tube stabilization patch 300, according to some example embodiments. FIG. 6P illustrates an exploded isometric view of the third configuration of tube stabilization patch 300 as viewed from the top. FIG. 6Q illustrates an exploded isometric view of the third configuration of tube stabilization patch 300 as viewed from bottom. FIG. 6R illustrates a side view of the assembled third configuration of tube stabilization patch 300. FIG. 6S illustrates an isometric view of the assembled third configuration of tube stabilization patch 300 as viewed from the top. And FIG. 6T illustrates an isometric view of the assembled third configuration of tube stabilization patch 300 as viewed from the bottom.

Contrary to the first and second configurations, in the third configuration of tube stabilization patch 300, the frontside (or top side) of patient attachment element 320 comprises an adhesive, and tube stabilization patch 300 is configured for adhesive coupling directly to an inside, patient-facing surface of garment 100. As shown, patient attachment element 320 comprises a base layer 323 and a bottom layer 325, which together sandwich tube engagement element 310 therebetween without the need for a cover layer 321 as previously described.

Accordingly, rather than being disposed under and in direct physical contact with the bottom surface of tube engagement element 310, as in the first configuration, base layer 323 is disposed over and in direct physical contact with the top surface of tube engagement element 310. Base layer 323 also comprises aperture 324, here, configured such that extending portion 314,314a of tube engagement element 310 extends therethrough. Base layer 323 also comprises access separation 370 cutting therethrough from aperture 324 all the way to a perimeter of base layer 323. The top surface of base layer 323 comprises an adhesive, while the bottom surface of base layer 323 does not comprise an adhesive. Accordingly, the top side of base layer 323 is configured to adhere directly to the inner, patient-facing surface of garment 100.

Bottom layer 325 is disposed under and in direct physical contact with the bottom surface of tube engagement element 310 and, peripherally of tube engagement element 310, to base layer 323. Bottom layer 325 also comprises aperture 326 configured to provide unobstructed access to bore 316 of tube engagement element 310 from the backside. Bottom layer 325 also comprises access separation 370 cutting therethrough from aperture 326 all the way to a perimeter of bottom layer 325. The top surface of bottom layer 325 comprises an adhesive, while the bottom surface of bottom layer 352 does not comprise an adhesive. Accordingly, the top side of bottom layer 325 is configured to adhere directly to the bottom surface of tube engagement element 310 and, peripherally of tube engagement element 310, to base layer 323. And the bottom surface of bottom layer 325, as well as the bottom surface of base layer 323 peripherally of the top surface of bottom layer 325, are configured to be disposed directly against the skin of the patient.

As with the first and second configurations, when the third configuration of tube stabilization patch 300 is manufactured and tube engagement element 310 and layers 323 and 325 are properly assembled, apertures 324 and 326 and bore 316 of tube engagement element 310 are all aligned with one another such that an unobstructed path through tube stabilization patch 300 exists therethrough.

Figure 7B:
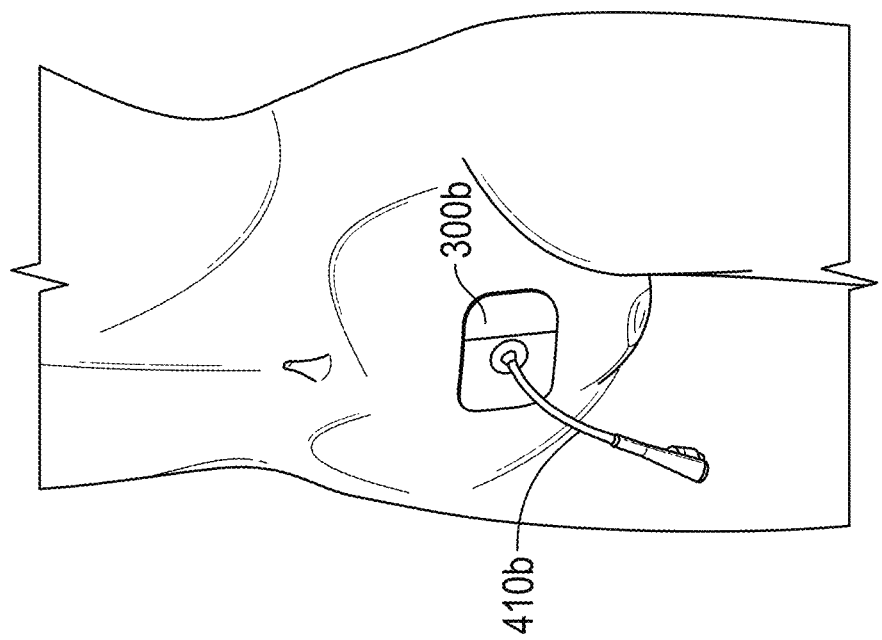
FIGS. 7A-7B are example views of patients with suprapubic or ileostomy catheters secured by a tube stabilization patch of a device or system for stabilizing medical tubing protruding from a patient, according to embodiments of the present disclosure.
Figure 7A:
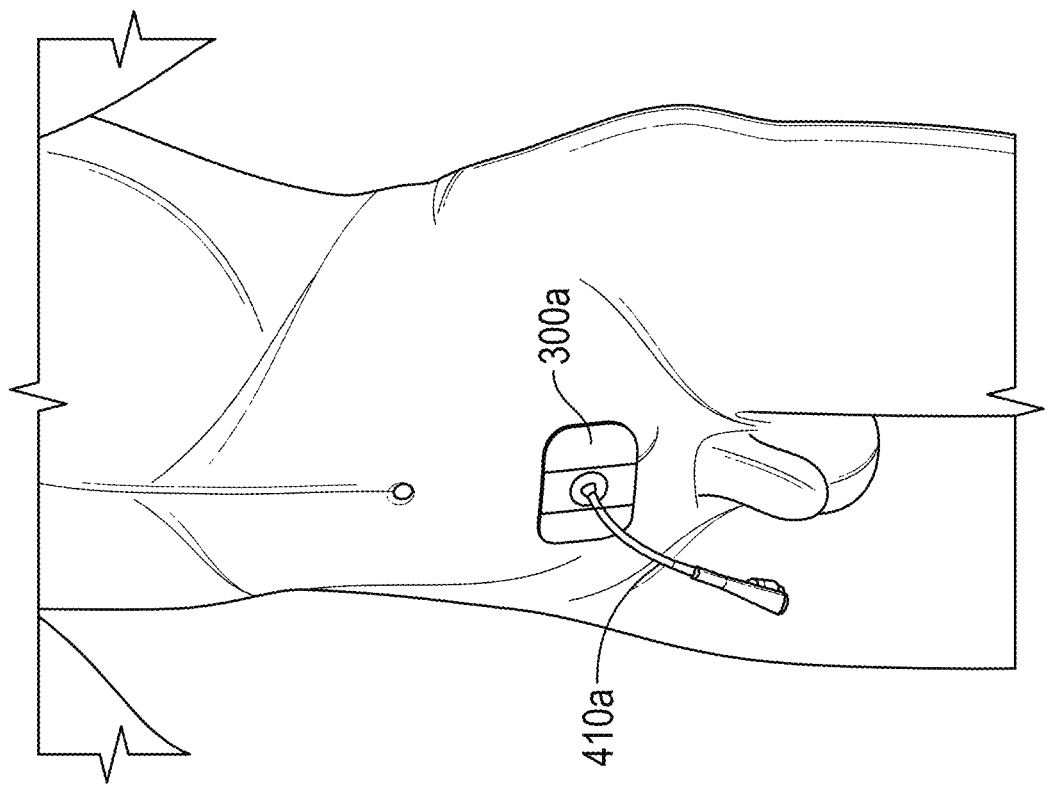

FIGS. 7A-7B are example views of patients with suprapubic or ileostomy catheters secured by a tube stabilization patch of a device or system for stabilizing medical tubing protruding from a patient, according to embodiments of the present disclosure.

According to various embodiments of the present disclosure, the tube stabilization patch 300a, 300b may be attached to a catheter and secured on the body of the patient. As depicted in FIGS. 7A-7B, the tube stabilization patch may be used with a variety of different types of medical lubing and/or catheters (i.e., suprapubic or ileostomy catheters 410a, 410b). The lube stabilization patch 300 may be separated at the access separation 370 (see, e.g., FIGS. 6A-6B) and slid over the medical tubing or catheter without removing the medical tubing or catheter or disconnecting the medical tubing or catheter from any drainage bags. Once it is slid over the medical tubing or catheter, tube stabilization patch 300a. 300b may be secured or adhered to the body of the patient by removing the adhesive backing (330, FIGS. 6A-6B).

Tube stabilization patch 300 reduces the amount of relative movement when worn by preventing the medical tubing or catheter from moving in and out (pistoning) of the patient and adding further rigidity to the lateral movement of the medical tubing or catheter due to the stiffer tube engaging element 310 (see, e.g., FIGS. 6A-6D). In some embodiments, tube engaging element 310 may be more rigid than conventional medical tubing or catheters. In some embodiments, tube engaging element 310 may be less rigid than conventional medical tubing or catheters to aid in prevention of crimping or otherwise deforming the lumen of medical tubing and/or catheters disposed therein.

In various embodiments, once the medical tubing, for example, an in-dwelling catheter, is positioned in the patient, tube engagement element 310 may be attached to the tube, for example by securing it around the medical tubing at a location at or near where the tubing exits the patient's body. The patient attachment element, which may be peripherally secured to the circumference of the tube engaging element, may then be secured, via adhesive or similar, to the skin of the patient. In other words, once the medical tubing is positioned and secured in tube engaging element 310 of tube stabilization patch 300, tube stabilization patch 300 may be secured to the body of the patient.

The application of the tube stabilization patch 300 to suprapubic or ileostomy catheters in FIGS. 7A-7B is merely exemplary. One skilled in the art would understand how such a tube stabilization patch 300 may be applied to other medical tubing and/or catheters.

Figure 7D:
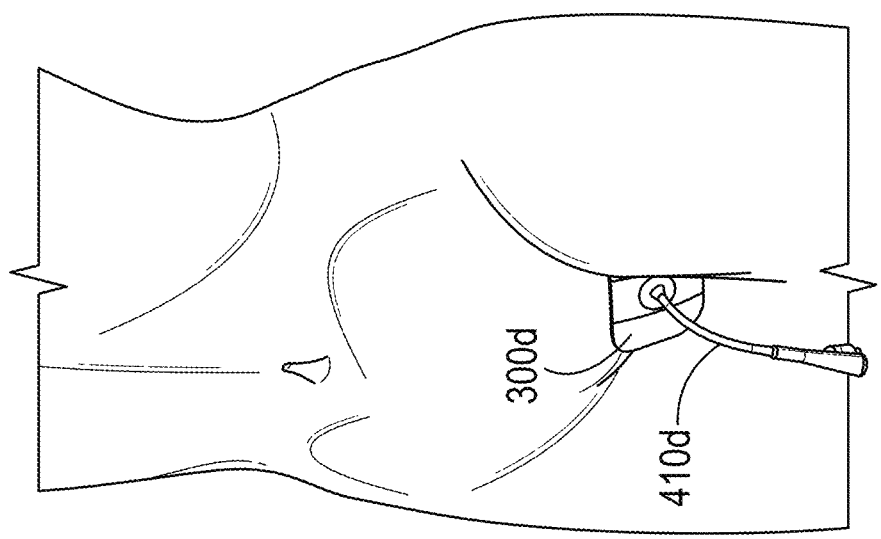
FIGS. 7C-7D are example views of patients with urethral catheters secured by a tube stabilization patch of a device or system for stabilizing medical tubing protruding from a patient, according to embodiments of the present disclosure.
Figure 7C:
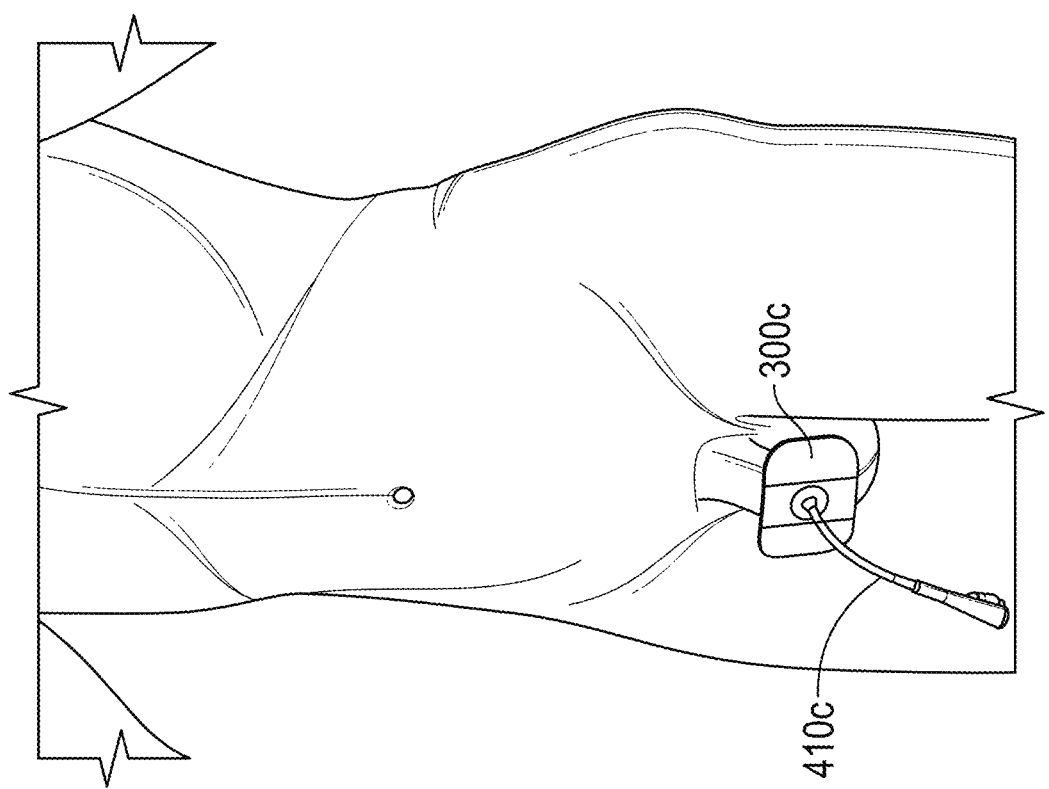

For example, FIGS. 7C-7D illustrate example views of patients with urethral catheters secured by a tube stabilization patch 300c, 300d of a device or system for stabilizing medical tubing protruding from a patient, according to embodiments of the present disclosure.

As shown in FIGS. 7C-7D, tube stabilization patch 300c, 300d may be attached to a urethral catheter and, ultimately, secured to an adjustable garment 100 (not shown in FIGS. 7C-7D, but see any garment 100 discussed or illustrated in this disclosure) and in an orientation, with respect to the body of the patient, substantially as shown in FIGS. 7C-7D. Accordingly, patches 300c, 300d in FIGS. 7C and 7D may illustrate the relative position of patches 300c, 300d with respect to the patient's body without the garment 100 illustrated, for easy viewing of the relative orientations. As depicted in FIGS. 7C-7D, tube stabilization patch 300c, 300d may be used with a variety of different types of medical tubing and/or catheters (i.e., urethral catheters 410c, 410d). Tube stabilization patch 300c, 300d may be separated at the access separation 370 (see, e.g., FIGS. 6A-6D) and slid over the medical tubing or catheter without removing the medical tubing or catheter or disconnected the medical tubing or catheter from any drainage bags. Once it is slid over the medical tubing or catheter, tube stabilization patch 300c, 300d may be secured or adhered to the adjustable garment 100 by removing a backing on the appropriate side of the appropriate layer having the adhesive for adhered to the adjustable garment 100 (see, e.g., FIGS. 6A-6T).

Discussion of utilizing garment(s) 100 in conjunction with tube stabilization patch(es) 300, for example, in a method of stabilizing medical tubing protruding from a patient, will now be discussed in connection with FIGS. 8-16 below.

Figure 8:
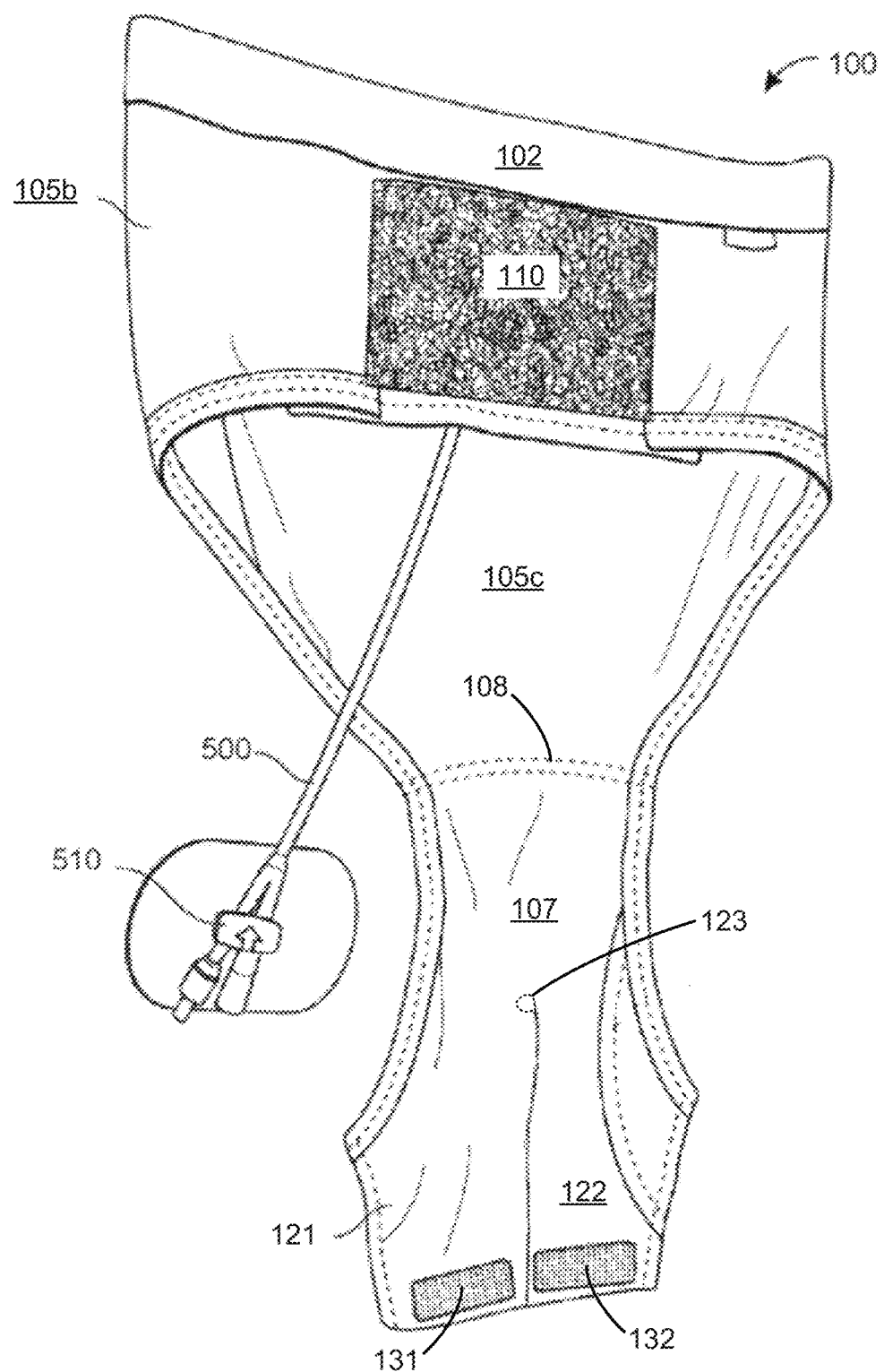
FIG. 8 is a perspective view of an example medical garment of a device or system for stabilizing medical tubing protruding from a patient with adjustable flaps in unattached positions and with example medical tubing protruding from a patient, according to embodiments of the present disclosure.

FIG. 8 is a front view of an example medical garment of a device or system for stabilizing medical tubing protruding from a patient having both first and second adjustable flaps 121, 122 in unattached positions, with example medical tubing 500 protruding from a patient (not shown in FIG. 8), according to embodiments of the present disclosure. FIG. 8 depicts an initial step of donning the medical tubing stabilization device. Such that, when the device is initially worn, the patient may don the medical garment 100, verify that the body of the medical garment 100 is secured around the lower abdomen of the patient, locate the adjustable flap portion 120 in preparation for locating and positioning vertex 123 and, so, catheter exit port 210, both vertically and horizontally with respect to other portions of garment 100, e.g., waistband 102 and/or body portion 105.

According to various embodiments of the present disclosure, medical garment 100 may be donned with medical tubing or a catheter 500 already in place. For example, a conventional Foley catheter (e.g., medical tubing or catheter 500) may have a Foley catheter securement device 510 that is secured or securable, e.g., to one of the patient's legs. In various embodiments, the present disclosure may work in conjunction with such a Foley catheter system. In one such example embodiment, the Foley catheter may be inserted by a medical professional. In some embodiments, catheter securement device 510 may then be attached to the patient, or catheter securement device 510 may be attached to the patient after garment 100 is donned. Medical garment 100 may be donned around the hips, waist, and lower abdomen of the patient, with the bottom of garment 100 entirely open, as shown in FIG. 8, with or without patch 300 already properly attached to garment 100. In some such embodiments, tube stabilization patch 300 may be secured around the medical tubing or catheter and adhesively secured to an inward, patient-facing surface of garment 100, between the body of the patient and garment 100 immediately opposite the location where the catheter or medical tubing exits the patient's body (see, e.g., FIGS. 11-13), or secured around the medical tubing or catheter and adhesively secured to an outward-facing surface of garment 100 immediately opposite the location where the catheter or medical tubing exits the patient's body after at least partial donning of garment 100 (see, e.g., FIG. 14).

Figure 9:
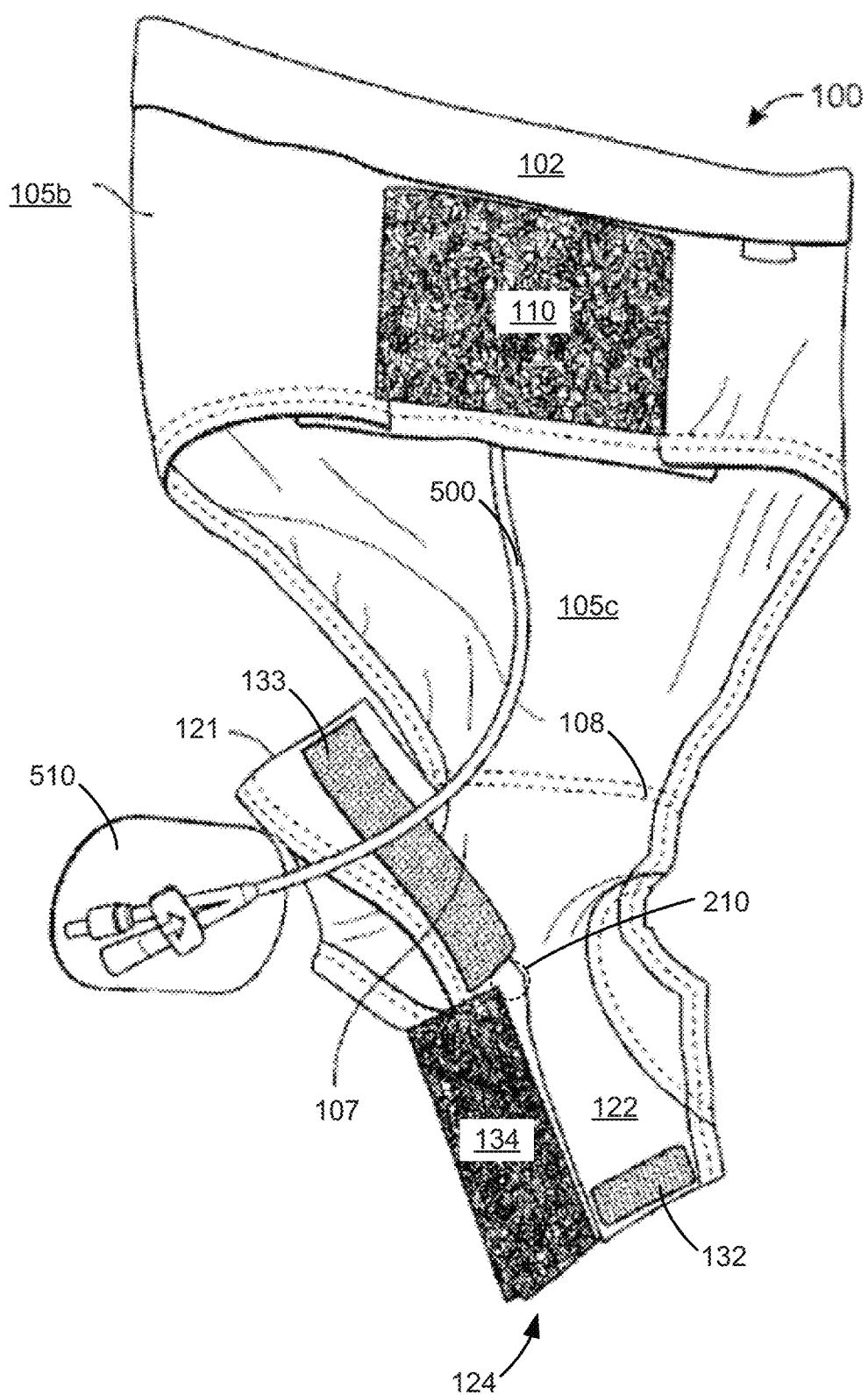
FIG. 9 is a perspective view of an example medical garment of a device or system for stabilizing medical tubing protruding from a patient with adjustable flaps in unattached positions, and separated from one another, and the example medical tubing protruding from a patient being passed between the adjustable flaps, according to embodiments of the present disclosure.

FIG. 9 is a perspective view of medical garment 100, for example partially donned by a patient as in FIG. 8, having both first and second adjustable flaps 121, 122 in unattached positions and first and second adjustable flaps 121, 122 separated from one another all the way down to location or vertex 123 to show the location that will become catheter exit point 210 once first and second adjustable flaps 121, 122 are adjustably coupled to the anterior portion 105a of body portion 105 of garment 100 and first and second adjustable flaps 121, 122 are coupled to one another by attaching third flap 124, which is hingedly attached at seam 125 to the outward-facing surface of second adjustable flap 122, to first adjustable flap 121. Here, the tucking of first adjustable flap 121 between the leg of the patient and catheter 500 (which may be secured to the leg by securement device 510) is what allows catheter 500 to get to the center of the garment, e.g., to location or vertex 123, which subsequently forms a portion of catheter exit port 210 without needing to disconnect securement device 510. Otherwise, catheter 500 would be trapped in one of the leg holes.

As illustrated in FIG. 9, the medical tubing or catheter 500, a first end of which is secured within the patient and a second end of which is shown to terminate at securement device 510, may be disposed between first and second adjustable flaps 121, 122 in preparation for adjustably attaching the first adjustable flap 121 to a first desired location on the anterior portion of body portion 105 of garment 100. Such disposition may occur by moving the medical tubing or catheter in between first and second adjustable flaps 121, 122 or by moving the first and second adjustable flaps 121, 122 until the medical tubing or catheter is disposed therebetween.

Figure 10:
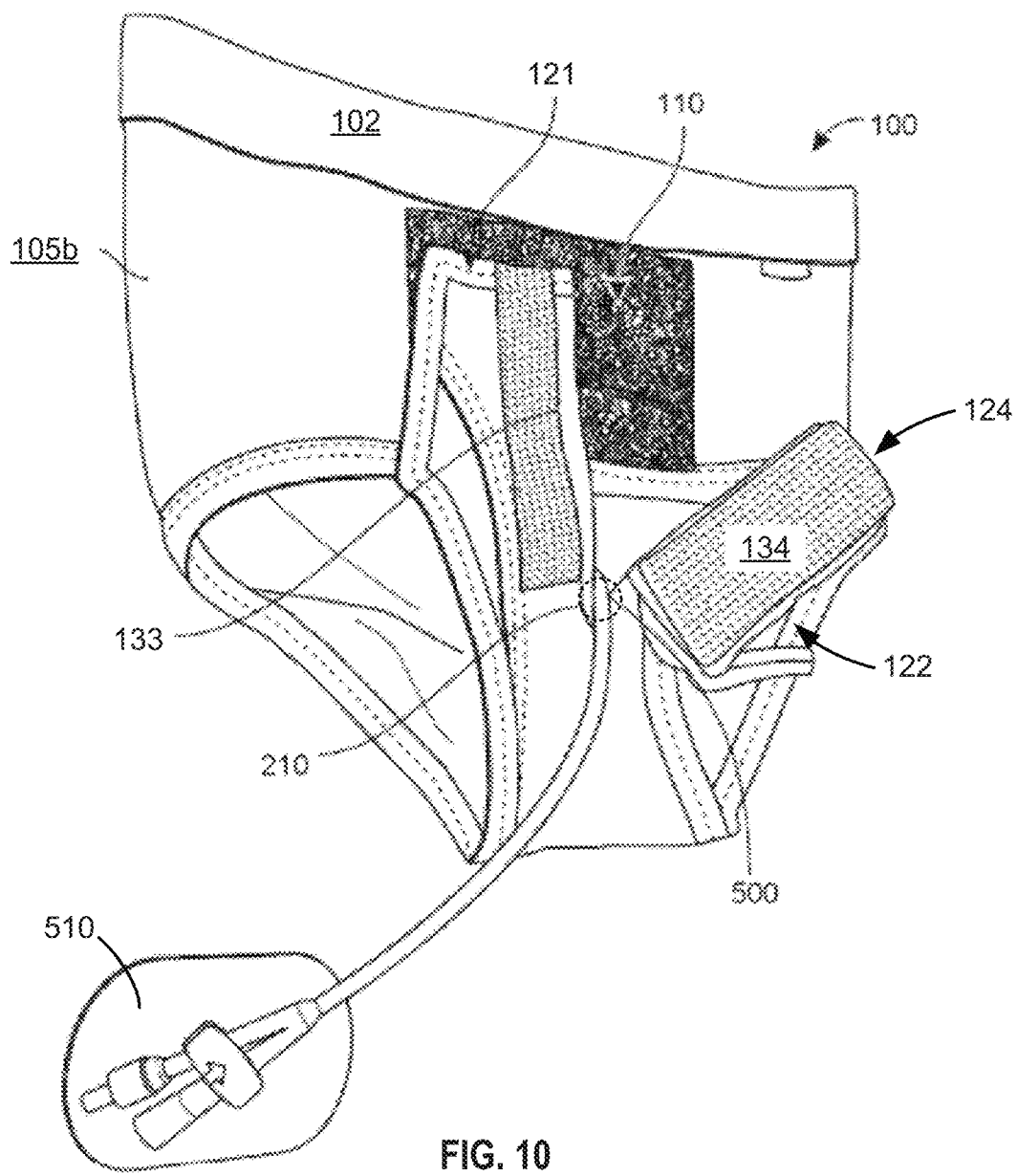
FIG. 10 is a perspective view of an example medical garment of a device or system for stabilizing medical tubing protruding from a patient with a first adjustable flap in an attached position, a second adjustable flap in an unattached position, and a third flap also in an unattached position, the example medical tubing protruding from a patient being passed between the first and second adjustable flaps, and situated at a catheter exit port, according to embodiments of the present disclosure.

FIG. 10 depicts a perspective view of medical garment 100 having first adjustable flap 121 in an attached position to the anterior portion of body portion 105 of garment 100, the medical tube or catheter 500 resting against the location or vertex 123, where catheter exit port 210 will be formed when second adjustable flap 122 is disposed in its attached position to the anterior portion of body portion 105 of garment 100, and third flap 124 is secured to and over first adjustable flap 121.

According to embodiments of the present disclosure, the medical tubing or catheter 500 may be disposed all the way down, between first and second adjustable flaps 121, 122, until the medical tubing or catheter 500 is disposed directly against the location or vertex 123, where catheter exit port 210 will be formed when second adjustable flap 122 is disposed in its attached position to the anterior portion of body portion 105 of garment 100, and third flap 124 is secured to and over first adjustable flap 121. The medical tubing or catheter 500 may be so disposed with tube stabilization patch 300 already attached around medical tubing or catheter 500 (for example, as shown and described in relation to FIG. 11 and/or as described anywhere in this disclosure) or without tube stabilization patch 300 yet attached around medical tubing or catheter 500, as depicted in FIG. 10. Accordingly, the arrangement depicted in FIG. 10 is merely exemplary of the path a medical tubing or catheter may take to be secured in the medical garment 100, it does not, however, limit the disclosure, which is only limited by the claims.

Accordingly, since medial edges 121a, 122a of first and second adjustable flaps 121, 122 both extend directly from vertex 123, in operation, the vertical position of vertex 123, and so, ultimately, of catheter exit port 210 with respect to, e.g., waistband 102 and/or body portion 105, is determined, first, by the vertical component of the attached position of first adjustable flap 121 to the anterior portion of body portion 105 of garment 100 and, then, by the attached position of second adjustable flap 122 to the anterior portion of body portion 105 of garment 100. For similar reasons, the horizontal position of vertex 123, and so, ultimately, of catheter exit port 210 with respect to, e.g., waistband 102 and/or body portion 105, is determined, first, by the horizontal component of the attached position of first adjustable flap 121 to the anterior portion of body portion 105 of garment 100 and, then, by the horizontal component of the attached position of second adjustable flap 122 to the anterior portion of body portion 105 of garment 100. Moreover, in some embodiments, by attaching second adjustable flap 122 at a slightly overlapping and slightly off-parallel orientation with respect to first adjustable flap 121, the horizontal position of location or vertex 123, and so of catheter exit port 210, with respect to, e.g., waistband 102 and/or body portion 105, and its relative size can be microadjusted. For example, the greater the degree of overlap of second adjustable flap 122 with first adjustable flap 121, the greater angle at which medial edges 121a, 122a of first and second adjustable flaps 121, 122 converge and, ultimately, overlap above location or vertex 123. Accordingly, the present solutions offer continuous, infinitely granular adjustment of the relative location of vertex 123 in all four directions (vertically up or down, horizontally to one side or the other with respect to the exit location of the medical tubing from the patient's body).

Figure 11:
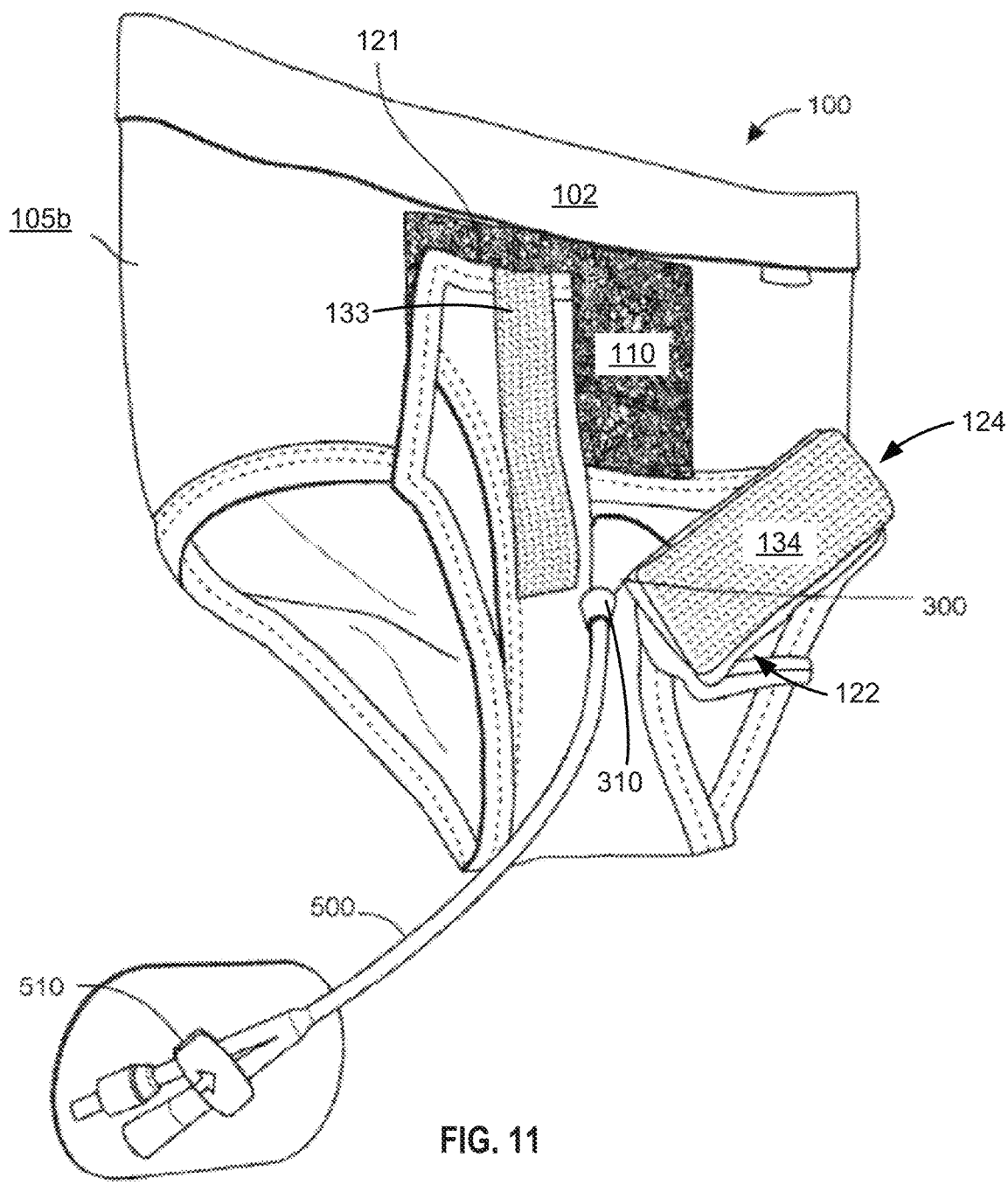
FIG. 11 is a perspective view of an example medical garment of a device or system for stabilizing medical tubing protruding from a patient with a first adjustable flap in an attached position, a second adjustable flap in an unattached position, and a third flap also in an unattached position, the example medical tubing protruding from a patient being passed through the tube stabilization patch disposed between the body of the patient and the medical garment, between the first and second adjustable flaps, and situated al a catheter exit port, according to embodiments of the present disclosure.

FIG. 11 depicts a perspective view of medical garment 100 in substantially the same orientation as in FIG. 10, however, where tube stabilization patch 300 is already attached around medical tubing or catheter 500.

Figure 12:
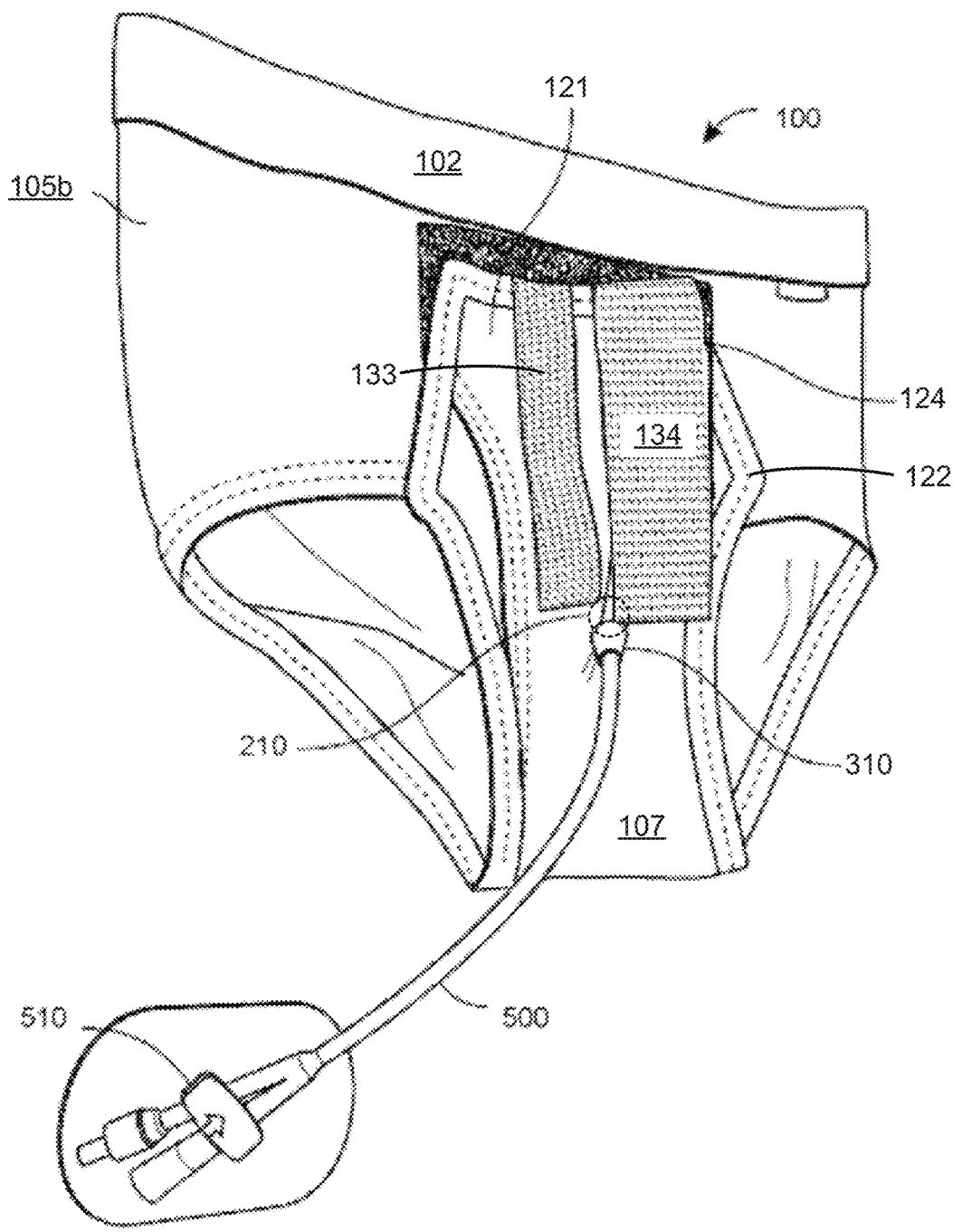
FIG. 12 is a perspective view of an example medical garment of a device or system for stabilizing medical tubing protruding from a patient with first and second adjustable flaps in attached positions and a third flap in an unattached position, the example medical tubing protruding from a patient being passed through the tube stabilization patch disposed between the body of the patient and the medical garment, between the first and second adjustable flaps, and situated at a catheter exit port, according to embodiments of the present disclosure.

According to various embodiments of the present disclosure, when tube stabilization patch 300 is secured around the medical tubing or catheter and placed between the patient's body and the inside, patient-facing surface of garment 100, and second adjustable flap 122 is disposed in its attached position to the anterior portion of body portion 105 of garment 100 (as shown in FIG. 12), and third flap 124 is then secured to and over first adjustable flap 121 (as shown in FIG. 13), tube engagement element 310 may protrude through the formed catheter exit port 210, such that the only portion of tube stabilization patch 300 that can be seen from the front of medical garment 100 is tube engaging element 310. After the tube stabilization patch 300 has been placed in the catheter exit port, second adjustment flap 122 may be fully attached to the body portion 105 of medical garment 100, as discussed in relation to FIG. 12.

FIG. 12 depicts a perspective view of medical garment 100 having second adjustable flap 122 further, now, also disposed in its attached position to the anterior portion of body portion 105 of garment 100, and third flap 124, which is hingedly attached at seam 125 to the outward-facing surface of second adjustable flap 122, yet in an unattached position with respect to first adjustable flap 121.

According to various embodiments of the present disclosure, once lube stabilization patch 300 has been placed at location or vertex 123, where catheter exit port 210 will be formed, second adjustable flap 122 is further, now, disposed in its attached position to the anterior portion of body portion 105 of garment 100.

FIG. 13 depicts a perspective view of medical garment 100 having first and second adjustable flaps 121, 122 disposed in their respective attached positions to the anterior portion of body portion 105 of garment 100, and third flap 124, which is hingedly attached at seam 125 to the outward-facing surface of second adjustable flap 122, now in an attached position to first adjustable flap 121.

According to various embodiments of the present disclosure, medical garment 100 may be fully donned with tube stabilization patch 300 in place, between the body of the patient and the inward, patient-facing surface of garment 100 as depicted in FIG. 13. And third flap 124, which is hingedly attached at seam 125 to the outward-facing surface of second adjustable flap 122, is now pivoted and/or hinged so as to be disposed in an attached position to and on first adjustable flap 121. By doing this, catheter exit port 210 is fully formed, with the medial edges of first and second adjustable flaps 121, 122 and the inner edge of vertex 123 disposed against the bottom and sides of the medical tubing or catheter, and the bottom edge or portion of third flap 124 disposed against the top of the medical tubing, catheter or, in FIG. 13 against lube engagement element 310, thereby each providing respective portions of the substantially equal pressure distributed about substantially an entire uninterrupted perimeter of the medical tubing, catheter or, in FIG. 13 against tube engagement element 310.

Figure 14:
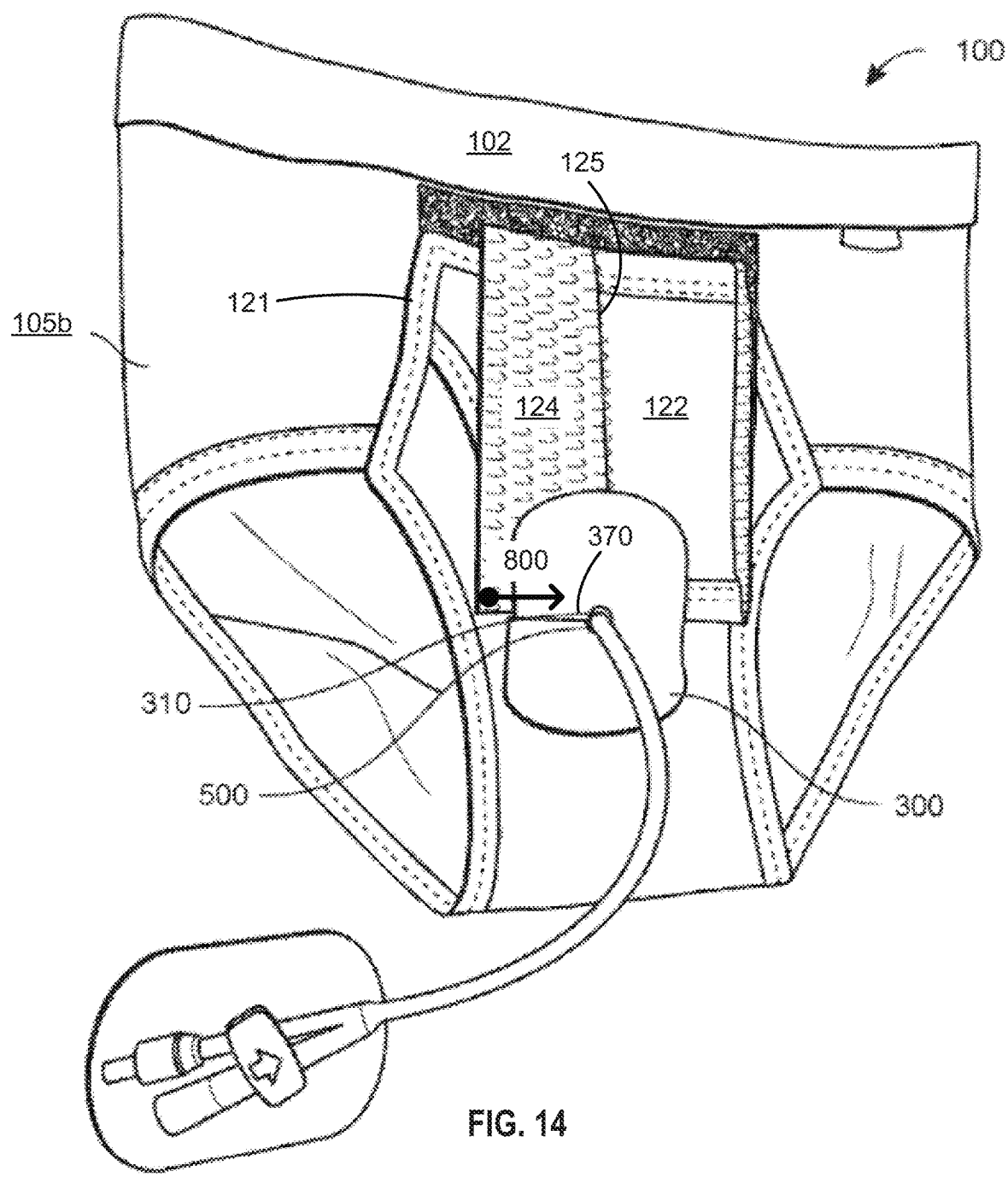
FIG. 14 is a perspective view of an example medical garment of a device or system for stabilizing medical tubing protruding from a patient with all flaps in attached positions, the example medical tubing protruding from a patient being passed through the garment before being passed through the tube stabilization patch, with the tube stabilization patch adhered to an external portion of the medical garment, according to embodiments of the present disclosure.

FIG. 14 depicts a perspective view of medical garment 100 with first, second and third flaps 121, 122 and 124 substantially as previously described in connection with FIG. 13, however, having medical tubing protruding from a patient passed through garment 100 before being passed through tube stabilization patch 300, which is adhered to an outside-facing, external portion of medical garment 100, according to embodiments of the present disclosure.

According to various embodiments of the present disclosure, the medical garment 100 may be partially or fully donned prior to the placement of tube stabilization patch 300. In such an embodiment, body portion 105 of medical garment 100 may be worn, and first and second adjustable flaps 121, 122 and third flap 124 may each be secured with catheter 500 disposed at location or vertex 123 and no tube stabilization patch 300 yet secured around catheter 500. Tube stabilization patch 300 may then be secured around the catheter 500 protruding from both the patient and the medical garment 100 and adhered to the external surface of medical garment 100.

According to various other embodiments of the present disclosure, placement of tube stabilization patch 300 on medical garment 100 may occur before garment 100 is donned by the patient. In such an embodiment, body portion 105 of medical garment 100 may be worn, and first and second adjustable flaps 121, 122 and third flap 124 may each be secured with catheter 500 disposed at location or vertex 123 with tube stabilization patch 300 already properly adhesively secured to garment 100. Tube stabilization patch 300 may then be secured around the catheter 500 protruding from both the patient and the medical garment 100 after being adhered to the external surface of medical garment 100.

As shown in FIG. 14, patch 370 may be secured to the outside of garment 100 in a specific orientation that allows automatic releasing of tube stabilization patch 300 from around the medical tubing or catheter simultaneously and in the same motion as the detaching of third flap 124 from the outward-facing surface of first adjustable flap 121. Specifically, tube stabilization patch 300 is coupled around the medical tubing or catheter 500 and adhesively disposed over properly-attached third flap 124 such that access separation 370 extends coextensively with, along, and directly over the lower edge of third flap 124. Accordingly, simply directly gripping the lower corner of properly-attached third flap 124 (e.g., shown at the bottom left of third flap 124 in FIG. 14) and pulling horizontally, for example, in the direction of arrow 800, will simultaneously release third flap 124 from first adjustable flap 121 and, as third flap 124 peels away from first adjustable flap 121, the lop portion of patient attachment element 320 above access separation 370 being adhered to third flap 124 and the bottom portion of patient attachment element 320 below access separation 370 being adhered to first adjustable flap 121 and/or perineum portion 107 disposed there-below, causes the facing edges of access separation 370 to separate both along patient attachment element 320 and along tube engagement element 310 until the medical tubing or catheter 500 simply falls out of the extending portion 314,314a of tube engagement element 310 when the sidewalls of bore 316 are sufficiently separated. Accordingly, embodiments of the present disclosure may allow for easy, pain-free single-action passive disengaging of garment 100 and tube stabilization patch 300, as described anywhere herein.

In yet other embodiments, since the ultimate exit location of the medical tubing from garment 100 is known in advance (e.g., location and/or vertex 123, which forms a part of aggregate catheter exit port 210) patch 300 may be adhesively secured to garment 100 before the patient dons garment 100. In some cases, this may be easier for elderly patients, or for patients for whom this is a first time experience. Moreover, since access separation 370 of patch 300 is configured to be adhesively disposed over third flap 124 such that access separation 370 extends coextensively with and directly over and along the lower, horizontal edge of third flap 124, see, e.g., FIG. 14), so disposing patch 300 on garment 100 before garment 100 is donned by the patient may ensure proper alignment of access separation 370 and hinged flap 124.

By contrast, if any other type of tube stabilization patch is not properly removed from the garment beforehand, removal of garment 100, with the catheter still attached to the patient, would pull on the catheter, causing a dangerous, accidental, forceful removal of the catheter from the patient.

In some embodiments, assuming catheter 500 is already inserted into the patient and secured to the leg with securement device 510, a system comprising garment 100 and patch 300 may operate in any of the following ways. The patient may first put on garment 100 and then secure patch 300 to the external surface of garment 100. The patient may first secure patch 300 to the external surface of garment 100 and then put on garment 100. The patient could first put on garment 100 and then secure place patch 100 to an inward, patient-facing surface of garment 100. The patient may alternatively first place the patch on the inward, patient-facing surface of garment 100 and then don garment 100. FIG. 11 illustrates patch 300 on such an inward, patient-facing surface of garment 100.

Figure 15:
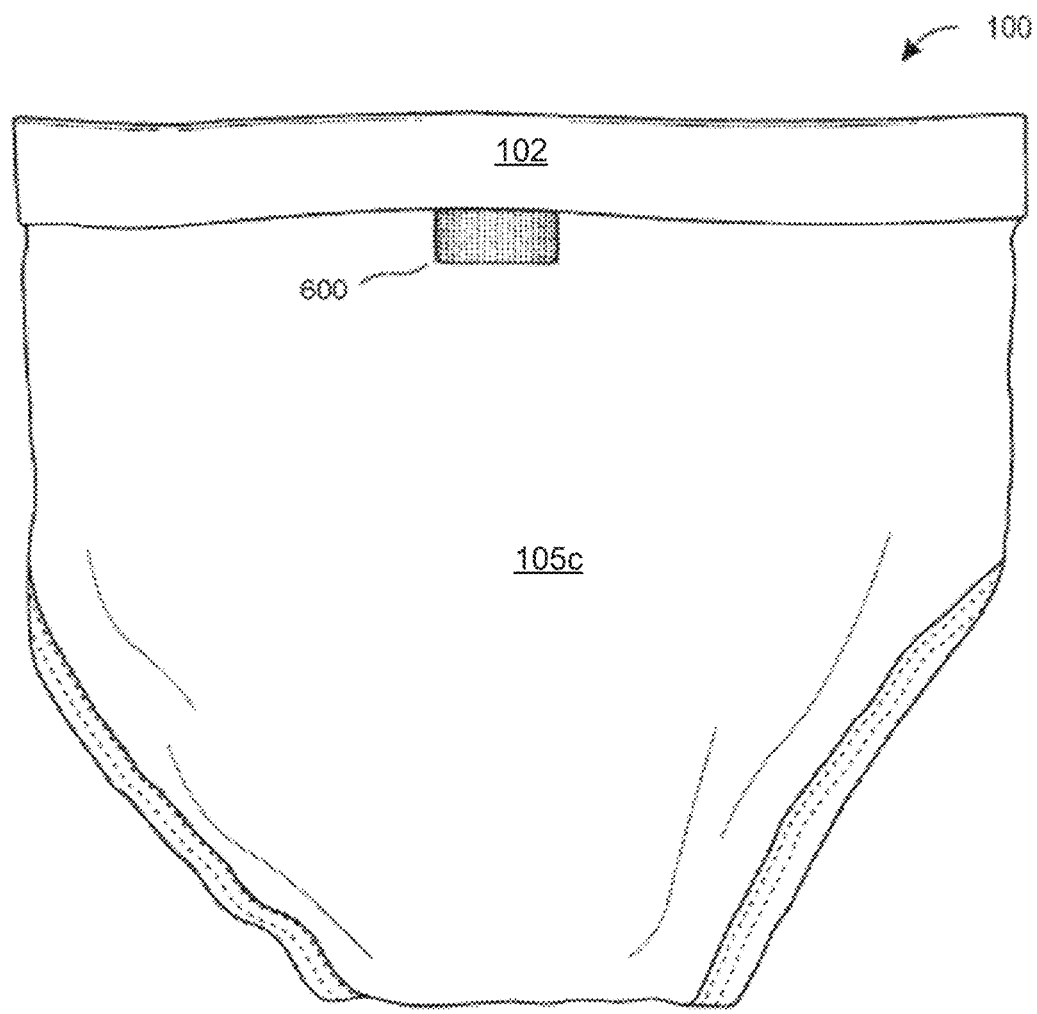
FIG. 15 is a rear view of an example medical garment of a device or system for stabilizing medical tubing protruding from a patient with a posterior attachment member, according to embodiments of the present disclosure.

FIG. 15 depicts a rear view of medical garment 100 having a posterior attachment member 600, according to embodiments of the present disclosure. According to various embodiments of the present disclosure, medical garment 100 may include such a posterior attachment member 600. Posterior attachment member 600 may be a section of the posterior or rear portion of medical garment 100. For example, posterior attachment member 600 may be centrally located on the rear portion of medical garment 100 or located in the middle-upper region of medical garment 100 (e.g., disposed approximately below encircling waistband 102 and approximately in the lateral center). Posterior attachment member 600 may have a width and height, which may be the same or different. For example, the width may be 2 inches and the height may be 1 inch. The posterior attachment member 600 may be a conventional hook and loop method, Velcro, reusable adhesive, and/or any other suitable method for repeatably attaching fabrics to one another.

Posterior attachment member 600 can hold or attach the adjustable flap portion 120 (e.g., first and/or second adjustable flaps 121, 122) to the rear portion of medical garment 100 to allow the patient wearing medical garment 100 to use the restroom, or otherwise access under medical garment 100 without having to entirely remove medical garment 100, remove the medical tubing or catheter, or disconnect the catheter from a drainage bag.

Figure 16:
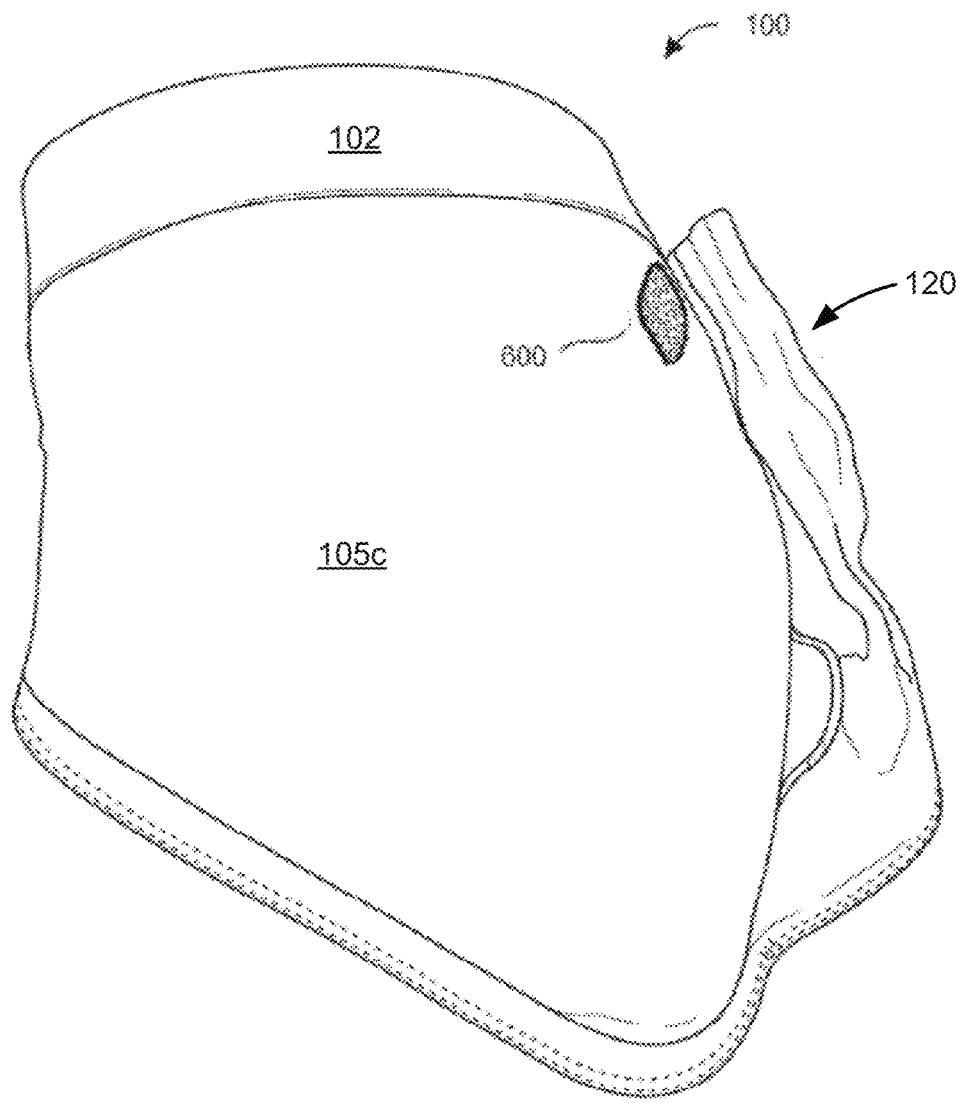
FIG. 16 is a side view of an example medical garment of a device or system for stabilizing medical tubing protruding from a patient with an adjustable flap attached to the posterior attachment member, according to embodiments of the present disclosure.

FIG. 16 depicts a side view of medical garment 100 with adjustable flap portion 120 attached to posterior attachment member 600, according to embodiments of the present disclosure. According to various embodiments of the present disclosure, medical garment 100 may have adjustable flap portion 120 pulled between the legs of the patient, from where it attaches on the body (not shown) to the rear portion of the body where it can be attached to posterior attachment member 600.

The medical tubing stabilization device may decrease the level of relative movement of medical tubing and catheters by stabilizing lateral, internal, and piston movement through the application of a tube stabilization patch and the further securing of the tube stabilization patch with the medical garment, as described in relation to various embodiments of the present disclosure.

While various embodiments of the present disclosure have been described above, it should be understood that they have been presented by way of example only, and not of limitation. Likewise, the various diagrams may depict an example architectural or other configuration for the disclosure, which is done to aid in understanding the features and functionality that can be included in the disclosure. The disclosure is not restricted to the illustrated example architectures or configurations, but the desired features can be implemented using a variety of alternative architectures and configurations. Indeed, it will be apparent to one of skill in the art how alternative functional, logical, or physical partitioning and configurations can be implemented to implement the desired features of the present disclosure. Also, a multitude of different constituent module names other than those depicted herein can be applied to the various partitions. Additionally, with regard to diagrams, operational descriptions, and method claims, the order in which the steps are presented herein shall not mandate that various embodiments be implemented to perform the recited functionality in the same order unless the context dictates otherwise.

Although the disclosure is described above in terms of various embodiments and implementations, it should be understood that the various features, aspects, and functionality described in one or more of the individual embodiments are not limited in their applicability to the particular embodiment with which they are described, but instead can be applied, alone or in various combinations, to one or more of the other embodiments of the disclosure, whether or not such embodiments are described and whether or not such features are presented as being a part of a described embodiment. Thus, the breadth and scope of the present disclosure should not be limited by any of the above-described embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "typical," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "element" does not imply that the components or functionality described or claimed as part of the element are all configured in a common package. Indeed, any or all of the various components of an element can be combined in a single package or separately maintained and can further be distributed in multiple groupings or packages or across multiple locations.

Additionally, the various embodiments set forth herein are described in terms of exemplary diagrams, flow charts, and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

The invention claimed is:

1. A medical tubing stabilization device, comprising:
a reusable adjustable medical garment, comprising:
a body portion configured to provide continuous, direct physical contact with immediately facing portions of a waist, a hips, a buttocks and a lower abdominal area of a patient;
a perineal portion extending from an edge of the body portion a predetermined distance to a vertex;
a first adjustable flap extending from an edge of the perineal portion that is to a first side of the vertex, to an end of the first adjustable flap that is configured to be adjustably coupled to a first location on the body portion;
a second adjustable flap extending from an edge of the perineal portion that is to a second side of the vertex opposite the first side, an end of the second adjustable flap that is configured to be adjustably coupled to a second location on the body portion; and
a third flap coupled to an outward-facing surface of the second adjustable flap and configured to hinge about a medial edge of the second adjustable flap and to releasably couple to an outward-facing surface of the first adjustable flap immediately adjacent to the vertex,
wherein the vertex extends to form the medial edge of the second adjustable flap and a medial edge of the first adjustable flap such that, when the third flap is disposed directly on the outward-facing surface of the first flap, an exit port is formed as an aperture having sidewalls entirely formed from the vertex, the medial edges of the first and second adjustable flaps immediately extending from the vertex, and an edge of the third flap immediately adjacent to the vertex.

2. The medical tubing stabilization device of claim 1, further comprising:
a disposable tube stabilization patch, comprising:
a tube engaging element having a circular bore configured to physically stabilize a portion of medical tubing having a circular perimeter by providing direct physical contact having a substantially equal pressure about the entire perimeter of the medical tubing when disposed within the circular bore;
a patient attachment element coupled to and surrounding the tube engaging element; and
an access separation extending continuously from an outer edge of the patient attachment element to the circular bore of the tube engaging element, wherein the tube engagement element is configured to receive the medical tubing by passing the medical tubing through the access separation to the tube engaging element.

3. The medical tubing stabilization device of claim 2, wherein the tube engagement element comprises:
a base; and
an extending portion extending from the base, the circular bore extending entirely through the base and the extending portion and having an inner wall that tapers as it extends away from the base.

4. The medical tubing stabilization device of claim 3, wherein the access separation comprises a cut extending in a wavy line from the outer edge of the patient attachment element to the circular bore of the tube engaging element, thereby forming smooth, continuous, undulating and interlocking extensions at mating edges of the extending portion of the tube engagement element along the access separation.

5. The medical tubing stabilization device of claim 4, wherein the interlocking extensions are configured to flex outward as the medical tubing is removed from the extending portion through the access separation and the mating edges of the extending portion separate, so that a decreasing amount of an inner surface area of the extensions are in direct physical contact with the perimeter of the medical tubing as the medical tubing is removed from the extending portion through the access separation.

6. The medical tubing stabilization device of claim 3, wherein the extending portion has a variable outer diameter that is largest at the base and that decreases as the extending portion extends away from the base.

7. The medical tubing stabilization device of claim 3, wherein a height of the extending portion is greater than a largest inside diameter of the circular bore.

8. The medical tubing stabilization device of claim 3, wherein a thickness between an outer surface and the inner wall of the extending portion decreases along a length of extension of the extending portion away from the base, thereby increasing a flexibility of the extending portion along the length of extension that provides the direct physical contact having the substantially equal pressure about the entire perimeter of the medical tubing disposed within the circular bore.

9. The medical tubing stabilization device of claim 3, wherein the extending portion of the tube engagement element comprises one of:
a conical outer surface tapering from a first outer diameter at the base to a second outer diameter smaller than the first outer diameter; and
a cylindrical outer surface having a constant outer diameter of the first outer diameter.

10. The medical tubing stabilization device of claim 2, wherein a top surface or a bottom surface of the patient attachment element comprises an adhesive layer configured to adhesively couple the tube stabilization patch to at least one of: the skin of the patient, and a surface of the adjustable medical garment.

11. The medical tubing stabilization device of claim 2, wherein the access separation being disposed through the extending portion allows the extending portion to automatically adjust a diameter of the circular bore to accommodate the medical tubing when disposed therethrough and, thereby, provide the direct physical contact having the substantially equal pressure about the entire perimeter of the medical tubing.

12. The medical tubing stabilization device of claim 2, wherein the tube stabilization patch is configured to be adhesively disposed over the third flap, when the adjustable medical garment is donned by the patient, such that:
the access separation extends coextensively along and directly over an edge of the third flap;

a portion of the patient attachment element disposed to a first side of the access separation is adhered to the third flap; and a portion of the patient attachment element disposed to a second side of the access separation opposite the first side is adhered to at least one of the first adjustable flap and the perineum portion, such that gripping a corner of the third flap attached to the first adjustable flap and pulling simultaneously:

releases the third flap from the first adjustable flap, and as the third flap peels away from the first adjustable flap, causes facing edges of the access separation to separate both along the patient attachment element and along the tube engagement element until sidewalls of the circular bore are sufficiently separated to allow the medical tubing to fall out of the tube engagement element when disposed therein.

13. The medical tubing stabilization device of claim 1, wherein the perineal portion is coupled to the edge of the body portion by a seam that is configured to be aligned with a perineum of the patient when the adjustable medical garment is donned by the patient.

14. The medical tubing stabilization device of claim 13, wherein the predetermined distance from the seam to the vertex is between 2 inches and 6 inches and is configured to correspond with a length of the perineum of the patient.

15. The medical tubing stabilization device of claim 13, wherein the perineal portion is configured to extend from the seam under and across the entire perinium of the patient, and the first and second adjustable flaps are configured to extend over the crotch of the patient, to adjustably couple with body portion when the adjustable medical garment is donned by the patient.

16. The medical tubing stabilization device of claim 1, wherein, when the adjustable garment is donned by the patient, a location of the vertex with respect to the body of the patient is adjustable by attaching the end of the first adjustable flap to the first location on the body portion and then attaching the end of the second adjustable flap to the second location on the body portion such that the end of the second adjustable flap is directly adjacent to, or at least partly overlapping, the end of the first adjustable flap.

17. The medical tubing stabilization device of claim 1, wherein the vertex comprises a curved edge having a radius, the curved edge extending to form the opposing medial edges of the first and second adjustable flaps, thereby ensuring that the medial edges of the first and second adjustable flaps immediately extending from the curved edge of the vertex always extend substantially tangential to an outer perimeter of medical tubing having a circular perimeter when extending through the exit port.

18. The medical tubing stabilization device of claim 1, the adjustable medical garment further comprising:

a first attachment portion centrally disposed on an outwardly facing surface of the body portion and comprising a first type of fastener;

a second attachment portion disposed on an inward, or patient-facing surface of the end of the first adjustable flap and comprising a second type of fastener complementary to the first type of fastener;

a third attachment portion disposed on an inward, or patient-facing surface of the end of the second adjustable flap and comprising the second type of fastener, such that the second attachment portion is configured to adjustably couple with the first attachment portion but not with the third attachment portion and so that the third attachment portion is configured to adjustably couple with the first attachment portion but not with the second attachment portion;

a fourth attachment portion, comprising the first type of fastener, disposed along an outward-facing surface of the first adjustable flap and extending, uninterrupted, from the end of the first adjustable flap to a position that is a predetermined distance from the vertex; and a fifth attachment portion, comprising the second type of fastener, disposed along an inward, patient-facing surface of the third flap and directly over at least a portion of the first adjustable flap when the second adjustable flap is adjustably coupled to the first attachment portion, the fifth attachment portion extending, uninterrupted, along substantially an entire width and length of the exposed inward, patient-facing surface of the third flap, such that the fourth attachment portion is configured to adjustably couple with the fifth attachment portion but not with the third attachment portion and the fifth attachment portion is configured to adjustably couple with the fourth attachment portion but not with the first attachment portion.

19. The medical tubing stabilization device of claim 18, wherein, when the third flap is disposed directly on the outward-facing surface of the first flap, the fifth attachment portion is configured to releasably couple with substantially the entire surface of the fourth attachment portion.

20. The medical tubing stabilization device of claim 1, wherein:

when the end of the first adjustable flap is adjustably coupled to the first location on the body portion, a first closed loop leg hole is defined by the edges of the corresponding side of the body portion, the perineal portion and the first adjustable flap; and when the end of the second adjustable flap is adjustably coupled to the second location on the body portion, a second closed-loop leg hole is defined by the edges of the corresponding side of the body portion, the perineal portion and the second adjustable flap.

21. A disposable tube stabilization patch, comprising:

a tube engaging element having a circular bore configured to physically stabilize medical tubing having a circular perimeter by providing direct physical contact having a substantially equal pressure about the entire perimeter of the medical tubing when disposed within the circular bore;

a patient attachment element coupled to and surrounding the tube engaging element; and an access separation extending continuously from an outer edge of the patient attachment element to the circular bore of the tube engaging element, the access separation comprising a cut extending in a wavy line from the outer edge of the patient attachment element to the tube engaging element, thereby forming interlocking extensions, wherein the tube engagement element is configured to receive the medical tubing by passing the medical tubing through the access separation to the tube engaging element.

* * * * *